(12) United States Patent
Fadhel et al.

(10) Patent No.: US 9,722,183 B2
(45) Date of Patent: *Aug. 1, 2017

(54) DISPLAY

(71) Applicant: Novaled GmbH, Dresden (DE)

(72) Inventors: Omrane Fadhel, Dresden (DE); Ramona Pretsch, Dresden (DE); Carsten Rothe, Dresden (DE); Rudolf Lessmann, Duesseldorf (DE); Francois Cardinali, Dresden (DE)

(73) Assignee: Novaled GmbH, Dresden (DE)

( * ) Notice: Subject to any disclaimer, the term of this patent is extended or adjusted under 35 U.S.C. 154(b) by 406 days.

This patent is subject to a terminal disclaimer.

(21) Appl. No.: 14/361,662

(22) PCT Filed: Nov. 30, 2012

(86) PCT No.: PCT/EP2012/004961
§ 371 (c)(1),
(2) Date: May 29, 2014

(87) PCT Pub. No.: WO2013/079217
PCT Pub. Date: Jun. 6, 2013

(65) Prior Publication Data
US 2014/0332790 A1    Nov. 13, 2014

(30) Foreign Application Priority Data

Nov. 30, 2011  (EP) .................................... 11191345
Dec. 12, 2011  (EP) .................................... 11193070

(51) Int. Cl.
*H01L 51/50*    (2006.01)
*H01L 51/00*    (2006.01)
(Continued)

(52) U.S. Cl.
CPC ........ *H01L 51/0054* (2013.01); *C07D 221/18* (2013.01); *C07F 9/64* (2013.01);
(Continued)

(58) Field of Classification Search
None
See application file for complete search history.

(56) References Cited

U.S. PATENT DOCUMENTS 5,093,698 A    3/1992 Egusa
6,878,469 B2   4/2005 Yoon et al.
(Continued)

FOREIGN PATENT DOCUMENTS

CN    1734806 A     2/2006
EP    2 246 862 A1  11/2010
(Continued)

OTHER PUBLICATIONS

Sommer et al., Supramolecular Chemistry: Molecular Recognition and Self-Assembly Using Rigid Spacer-Chelators Bearing Cofacial Terpyridyl Palladium(II) Complexes Separated by 7 angstroms, 2001, J. Am. Chem. Soc., vol. 123, p. 3940-3952.*
(Continued)

*Primary Examiner* — Gregory Clark
(74) *Attorney, Agent, or Firm* — Eversheds Sutherland (US) LLP

(57) ABSTRACT

Display comprising at least one organic light emitting diode, wherein the at least one organic light emitting diode comprises an anode, a cathode, a light emitting layer between the anode and the cathode, and at least one layer comprising a compound according to formula (I) between the cathode and the light emitting layer:

(Continued)

wherein $A^1$ and $A^2$ are independently selected from halogen, CN, substituted or unsubstituted $C_1$-$C_{20}$-alkyl or heteroalkyl, $C_6$-$C_{20}$-aryl or $C_5$-$C_{20}$-heteroaryl, $C_1$-$C_{20}$-alkoxy or $C_6$-$C_{20}$-aryloxy, $A^3$ is selected from substituted or unsubstituted $C_6$-$C_{40}$-aryl or $C_5$-$C_{40}$-heteroaryl, m=0, 1 or 2, n=0, 1 or 2.

15 Claims, 5 Drawing Sheets

(51) Int. Cl.
*C07D 221/18* (2006.01)
*C07F 9/64* (2006.01)
*H01L 27/32* (2006.01)
*C09B 15/00* (2006.01)

(52) U.S. Cl.
CPC .......... *C09B 15/00* (2013.01); *H01L 27/3206* (2013.01); *H01L 27/3244* (2013.01); *H01L 51/0067* (2013.01); *H01L 51/0071* (2013.01); *H01L 51/0072* (2013.01); *H01L 51/5076* (2013.01)

(56) References Cited

U.S. PATENT DOCUMENTS

| | | | |
|---|---|---|---|
| 7,074,500 B2 | 7/2006 | Pfeiffer et al. | |
| 2004/0051724 A1 | 3/2004 | Elliott et al. | |
| 2004/0164292 A1* | 8/2004 | Tung ................ | G02F 1/133603 257/40 |
| 2005/0040390 A1 | 2/2005 | Pfeiffer et al. | |
| 2005/0089717 A1 | 4/2005 | Cosimbescu et al. | |
| 2007/0252140 A1 | 11/2007 | Limmert et al. | |
| 2008/0203406 A1 | 8/2008 | He et al. | |
| 2008/0203905 A1 | 8/2008 | Je et al. | |
| 2008/0227979 A1 | 9/2008 | Saalbeck et al. | |
| 2008/0268282 A1 | 10/2008 | Spindler et al. | |
| 2009/0009072 A1 | 1/2009 | Wellmann et al. | |
| 2009/0045728 A1 | 2/2009 | Murano et al. | |
| 2009/0212280 A1 | 8/2009 | Werner et al. | |
| 2010/0288362 A1 | 11/2010 | Hatwar et al. | |
| 2011/0057559 A1 | 3/2011 | Xia et al. | |
| 2014/0332789 A1 | 11/2014 | Dorok et al. | |
| 2014/0353649 A1 | 12/2014 | Dorok et al. | |

FOREIGN PATENT DOCUMENTS

| | | | |
|---|---|---|---|
| EP | 2 395 571 A1 | 12/2011 | |
| JP | H10-270174 A | 10/1998 | |
| WO | 2009/107596 A1 | 9/2009 | |
| WO | WO 2011154131 | * 12/2011 | ............ H01L 51/00 |

OTHER PUBLICATIONS

PCT International Search Report for PCT Application No. PCT/EP2012/004961 mailed Feb. 26, 2013 (6 pages).

European Search Report for EP Application No. 11 19 3070 mailed May 14, 2012 (2 pages).

Bard et al., "Electrochemical Methods: Fundamentals and Applications," Wiley, 2nd Edition, 2000, pp. 1-28, 239-247.

Connelly et al., "Chemical Redox Agents for Organometallic Chemistry," Chem. Rev., 1996, 96:877-910.

D'Andrade et al., "Relationship Between the Ionization and Oxidation Potentials of Molecular Organic Semiconductors," Organic Electronics, 2005, 6:11-20.

Duan et al., "Controlling the Recombination Zone of White Organic Light-Emitting Diodes with Extremely Long Lifetimes," Adv. Funct. Mater., 2011, 21(18):3540-3545.

Kim et al., "Self-Assembly of Rectangles via Building Units Bearing Salen and Oxazoline Ligands," Journal of Organometallic Chemistry, 2006, 691:5946-5954.

Li et al. "Investigation of Novel Efficient Electron Injection Lithium Complex Containing Quinoxaline Moiety for Organic Light-Emitting Diodes," Jpn. J. Appl. Phys., 2006, 45:L1253-L1255.

Lih et al., "4.3:A Phosphorescent Active-Matrix OLED Display Driven by Amorphous Silicon Backplane," SID 03 Digest, 2003, 14-17.

Liang et al., "A Hydroxyphenyloxadiazole Lithium Complex as a Highly Efficient Blue Emitter and Interface Material in Organic Light-Emitting Diodes," J. Mater. Chem., 2003,13, 2922-2926.

Pu et al., "Lithium Phenolate Complexes for an Electron Injection Layer in Organic Light-Emitting Diodes," Organic Electronics, 2009, 10(2):228-232.

Tang et al., "Organic Electroluminescent Diodes," Appl. Phys. Lett., 1987, 51(12):913-915.

Tsujimura et al., "4.1:A 20-Inch OLED Display Driven by Super-Amorphous-Silicon Technology," SID 03 Digest, 2003, 6-9.

Taiwanese Office Action for TW Application No. 101144998 mailed Jun. 17, 2016 (19 pages) (English translation).

Japanese Office Action for JP Application No. 2014-543803 mailed Nov. 1, 2016 (3 pages) (English translation).

Zimmerman et al., "Rigid Molecular Tweezers: Synthesis, Characterization, and Complexation Chemistry of a Diacridine," J. Am. Chem. Soc., 1987, 109:7894-7896.

Chinese Office Action for CN Application No. 201280067206.5 mailed Dec. 2, 2015 (9 pages) (English translation).

* cited by examiner

DISPLAY

CROSS-REFERENCE TO RELATED APPLICATIONS

This is a submission pursuant to 35 U.S.C. 154(d)(4) to enter the national stage under 35 U.S.C. 371 for PCT/EP2012/004961, filed Nov. 30, 2012. Priority is claimed under 35 U.S.C. 119(a) and 35 U.S.C. 365(b) to European Application No. 11 191 345.5, filed Nov. 30, 2011 and European Application No. 11 193 070.7, filed Dec. 12, 2011. The subject matters of PCT/EP2012/004961 and European Applications No. 11 191 345.5 and 11 193 070 0.7 are incorporated herein by reference.

FIELD OF THE INVENTION

The present invention concerns a display comprising at least one organic light emitting diode with enhanced performance and longer lifetime, and a use of at least one organic light emitting diode in such a display.

BACKGROUND

Since the demonstration of efficient organic light emitting diodes (OLEDs) by Tang et al. in 1987 (C. W. Tang et al., Appl. Phys. Lett. 51 (12), 913 (1987)), OLEDs developed from promising candidates to high-end commercial displays. An OLED comprises a sequence of thin layers substantially made of organic materials. The layers typically have a thickness in the range of 1 nm to 5 μm. The layers are usually formed either in vacuum by means of vapor deposition or from a solution, for example by means of spinning on or printing.

OLEDs emit light after the injection of charge carriers in the form of electrons from the cathode and in form of holes from the anode into organic layers arranged in between. The charge carrier injection is effected on the basis of an applied external voltage, the subsequent formation of excitons in a light emitting zone and the radiative recombination of those excitons. At least one of the electrodes is transparent or semitransparent, in the majority of cases in the form of a transparent oxide, such as indium tin oxide (ITO), or a thin metal layer.

Flat displays based on OLEDs can be realized both as a passive matrix and as an active matrix. In the case of passive matrix displays, the image is generated by for example, the lines being successively selected and an image information item selected on the columns being represented. However, such displays are restricted to a size of approximately 100 lines for technical construction reasons.

Displays having a high information content require active driving of the sub-pixels. For this purpose, each sub-pixel is driven by a circuit having transistors, a driver circuit. The transistors are usually designed as thin film transistors (TFT). Full color displays are known and typically used in mp3-players, digital photo cameras, and mobile phones; earliest devices were produced by the company Sanyo-Kodak. In this case, active matrices made of polysilicon which contain the respective driver circuit for each sub-pixel are used for OLED displays. An alternative to polysilicon is amorphous silicon, as described by J.-J. Lih et al., SID 03 Digest, page 14 et seq. 2003 and T. Tsujimura, SID 03 Digest, page 6 et seq. 2003. Another alternative is to use transistors based on organic semiconductors.

Examples of OLED layer stacks used for displays are described by Duan et al (DOI: 10.1002/adfm.201100943). Duan shows blue OLEDs and white OLEDs. He modified the devices with one light emitting layer to a double and triple light emitting layer, achieving a longer lifetime at the cost of a more complex device stack. Other state-of-the art stacks are disclosed in U.S. Pat. No. 6,878,469 B2, WO 2009/107596 A1 and US 2008/0203905.

It is an objective of the invention to provide an OLED display with better characteristics, especially with a longer lifetime. It is a further object of the present invention to provide a display comprising a specific class of functional materials which can be utilized in the layer structure of the display to overcome the drawbacks of the prior art. The display shall also comprise materials which can be synthesized without any difficulties.

BRIEF DESCRIPTION

The object is achieved by a display comprising at least one organic light emitting diode, wherein the at least one organic light emitting diode comprises an anode, a cathode, a light emitting layer between the anode and the cathode, and at least one layer comprising a compound according to generic formula (I) between the cathode and the light emitting layer:

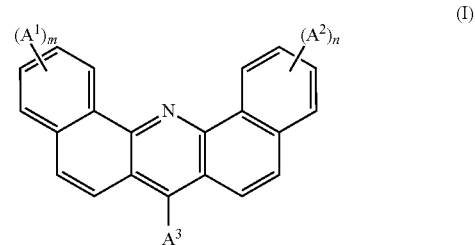

wherein $A^1$ and $A^2$ are independently selected from halogen, CN, substituted or unsubstituted $C_1$-$C_{20}$-alkyl or heteroalkyl, $C_6$-$C_{20}$-aryl or $C_5$-$C_{20}$-heteroaryl, $C_1$-$C_{20}$-alkoxy or $C_6$-$C_{20}$-aryloxy, $A^3$ is selected from substituted or unsubstituted $C_6$-$C_{40}$-aryl or $C_5$-$C_{40}$-heteroaryl, and m and n are independently selected from 0, 1, 2.

In a preferred embodiment, the compound of formula (I) has a structure characterized by the generic formula (II)

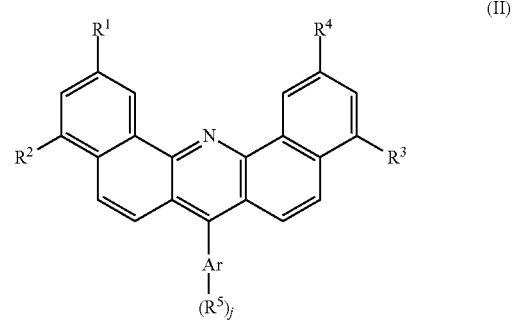

wherein each $R^1$-$R^4$ is independently selected from H, halogen, CN, substituted or unsubstituted $C_1$-$C_{20}$-alkyl or heteroalkyl, $C_6$-$C_{20}$-aryl or $C_5$-$C_{20}$-heteroaryl, $C_1$-$C_{20}$-alkoxy or $C_6$-$C_{20}$-aryloxy, Ar is selected from substituted or unsubstituted $C_6$-$C_{24}$-arene or $C_5$-$C_{24}$-heteroarene, j=1 or 2, and each $R^5$ is independently selected from substituted or unsubstituted $C_6$-$C_{20}$-aryl or $C_5$-$C_{20}$-heteroaryl, H, F or

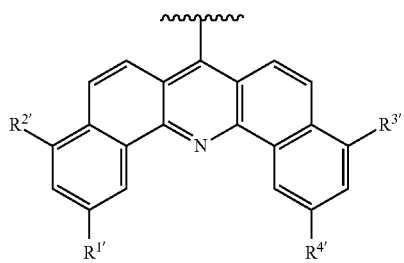

wherein each $R^{1'}$-$R^{4'}$ is independently selected from the same group as $R^1$-$R^4$ defined above.

Preferably, each of R1-R4 is independently selected from H, substituted or unsubstituted C6-C20 aryl and C5-C20-heteroaryl. Even preferably, Ar is a divalent radical derived from substituted or unsubstituted C6-C24 arylene or from substituted or unsubstituted C5-C24-heteroarylene. It is to be understood that the term substituted or unsubstituted arylene stands for a divalent radical derived from substituted or unsubstituted arene, wherein the both adjacent structural moieties (in formula (II), the dibenz(acridine) core and R5) are attached directly to an aromatic ring of the arylene group. Examples of simple arylenes are o-, m- and p-phenylene; polycyclic arylenes may have their adjacent groups attached either on the same aromatic ring or on two different aromatic rings.

More preferably, j=1 and Ar is an arylene or heteroarylene selected from

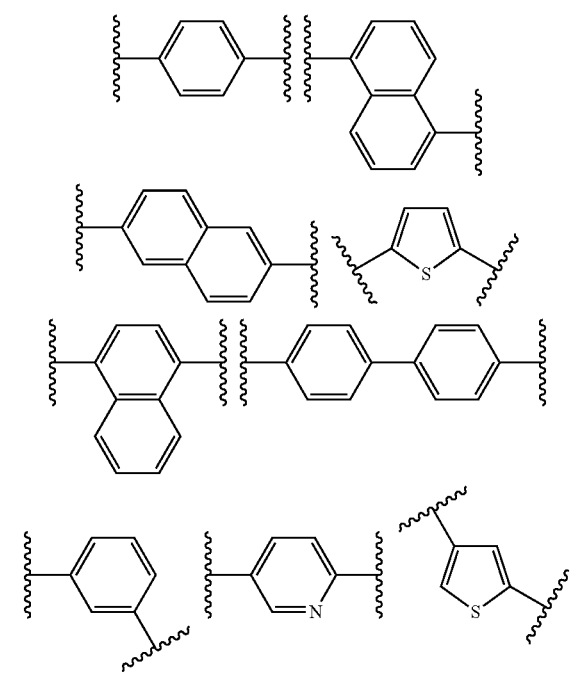

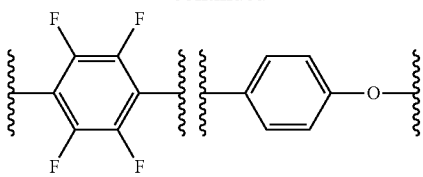

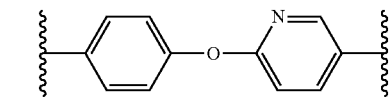

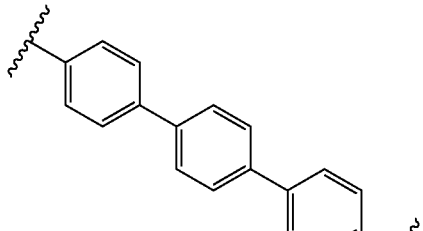

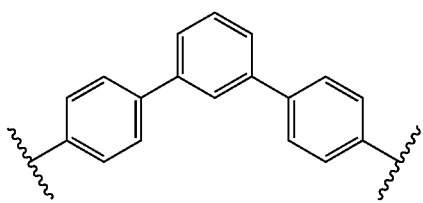

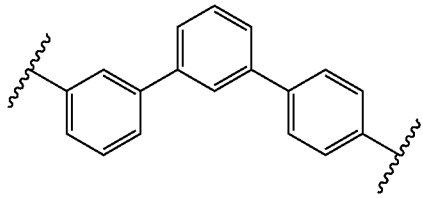

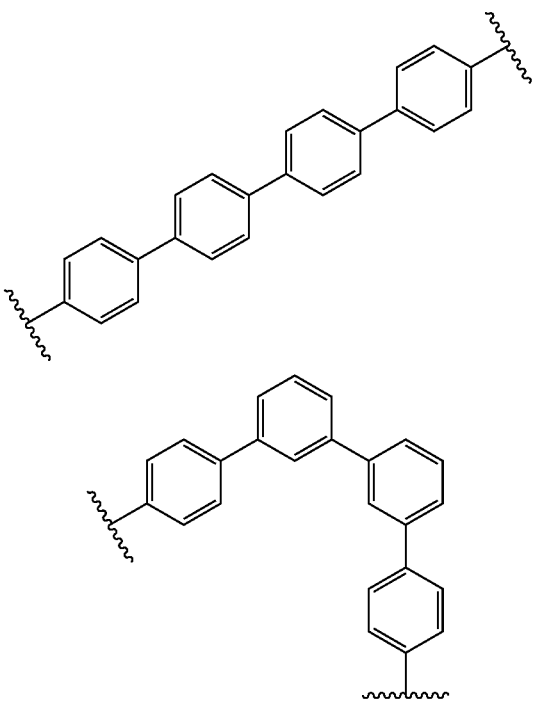

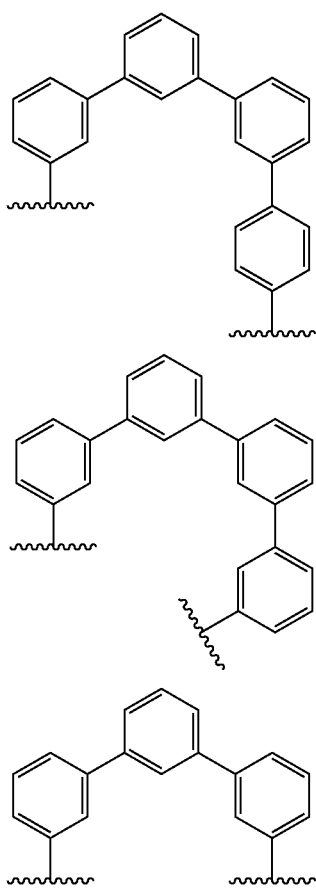

It is further preferred that A3 in the formula (I) or R5 in the formula (II) comprises at least one of the following chemical groups: phosphine sulphide, phosphine oxide, imidazole, oxazole. More preferred are compounds substituted in A3 or R5 with at least one phosphine oxide or phosphine sulphide group.

It is also preferred when the display comprises compound having general structure (II) wherein R5 is H or F, and particularly when R5 combines with Ar to a moiety selected from

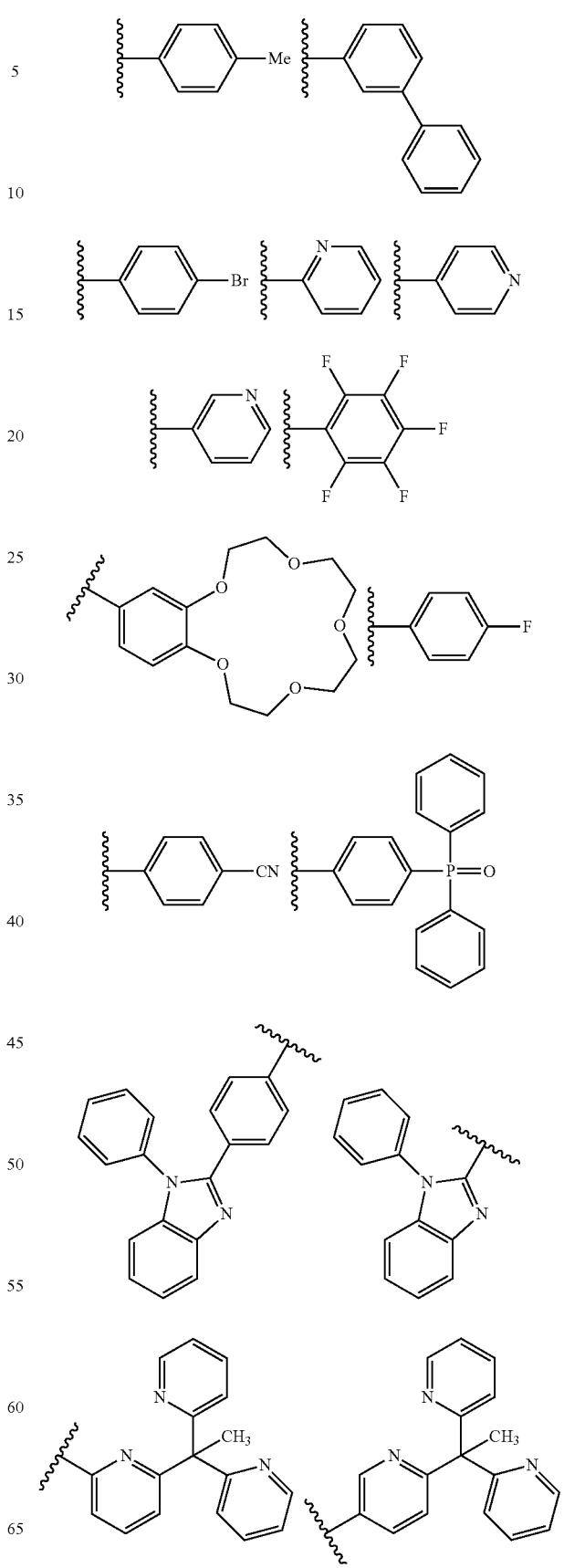

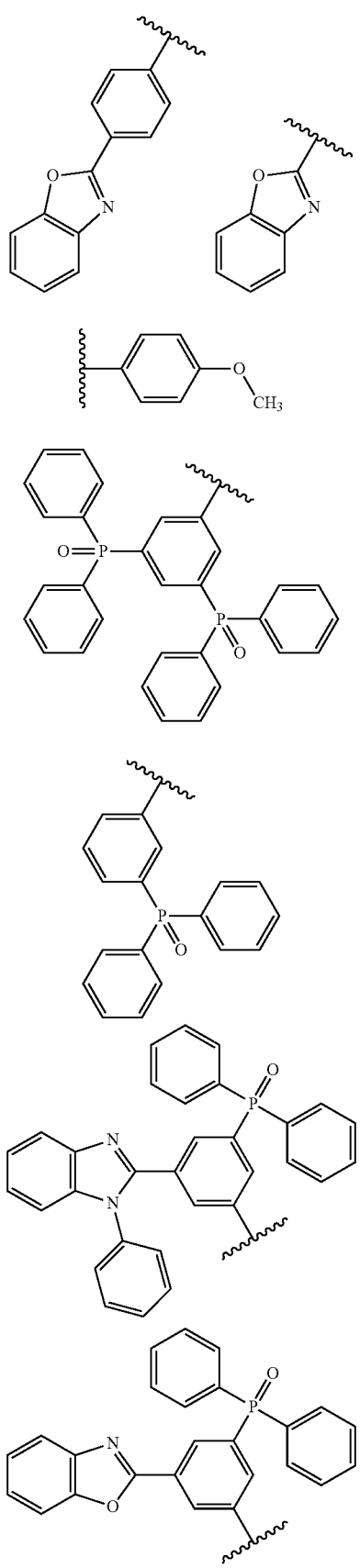
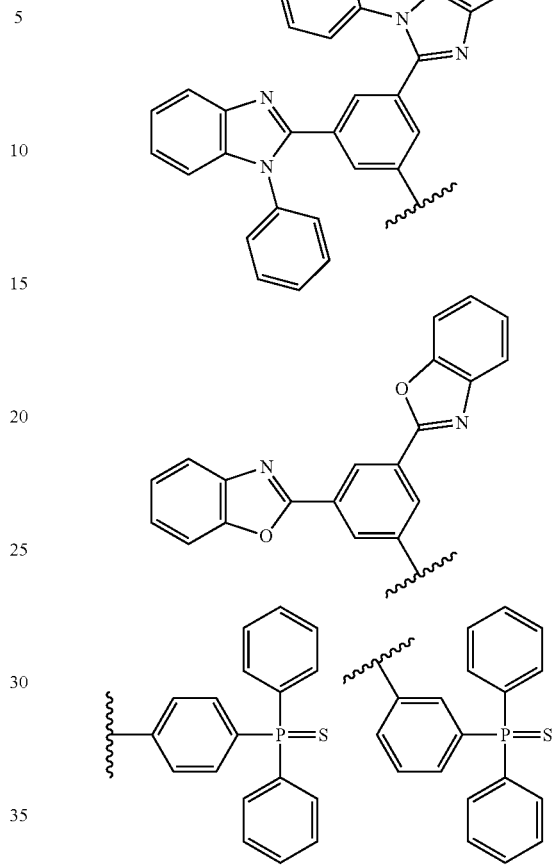

Also preferably, A3 in the formula (I) is

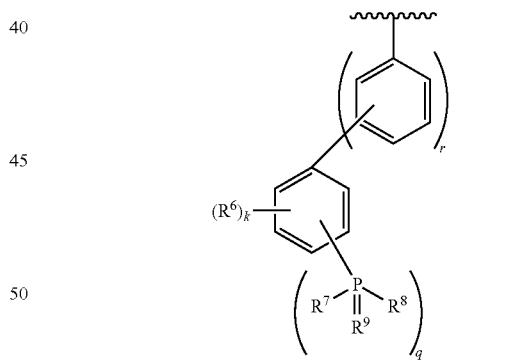

and each of $A^1$, $A^2$ and $R^6$ is independently selected from H, halogen, CN, substituted or unsubstituted $C_1$-$C_{20}$-alkyl or heteroalkyl, $C_6$-$C_2$-aryl or $C_5$-$C_{20}$-heteroaryl, $C_1$-$C_{20}$-alkoxy or $C_6$-$C_{20}$-aryloxy, each of $R^7$ and $R^8$ is independently selected from $C_6$-$C_{20}$-aryl or $C_5$-$C_{20}$-heteroaryl which can be unsubstituted or substituted, $R^9$ is O or S, r is 0, 1, 2, 3 or 4, k is 0 or 1, and q is 1, 2 or 3. For r=0 it is of course to be understood that the substituent attached shall then be directly connected to the acridine scaffold.

It is to be understood that wherever a substituted or unsubstituted carbon rest such as alkyl, aryl, heteroalkyl, heteroaryl etc. is mentioned, all carbon atoms covalently bound in the rest are included in the overall count of carbon atoms specified for this carbon rest. The term C10 aryl thus for example comprises not only 1- or 2-naphtyl but also all isomeric butylphenyls, diethylphenyls, methyl-propylphenyls and tetramethylphenyls. It is further to be understood that the term alkyl comprises not only straight and branched alkyl like methyl, ethyl, propyl, isopropyl, but also cycloalkyls like cyclohexyl or alkyls comprising branched or cyclic structures and that these structures may include unsaturated bonds such as double or triple bonds and/or aromatic structures. In that broad sense, the term alkyl as used throughout this application includes also arylalkyl groups such as e.g. benzyl, diphenylmethyl, or 2-phenylethyl. It is further to be understood that the term heteroalkyl comprises alkyls wherein at least one carbon atom in a carbon chain having at least two carbon atoms or in a cycle having at least three atoms is replaced by a di-, tri-, tetra-, penta- or hexavalent heteroatom like e.g. B, O, S, N, P, Si or at least two hydrogen atoms on a carbon atom of an alkyl substituent are replaced by an oxygen atom or by a nitrogen atom. In this broad sense, the term heteroalkyl includes chain or cyclic carbon structures comprising e.g. ether, acetal, ester, keto, sulphide, sulphoxide, sulphone, amine, imine, amide, nitrile, phosphine or phosphinoxide groups as well as heteroaryl-substituted alkyl groups.

The object of the invention is further achieved by the use of at least one organic light emitting diode in a display, wherein the organic light emitting diode comprises an anode, a cathode, a light emitting layer between the anode and the cathode, and at least one layer comprising a compound according to formula (I) as defined above between the cathode and the light emitting layer.

The object of the invention is further achieved by display comprising new compound according to formula (I):

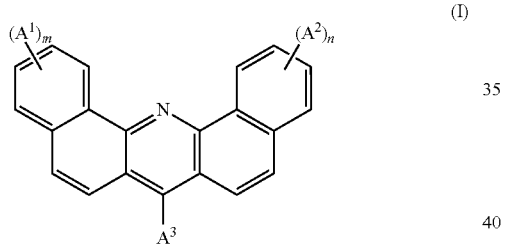

(I)

wherein $A^1$ and $A^2$ are independently selected from halogen, CN, substituted or unsubstituted $C_1$-$C_{20}$-alkyl or heteroalkyl, $C_6$-$C_{20}$-aryl or $C_5$-$C_{20}$-heteroaryl, $C_1$-$C_{20}$-alkoxy or $C_6$-$C_{20}$-aryloxy,
m and n are independently selected from 0, 1 and 2,
$A^3$ is

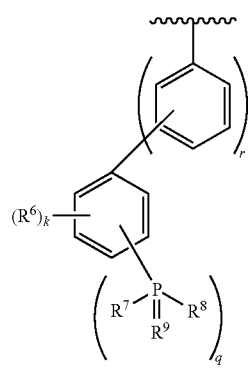

wherein $R^6$ is selected from H, halogen, CN, substituted or unsubstituted C1-C20-alkyl or C1-C20-heteroalkyl, C6-C20-aryl or C5-C20-heteroaryl, C1-C20-alkoxy or C6-C20-aryloxy;

each of $R^7$ and $R^8$ is independently selected from substituted or unsubstituted C6-C20-aryl or C5-C20-heteroaryl;
q is selected from 1, 2, and 3;
k is 0 or 1,
r is selected from 0, 1, 2, 3 or 4,
$R^9$ is O or S;
wherein the following compounds are excluded:

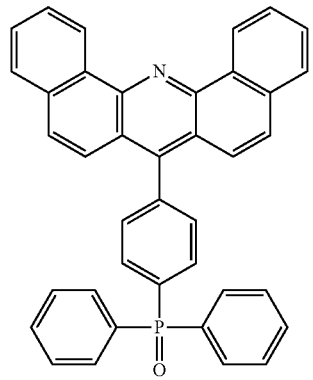

(i)

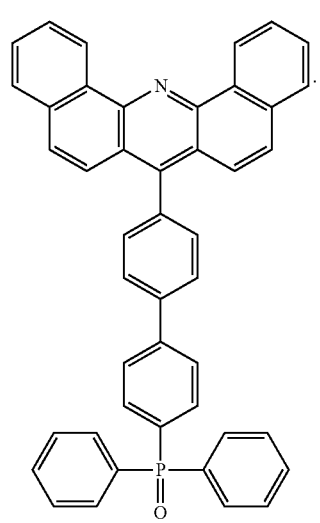

(ii)

Preferred embodiments are disclosed in the sub-claims.

The invention is a display comprising at least one OLED, wherein the at least one OLED comprises an anode, a cathode, a light emitting layer between the anode and the cathode, and at least one layer comprising a compound according to formula (I) between the cathode and the light emitting layer. The compound according to formula (I) is an inventive electron transport material (IETM), and is described further below. The layer comprising the IETM is also called IETL.

In one aspect of the invention the display comprises at least one second OLED, wherein the first OLED and the second OLED emit in different colors. In one aspect each first OLED or second OLED have monochromatic emission, where the colours are selected from red, green, and blue. In another aspect, the emitted color is selected from red, green, blue and white. In another aspect, the emitted color is selected at least from deep blue and light blue.

The display is preferably a matrix array display, more preferably an active matrix array display.

Preferred applications of displays range from mobile phones, portable music players, portable computers and other personal portable devices to car radio receivers, television sets, computer monitors, and more.

It is also in the sense of the invention, that the layer comprising the IETM preferably comprises an additional material. The additional material is preferably selected from metal salt or metal complex. Alternatively or in addition, the additional material is preferably an electrical n-dopant.

It is also in the sense of the invention, that the IETM is preferably used as in an exciton blocking layer.

It is also in the sense of the invention, that the OLED preferably comprises the IETL and an additional IETL. Preferably one of the IETL and the additional IETL is a pure layer consisting of IETM, and the other comprises the additional material.

In another aspect of the invention, the OLED has a charge generation layer, wherein the charge generation layer comprises the IETM.

A further embodiment of the invention is a compound, and a display using such compound, the compound being according to formula (III):

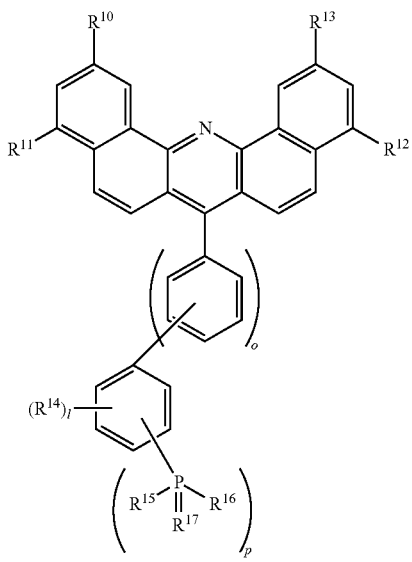

(III)

wherein $R^{10}$-$R^{14}$ are independently selected from H, halogen, CN, substituted or unsubstituted C1-C20-alkyl or C1-C20-heteroalkyl, C6-C20-aryl or C5-C20-heteroaryl, C1-C20-alkoxy or C6-C20-aryloxy;
each of $R^{15}$ and $R^{16}$ is independently selected from substituted or unsubstituted C6-C20-aryl or C5-C20-heteroaryl;
p is selected from 1, 2, and 3;
l is 0 or 1,
o is selected from 0, 1, 2, 3 or 4,
$R^7$ is O or S
wherein the following compounds are excluded:

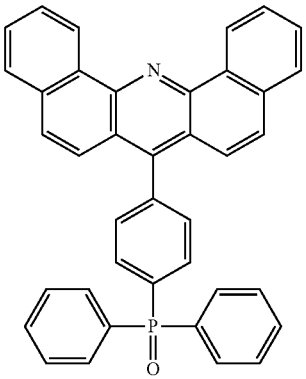

(i)

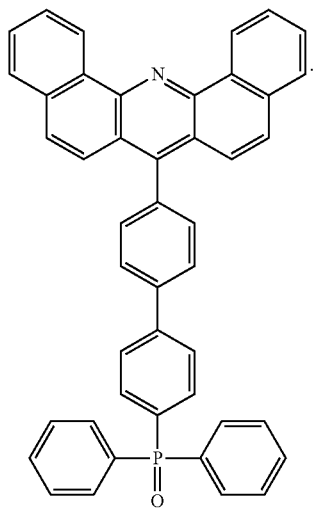

(ii)

In formula (III), it is to be understood that, if o=0, that the phenyl group bearing the substituent R14 and the phosphine substituent is directly attached via a single bond to the acridine scaffold. Further, it is to be understood that, if o=2, this results in a biphenyl structure, wherein one of the benzene moieties of the biphenyl structure may be substituted as illustrated in formula (III).

Preferably, the compound (III) is characterized by generic formula (IV)

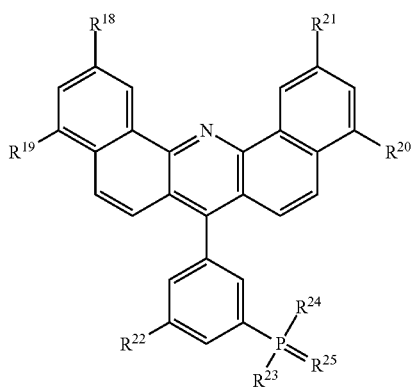

(IV)

wherein each of $R^{18}$-$R^{22}$ is independently selected from H, halogen, CN, substituted or unsubstituted C1-C20-alkyl or C1-C20-heteroalkyl, C6-C20-aryl or C5-C20-heteroaryl, C1-C20-alkoxy or C6-C20-aryloxy;
each of $R^{23}$ and $R^{24}$ is independently selected from substituted or unsubstituted C6-C20-aryl or C5-C20-heteroaryl, and
$R^{25}$ is O or S.

More preferably, each of R18-R21 in formula (IV) is independently selected from H, and from, each either substituted or unsubstituted, C1-C20-alkyl, C1-C20-heteroalkyl, C1-C20-alkoxy and C6-C20-aryloxy; and
$R^{22}$ is selected from H and substituted or unsubstituted C6-C20-aryl or C5-C20-heteroaryl and each of $R^{23}$ and $R^{24}$ is independently selected from substituted or unsubstituted C6-C20-aryl or C5-C20-heteroaryl, and
R2 is O.

Advantageous Effect of the Invention

With the invention it is possible to obtain much longer lifetime for a display pixel (and subpixels), while maintaining low operating voltage. The advantages are especially relevant for blue OLEDs, even more for singlet blue emitters.

In addition, with the inventive IETM it is possible to use the same material in ETLs of adjacent sub-pixels of different colors and different emitter types (fluorescent or phosphorescent), achieving higher efficiency in with the fluorescent emitters without jeopardizing the performance of the phosphorescent sub-pixels.

Also equivalent advantage is achieved in white OLEDs, such as stacked OLEDs, which are combined with color filters in a display.

DETAILED DESCRIPTION OF THE INVENTION

Device Architecture

Figure 1:
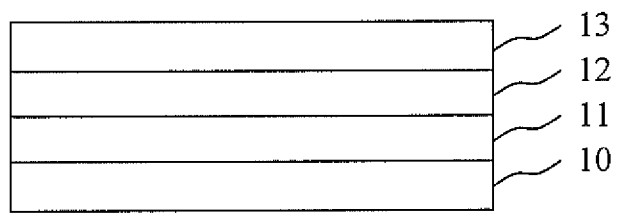
FIG. 1 shows a schematic illustration of the layer structure of an OLED which can be utilized in an inventive display.

FIG. 1 shows a stack of anode (10), organic semiconducting layer (11) comprising the light emitting layer, IETL (12), and cathode (13). Other layers can be inserted between those depicted, as explained herein.

Figure 2:
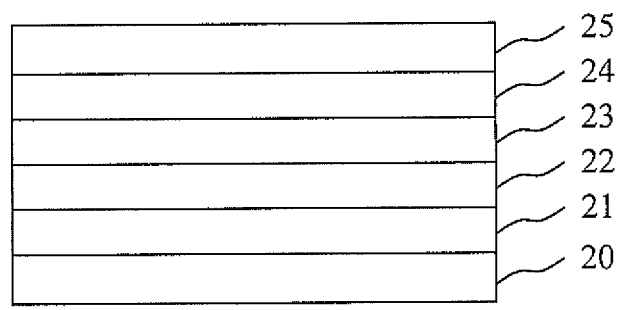
FIG. 2 shows a schematic illustration of the layer structure of another OLED which can be utilized in an inventive display.

FIG. 2 shows a stack of an anode (20), a hole injecting and transporting layer (21), a hole transporting layer (22) which can also aggregate the function of electron blocking, a light emitting layer (23), an IETL (24), and a cathode (25). Other layers can be inserted between those depicted, as explained herein.

Material Properties—Energy Levels

A method to determine the ionization potentials (IP) is the ultraviolet photo spectroscopy (UPS). It is usual to measure the ionization potential for solid state materials; however, it is also possible to measure the IP in the gas phase. Both values are differentiated by their solid state effects, which are, for example the polarization energy of the holes that are created during the photo ionization process. A typical value for the polarization energy is approximately 1 eV, but larger discrepancies of the values can also occur. The IP is related to beginning of the photoemission spectra in the region of the large kinetic energy of the photoelectrons, i.e. the energy of the most weakly bounded electrons. A related method to UPS, the inverted photo electron spectroscopy (IPES) can be used to determine the electron affinity (EA). However, this method is less common. Electrochemical measurements in solution are an alternative to the determination of solid state oxidation (Eox) and reduction (Ered) potential. An adequate method is for example the cyclo-voltammetry. A simple rule is used very often for the conversion of red/ox potentials into electron affinities and ionization potential: IP=4.8 eV+e*Eox (vs. Ferrocen/Ferrocenium) and EA=4.8 eV+e*Ered (vs. Ferrocen/Ferrocenium) respectively (see B. W. Andrade, Org. Electron. 6, 11 (2005)). Processes are known for the correction of the electrochemical potentials in the case other reference electrodes or other redox pairs are used (see A. J. Bard, L. R. Faulkner, "Electrochemical Methods: Fundamentals and Applications", Wiley, 2. Ausgabe 2000). The information about the influence of the solution used can be found in N. G. Connelly et al., Chem. Rev. 96, 877 (1996). It is usual, even if not exactly correct to use the terms, "energy of the HOMO" E(HOMO) and "energy of the LUMO" E(LUMO) respectively as synonyms for the ionization energy and electron affinity (Koopmans Theorem). It has to be taken in consideration, that the ionization potentials and the electron affinities are given in such a way that a larger value represents a stronger binding of a released or respectively of an absorbed electron. The energy scale of the molecular orbitals (HOMO, LUMO) is opposed to this. Therefore, in a rough approximation, is valid: IP=−E(HOMO) and EA=E(LUMO). The given potentials correspond to the solid-state potentials.

Substrate

It can be flexible or rigid, transparent, opaque, reflective, or translucent. The substrate should be transparent or translucent if the light generated by the OLED is to be transmitted through the substrate (bottom emitting). The substrate may be opaque if the light generated by the OLED is to be emitted in the direction opposite of the substrate, the so called top-emitting type. The display can also be fully transparent. The substrate can be either arranged adjacent to the cathode or anode.

Electrodes

The electrodes are the anode and the cathode, they must provide a certain amount of conductivity, being preferentially conductors. At least one of the electrodes must be semitransparent or transparent to enable the light transmission to the outside of the device. Typical electrodes are layers or a stack of layer, comprising metal and/or transparent conductive oxide. Other possible electrodes are made of thin busbars (e.g. a thin metal grid) wherein the spaces between the busbars is filled (coated) with a transparent material with a certain conductivity, such as graphene, carbon nanotubes, doped organic semiconductors, etc.

In one mode, the anode is the electrode closest to the substrate, which is called non-inverted structure. In another mode, the cathode is the electrode closest to the substrate, which is called inverted structure.

Typical materials for the Anode are ITO and Ag. Typical materials for the cathode are Mg:Ag (10 vol % of Mg), Ag, ITO, Al. Mixtures and multilayer are also possible.

Preferably, the cathode comprises a metal selected from Ag, Al, Mg, Ba, Ca, Yb, In, Zn, Sn, Sm, Bi, Eu, Li, more preferably from Al, Mg, Ca, Ba and even more preferably selected from Al or Mg. Preferred is also a cathode comprising an alloy of Mg and Ag.

Hole-Transporting Layer (HTL)

Is a layer comprising a large gap semiconductor responsible to transport holes from the anode or holes from a CGL to the light emitting layer (LEL). The HTL is comprised between the anode and the LEL or between the hole generating side of a CGL and the LEL. The HTL can be mixed with another material, for example a p-dopant, in which case it is said the HTL is p-doped. The HTL can be comprised by several layers, which can have different compositions. P-doping the HTL lowers its resistivity and avoids the respective power loss due to the otherwise high resistivity of the undoped semiconductor. The doped HTL can also be used as optical spacer, because it can be made very thick, up to 1000 nm or more without significant increase in resistivity.

Hole-Injecting Layer (HIL)

Is a layer which facilitates the injection of holes from the anode or from the hole generating side of a CGL into an adjacent HTL. Typically the HIL is a very thin layer (<10 nm). The hole injection layer can be a pure layer of p-dopant and can be about 1 nm thick. When the HTL is doped, an HIL may not be necessary, since the injection function is already provided by the HTL.

Light-Emitting Layer (LEL)

The light emitting layer must comprise at least one emission material and can optionally comprise additional layers. If the LEL comprises a mixture of two or more materials the charge carrier injection can occur in different materials for instance in a material which is not the emitter, or the charge carrier injection can also occur directly into the emitter. Many different energy transfer processes can occur inside the LEL or adjacent LELs leading to different types of emission. For instance excitons can be formed in a host material and then be transferred as singlet or triplet excitons to an emitter material which can be singlet or triplet emitter which then emits light. A mixture of different types of emitter can be provided for higher efficiency. Mixed light can be realized by using emission from an emitter host and an emitter dopant.

The best performance enhancement is achieved with blue fluorescent emitters.

Blocking layers can be used to improve the confinement of charge carriers in the LEL, these blocking layers are further explained in U.S. Pat. No. 7,074,500 B2.

Electron-Transporting Layer (ETL)

Is a layer comprising a large gap semiconductor responsible to transport electrons from the cathode or electrons from a CGL to the light emitting layer (LEL). The ETL is comprised between the anode and the LEL or between the electron generating side of a CGL and the LEL. The ETL can be mixed with another material, for example a n-dopant, in which case it is said the ETL is n-doped. The ETL can be comprised by several layers, which can have different compositions. N-doping the ETL lowers its resistivity and avoids the respective power loss due to the otherwise high resistivity of the undoped semiconductor. The doped ETL can also be used as optical spacer, because it can be made very thick, up to 1000 nm or more without significant increase in resistivity.

The present invention employs a compound according to formula (I) in the ETL, which compound can be used in combination with other materials, in the whole layer or in a sub-layer of the ETL.

Hole blocking layers and electron blocking layers can be employed as usual. In a preferred mode of the invention, the LEL has a very low HOMO and an EBL is not necessary. That is because the recombination of charge carriers with light emission is close or at the HTL/LEL interface.

Electron-Injecting Layer (EIL)

Several different techniques for providing EILs can be used. Some of those techniques are explained below: the device can comprise a buffer layer between the cathode and the ETL. This buffer layer can provide protection against the cathode deposition or metal diffusion from the cathode. Sometimes this buffer layer is named as buffer or as injection layer. Another kind of injection layer is a layer comprising an n-dopant between the ETL and the cathode. This layer can be a pure layer of n-dopant which is typically less than 5 nm thick, typically only about 1 nm thick. The use of the strong donor (n-dopant) as injection layer provides lower voltages and higher efficiency in the device. If the ETL is n-doped, then the injection layer may not be necessary. Other kinds of injection layers are: metal doped organic layer, typically using alkali metals; thin layer of a metal complexes (such as lithium quinolate (LiQ)), inorganic salts (such as LiF, NaCl, etc).

The best mode of the present invention is achieved by mixing the ETL with an additional material such as, as for example metal complexes, such as for example LiQ. Especially for blue OLEDs for display applications this mixing enables higher efficiency and longer lifetime.

In another mode of the invention, the additional material is an n-dopant.

Other layers with different functions can be included, and the device architecture can be adapted as known by the skilled in the art.

Charge Generation Layer (CGL)

The OLED can comprise a CGL which can be used in conjunction with an electrode as inversion contact, or as connecting unit in stacked OLEDs. A CGL can have the most different configurations and names, examples are pn-junction, connecting unit, tunnel junction, etc. Best examples are pn junctions as disclosed in US 2009/0045728 A1, US 2010/0288362 A1. Metal layers and or insulating layers can also be used.

Stacked OLEDs

When the OLED comprises two or more LELs separated by CGLs, the OLED is named a stacked OLED, otherwise it is named a single unit OLED. The group of layers between two closest CGLs or between one of the electrodes and the closest CGL is named a electroluminescent unit (ELU). Therefore a stacked OLED can be described as anode/ELU1/{CGLX/ELU1+X}X/cathode, wherein x is a positive integer and each CGLX or each ELU1+X can be equal or different. The CGL can also be formed by the adjacent layers of two ELUs as disclosed in US2009/0009072 A1. Further stacked OLEDs are explained e.g. in US 2009/0045728 A1, US 2010/0288362 A1, and references therein.

Pixel Structure

The pixel is sub-structured into sub-pixels with different colors so that each pixel is enabled to render the whole required color space (e.g. NTSC, CIE 1931, extended ISO RGB). There are two main OLED configuration used for such displays:

(i) all OLEDs are white having the same layer stack configuration and the different colors are provided by color filters, the OLEDs are broadband emitting, in the best case having emission peaks (or bands) well matching the transmission of the color filters.

(ii) the OLEDs have multiple colors, typically at least 3 colors. In this mode it is preferred that each OLED have a single ELU, that simplifies the production process and provided the lowest driving voltage for the display. A filter can still be used in addition, to reduce blurring and ensure a more pure color for each sub-pixel.

Figure 4:
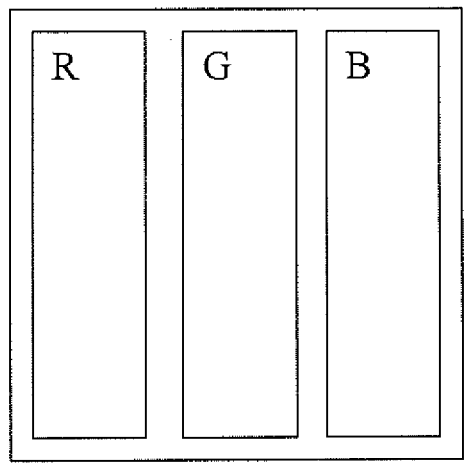
FIG. 4 shows a schematic illustration of a sub-pixel arrangement.

Different configurations of subpixels can be used for each pixel of the display. In one preferred mode of the invention, each pixel consists of lateral red, green, and blue stripes (RGB). Such a configuration is depicted in FIG. 4, the outer rectangle delimits the region where the pixel is constructed, in which pixel comprises a red (R), a green (G), and a blue (B) stripe.

The color space can also be rendered by sub-pixels of different geometries and different colors, for example using RGBY, where Y stands for yellow, using RGBW, where W stands for white. Some rendering technologies can also be used in which a sub-pixel is shared between 2 or more pixels, requiring sub-pixel rendering, see for example US 2004 0051724 A1, which paragraph 0003 is incorporated herein by reference. The left side of FIG. 5 shows a pixel formed by 4 sub-pixels in the RGBW configuration.

Figure 5:
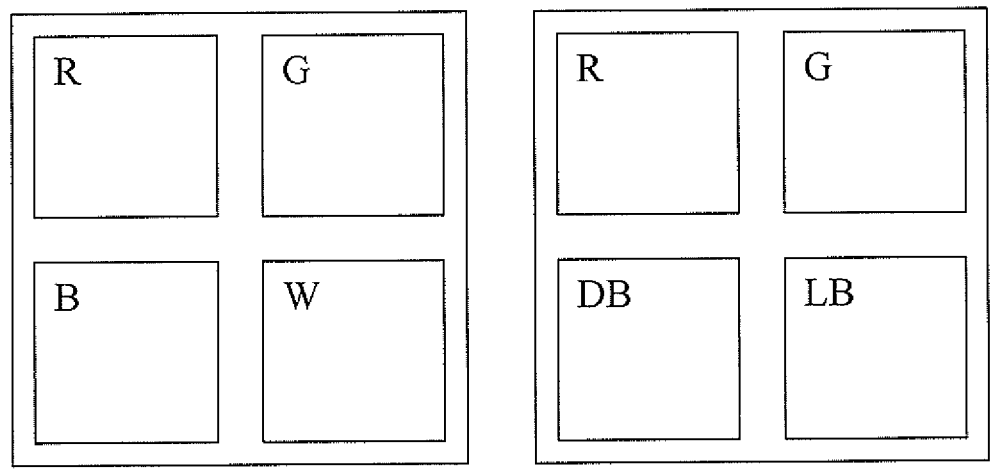
FIG. 5 shows two schematic illustrations of sub-pixel arrangements.

Other arrangements provide longer lifetimes to the display, for example as depicted in the right side of FIG. 5. In FIG. 5 a red (R), a green (G), a deep blue (DB), and a light blue (LB) sub-pixel are used, mainly to improve the lifetime of the blue color, because deep-blue has a shorter lifetime and is not always required in the image. This configuration can also improve overall power efficiency, if a phosphorescent blue emitter is used instead of a fluorescent in the LB sub-pixel. The arrangements of FIG. 5 can also have another desired geometry, such as side-by-side strips. However, the depicted geometry is preferred for non-subpixel rendering of a pixel comprising 4 sub-pixels.

Electronic Structure of the Display's Sub-pixel

Figure 3:
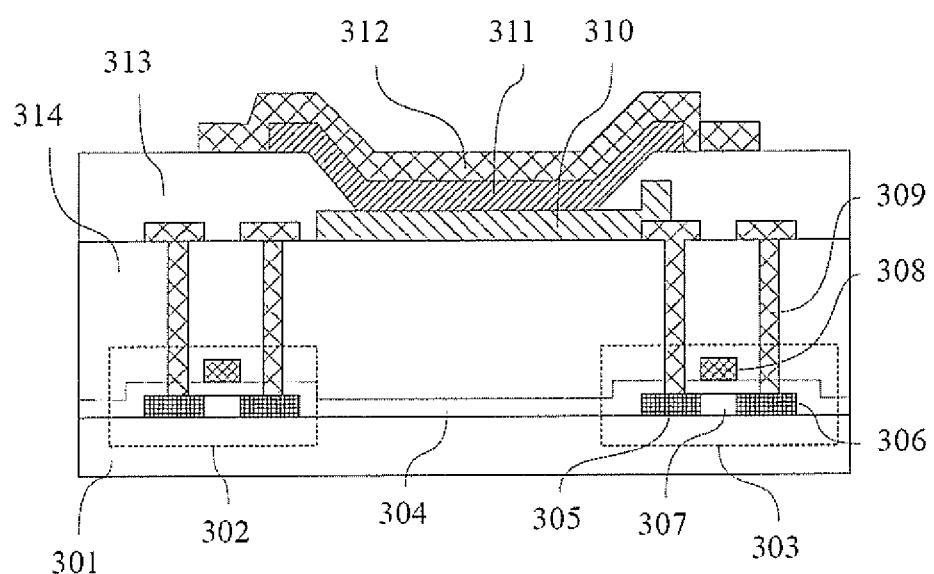
FIG. 3 shows a schematic illustration of the layer structure of an OLED and its correspondent driver transistor which can be utilized in an inventive display.

A sub-pixel is a one colour element which at least 3 different colour element are necessary for creating a pixel of a colour display. For a monochromatic display, the sub-pixel is the pixel itself. FIG. 3 shows the cross sectional view of an exemplary configuration of an OLED with its respective transistors in a display. The OLED is represented by bottom electrode (310), top electrode (312), and the semiconductor layers (311) comprising the IETM between the bottom and the top electrodes. Bottom and top electrodes are selected from anode and cathode, depending on the polarity supplied by transistors (302, 303). In one mode of the invention the bottom electrode (310), an insulating layer (314), further insulating layer (313) and substrate (301) are transparent, with electrode (312) being not transparent, the OLED being of bottom emitting type. In another mode of the invention the OLED is top-emitting, wherein the bottom electrode (310) is not transparent and the top electrode (312) is transparent. In yet another mode of the invention the display is transparent and layers (301, 302, 310, 311, 312) are transparent in the visible. Gate insulating layer (304) needs to be transparent if necessary, and it is transparent anyway in most of the cases due to the use of high gap dielectric materials.

Transistor (301) is the driving transistor which controls the current flowing through the OLED, this transistor comprises two source and drain electrodes (305, 306, not necessarily in this order), a semiconducting layer (307), a gate insulating layer (304), a gate electrode (308). A via (wiring) connects transistor's electrode (305) to the OLED's electrode (310). The switching transistor (302) controls the video signal applied to the driving transistor (301). An insulating layer (314) separates the transistors from the OLED and supports vias (309). A further insulating layer (314) separates the wirings from the electrodes of the OLED.

Further components are known by the skilled in the art and therefore not shown, for instance the capacitors are not in the same plane of FIG. 3 and more transistors could be used in the circuit.

The best configuration is achieved with top-emitting OLEDs due to the larger fill factor area.

The OLED structures described herein can deposited on a backplane structure in form of sub-pixels, example for the backplane circuit is the one described in conjunction with FIG. 3. This construct is then encapsulated and connected to the electronic driver to serve as a display. Typically, antireflection means are further incorporated to the display.

Deposition of Organic Layers

Any organic semiconducting layers of the inventive display can be deposited by known techniques, such as vacuum thermal evaporation (VTE), organic vapour phase deposition, laser induced thermal transfer, spin coating, blade coating, slot dye coating, inkjet printing, etc. A preferred method for preparing the OLED according to the invention is vacuum thermal evaporation.

Preferably, the EITL is formed by evaporation. When using an additional material in the EITL it is preferred that the EITL is formed by co-evaporation of the EITM and the additional material. The additional material may be mixed homogeneously in the EITL. In one mode of the invention, the additional material has a concentration variation in the EITL, wherein the concentration changes in the direction of the thickness of the stack of layers. It is also foreseen that the EITL is structured in sub-layers, wherein some but not all of these sub-layers comprise the additional material.

Electrical Doping

The most reliable and at the same time efficient OLEDs are OLEDs comprising doped layers. By electrically doping hole transport layers with a suitable acceptor material (p-doping) or electron transport layers with a donor material (n-doping), respectively, the density of charge carriers in organic solids (and therefore the conductivity) can be increased substantially. Additionally, analogous to the experience with inorganic semiconductors, some applications can be anticipated which are precisely based on the use of p- and n-doped layers in a component and otherwise would be not conceivable. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

The present invention can be used in addition or in combination with electrical doping of organic semiconducting layers. This electrical doping can also be called redox-doping or charge transfer doping. It is known that the doping increases the density of charge carriers of a semiconducting matrix towards the charge carrier density of the undoped matrix.

US2008227979 discloses in detail the doping of organic transport materials, with inorganic and with organic dopants. Basically, an effective electronic transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of doped hole transport materials are: copper phthalocyanine (CuPc), which HOMO level is approximately −5.2 eV, doped with tetrafluoro-tetracyano-quinonedimethane (F4TCNQ), which LUMO level is about −5.2 eV; zincphthalocyanine (ZnPc) (HOMO=−5.2 eV) doped with F4TCNQ; a-NPD (N,N'-Bis(naphthalen-1-yl)-N,N'-bis(phenyl)-benzidine) doped with F4TCNQ. a-NPD doped with 2,2'-(perfluoronaphthalene-2,6-diylidene)dimalononitrile (PD1). a-NPD doped with 2,2',2"-(cyclopropane-1,2,3-triylidene)tris(2-(p-cyanotetrafluorophenyl)acetonitrile) (PD2). All p-doping in the device examples were done with 5 mol. % of PD2.

Typical examples of doped electron transport materials are: fullerene C60 doped with acridine orange base (AOB); perylene-3,4,9,10-tetracarboxylic-3,4,9,10-dianhydride (PTCDA) doped with leuco crystal violet; 2,9-di(phenanthren-9-yl)-4,7-diphenyl-1,10-phenanthroline doped with tetrakis(1,3,4,6,7,8-hexahydro-2H-pyrimido[1,2-a]pyrimidinato) ditung-sten (II) (W2(hpp)4); naphthalene tetracarboxylic acid di-anhydride (NTCDA) doped with 3,6-bis-(dimethyl amino)-acridine; NTCDA doped with bis (ethylene-dithio) tetrathiafulvalene (BEDT-TTF).

Materials

Preferred emission ranges are:
Blue emission having a peak between 440 nm and 490 nm.
Yellow emission having a peak between 550 nm and 590 nm.
Green emission having a peak between 500 and 540 nm.
Red emission having a peak between 600 and 700 nm.
Known emitter dopants can be used in the invention.

Preferred Emitters

Exemplary fluorescent red emitter dopants are diindenoperylene compounds such as e.g.: 5,10,15,20-tetraphenylbenzo[ghi]benzo[5,6]indeno[1,2,3-cd]benzo[5,6]indeno[1,2,3-lm]perylene; 5,10,15,20-tetraphenyl-7,8-dihydrobenzo[5,6]indeno[1,2,3-cd]benzo[5,6]indeno[1,2,3-lm]perylene; 1,2,3,4,9,10,11,12-octaphenyl-6,7-dihydrodiindeno[1,2,3-cd: 1',2',3'-lm]perylene.

Exemplary fluorescent orange or yellow emitters are 5,6,11,12-tetraphenyltetracene; 5,6,11,12-tetra(naphthalen-2-yl)tetracene; 2,8-di-tert-butyl-5,6,11,12-tetrakis(4-(tert-butyl)phenyl)tetracene;

Green fluorescent emitter dopants can be selected, for example, from quinacridones, coumarin, and others, examples are: quinolino[2,3-b]acridine-7,14(5H,12H)-dione; 3,10-difluoroquinolino[2,3-b]acridine-7,14(5H,12H)-dione; 5,12-diphenylquinolino[2,3-b]acridine-7,14(5H,12H)-dione; 3-(benzo[d]oxazol-2-yl)-7-(diethylamino)-2H-chromen-2-one; 7-(diethylamino)-3-(4,6-dimethylbenzo[d]thiazol-2-yl)-2H-chromen-2-one; 10-(benzo[d]thiazol-2-yl)-1,1,7,7-tetramethyl-2,3,6,7-tetrahydro-1H-pyrano[2,3-f]pyrido[3,2,1-ij]quinolin-1 (5H)-one; 10-(4,6-di-tert-butylbenzo[d]thiazol-2-yl)-1,1,7,7-tetramethyl-2,3,6,7-tetrahydro-1H-pyrano[2,3-f]pyrido[3,2,1-ij]quinolin-11 (5H)-one.

Exemplary fluorescent blue emitter dopants are: 9-(naphthalen-1-yl)-10-(naphthalen-2-yl)anthracene; (Z)-6-mesityl-N-(6-mesitylquinolin-2(1H)-ylidene)quinolin-2-amine-BF2 complex; bis[2-[4-[N,N-diarylamino]phenyl]vinyl]biphenyl; 6,6'-(1,2-ethenediyl)bis(N-2-naphthalenyl-N-phenyl-2-naphthalenamine); 2,5,8,11-tetra-tert-butyl-1,10-dihydroperylene;

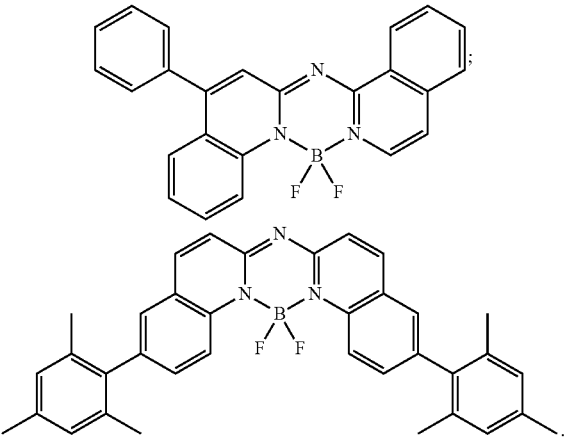

Suitable red phosphorescent emitter dopants are disclosed in US2011057559 on pages 33-35, table 1, titled "red dopants", which is incorporated herein by reference. Suitable green phosphorescent emitter dopants are disclosed in US2011057559 on pages 35-38, table 1, titled "green dopants", which is incorporated herein by reference. Suitable blue phosphorescent emitter dopants are disclosed in US2011057559 on pages 38-41, table 1, titled "blue dopants", and compounds from claim 30, which table and claim are incorporated herein by reference.

Suitable host materials for fluorescent emitters are, among others, anthracene derivatives substituted at the 9 and 10 positions, for example 9,10-di-(2-naphthyl)anthracene, 9-(1-naphthyl)-10-(2-naphthyl)-anthracene, compounds in US2005089717 A1, compounds AH1, AH2, AH3, AH4, AH5, AH6, AH7, AH8 as disclosed in pages 11-12 in US2008/0268282 A1.

Particular suitable host materials for red phosphorescent dopants are disclosed in US2011057559 on pages 28-29, table 1, titled "red host", which is incorporated herein by reference. Particular suitable host materials for green phosphorescent dopants are disclosed in US2011057559 on pages 29-32, table 1, titled "green host", which is incorporated herein by reference. Particular suitable host materials for blue phosphorescent dopants are disclosed in US2011057559 on pages 32-33, table 1, titled "blue host", which is incorporated herein by reference.

Many of the emitter dopants and hosts described above are commercially available, for example from Luminescence Technology Corp, TW.

Preferred structures of the compound according to formula (I) are depicted in Table 1:

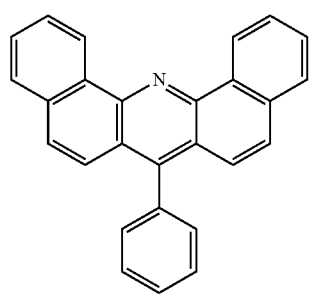 [SMILES: c1ccc(-c2c3ccc4ccccc4c3nc3c2ccc2ccccc23)cc1]

Structure 1

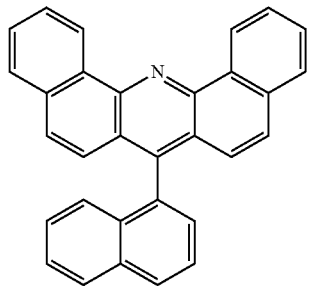 [SMILES: c1ccc2c(-c3c4ccc5ccccc5c4nc4c3ccc3ccccc34)cccc2c1]
Structure 2
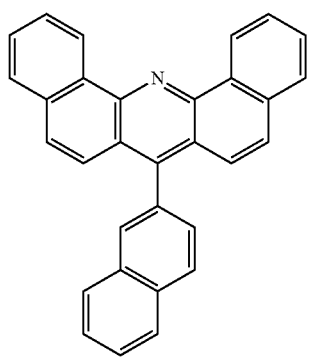 [SMILES: c1ccc2cc(-c3c4ccc5ccccc5c4nc4c3ccc3ccccc34)ccc2c1]
Structure 3
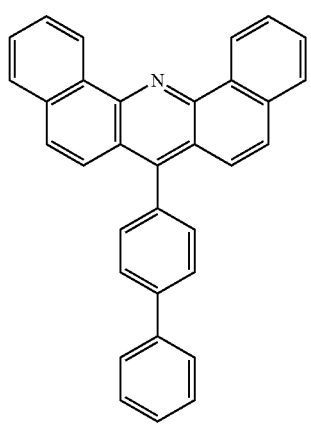 [SMILES: c1ccc(-c2ccc(-c3c4ccc5ccccc5c4nc4c3ccc3ccccc34)cc2)cc1]
Structure 4
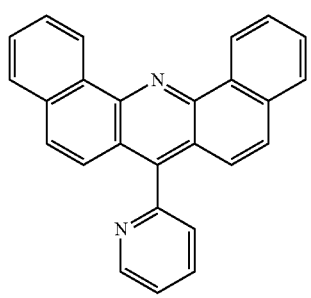 [SMILES: c1ccc(-c2c3ccc4ccccc4c3nc3c2ccc2ccccc23)nc1]
Structure 5

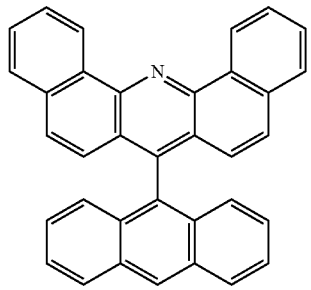 [SMILES: c1ccc2c(-c3c4ccc5ccccc5c4nc4c3ccc3ccccc34)c3ccccc3cc2c1]
Structure 6
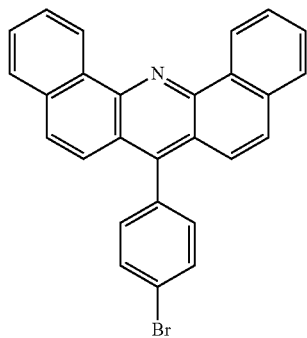 [SMILES: Brc1ccc(-c2c3ccc4ccccc4c3nc3c2ccc2ccccc23)cc1]
Structure 7
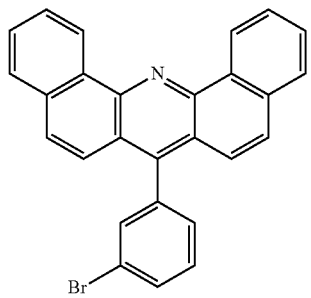 [SMILES: Brc1cccc(-c2c3ccc4ccccc4c3nc3c2ccc2ccccc23)c1]
Structure 8
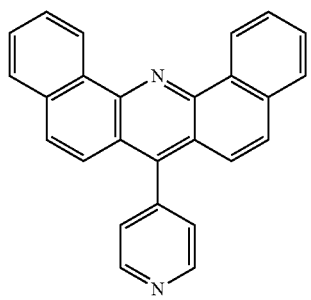 [SMILES: c1ccc2c(c1)ccc1c(-c3ccncc3)c3ccc4ccccc4c3nc12]
Structure 9
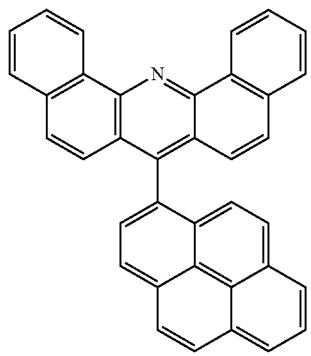 [SMILES: c1ccc2c(c1)ccc1c(-c3ccc4ccc5cccc6ccc3c4c56)c3ccc4ccccc4c3nc12]
Structure 10

-continued
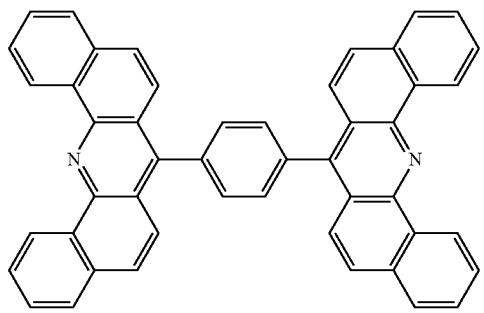 [SMILES: c1ccc2c(c1)ccc1c(-c3ccc(-c4c5ccc6ccccc6c5nc5c4ccc4ccccc45)cc3)c3ccc4ccccc4c3nc12]
Structure 11
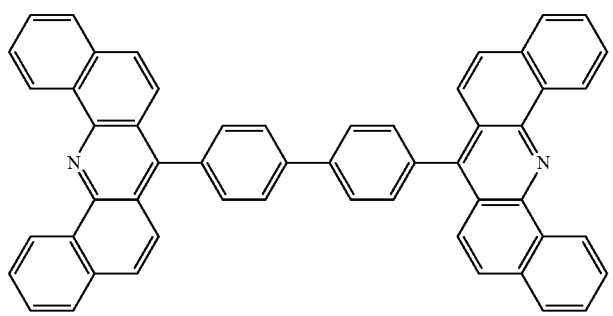 [SMILES: c1ccc2c(c1)ccc1c(-c3ccc(-c4ccc(-c5c6ccc7ccccc7c6nc6c5ccc5ccccc56)cc4)cc3)c3ccc4ccccc4c3nc12]
Structure 12
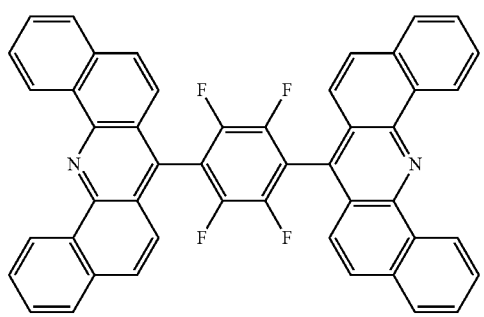 [SMILES: Fc1c(F)c(-c2c3ccc4ccccc4c3nc3c2ccc2ccccc23)c(F)c(F)c1-c1c2ccc3ccccc3c2nc2c1ccc1ccccc12]
Structure 13
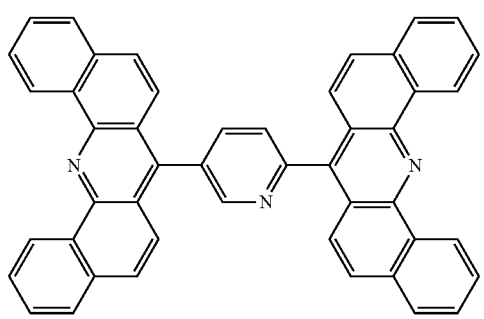 [SMILES: c1ccc2c(c1)ccc1c(-c3ccc(-c4c5ccc6ccccc6c5nc5c4ccc4ccccc45)nc3)c3ccc4ccccc4c3nc12]
Structure 14

Structure 16
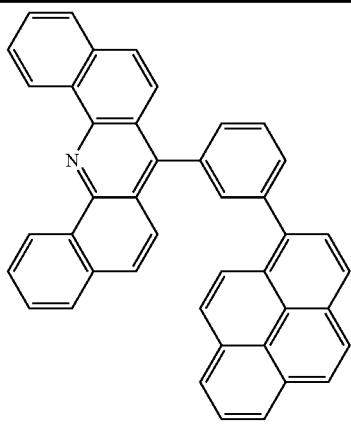
Structure 17
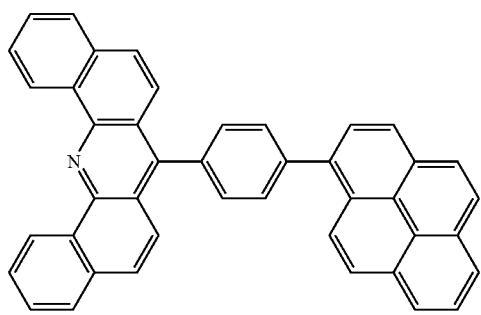 [SMILES: c1ccc2c(c1)ccc1c(-c3ccc(-c4ccc5ccc6cccc7ccc4c5c67)cc3)c3ccc4ccccc4c3nc12]
Structure 18
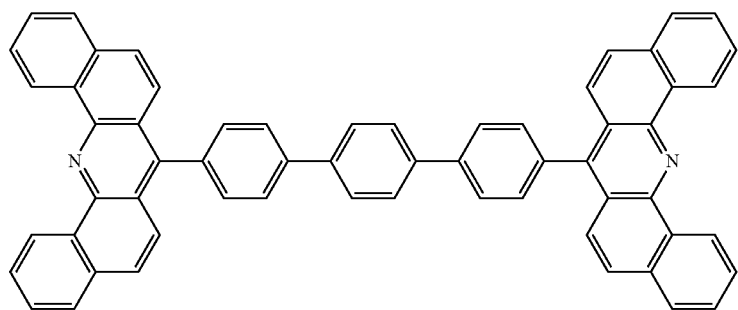 [SMILES: c1ccc2c(c1)ccc1c(-c3ccc(-c4ccc(-c5ccc(-c6c7ccc8ccccc8c7nc7c6ccc6ccccc67)cc5)cc4)cc3)c3ccc4ccccc4c3nc12]
Structure 19
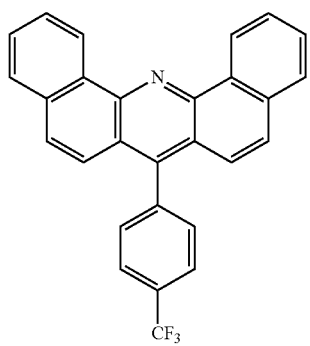 [SMILES: FC(F)(F)c1ccc(-c2c3ccc4ccccc4c3nc3c2ccc2ccccc23)cc1]

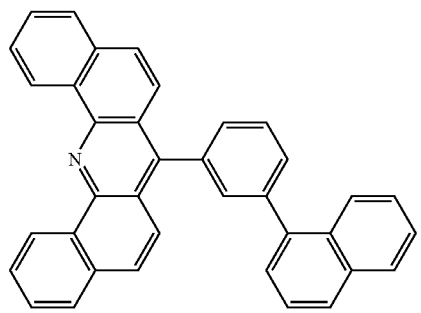 [SMILES: c1cc(-c2cccc3ccccc23)cc(-c2c3ccc4ccccc4c3nc3c2ccc2ccccc23)c1]
Structure 20
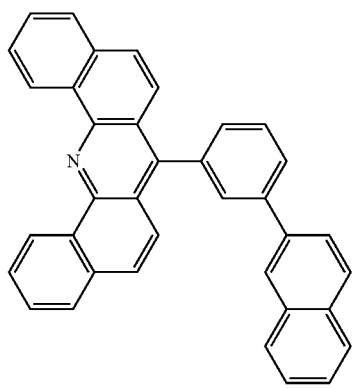 [SMILES: c1cc(-c2ccc3ccccc3c2)cc(-c2c3ccc4ccccc4c3nc3c2ccc2ccccc23)c1]
Structure 21
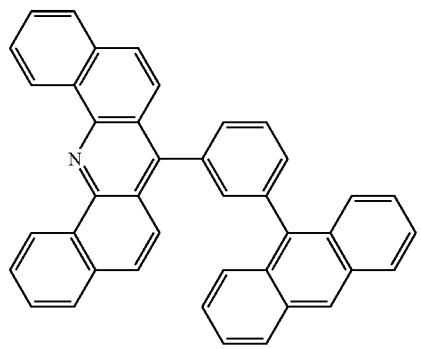 [SMILES: c1cc(-c2c3ccccc3cc3ccccc23)cc(-c2c3ccc4ccccc4c3nc3c2ccc2ccccc23)c1]
Structure 22
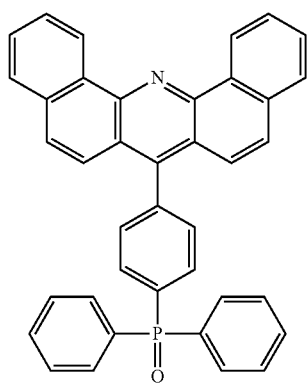 [SMILES: O=P(c1ccccc1)(c1ccccc1)c1ccc(-c2c3ccc4ccccc4c3nc3c2ccc2ccccc23)cc1]
Structure 23

-continued
Structure 24
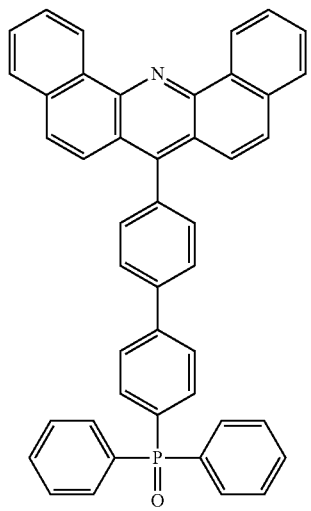 [SMILES: O=P(c1ccccc1)(c1ccccc1)c1ccc(-c2ccc(-c3c4ccc5ccccc5c4nc4c3ccc3ccccc34)cc2)cc1]
Structure 25
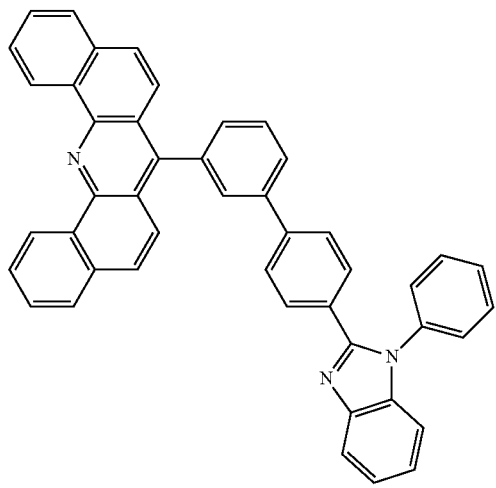 [SMILES: c1ccc(-n2c(-c3ccc(-c4cccc(-c5c6ccc7ccccc7c6nc6c5ccc5ccccc56)c4)cc3)nc3ccccc32)cc1]
Structure 26
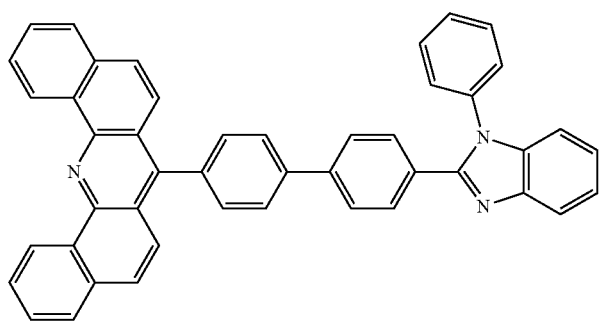 [SMILES: c1ccc(-n2c(-c3ccc(-c4ccc(-c5c6ccc7ccccc7c6nc6c5ccc5ccccc56)cc4)cc3)nc3ccccc32)cc1]
Structure 27
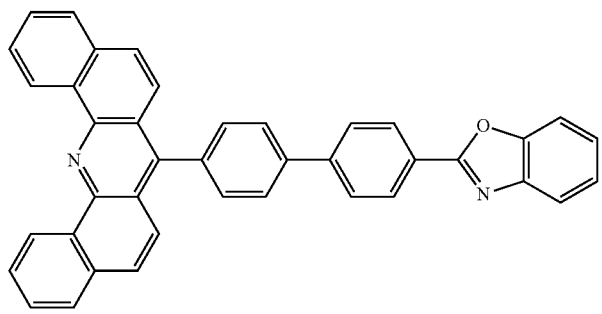 [SMILES: c1ccc2c(c1)ccc1c(-c3ccc(-c4ccc(-c5nc6ccccc6o5)cc4)cc3)c3ccc4ccccc4c3nc12]

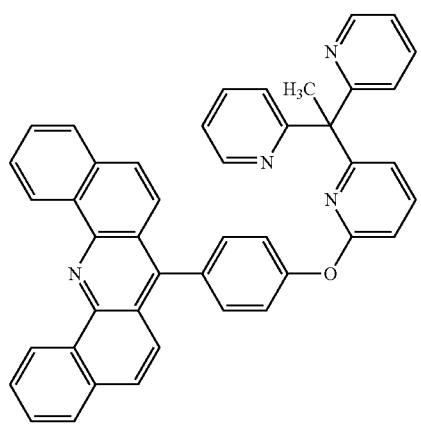 [SMILES: CC(c1ccccn1)(c1ccccn1)c1cccc(Oc2ccc(-c3c4ccc5ccccc5c4nc4c3ccc3ccccc34)cc2)n1]
Structure 28
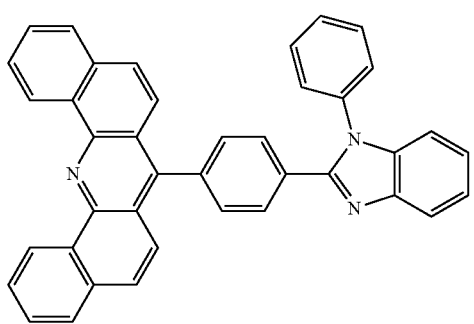 [SMILES: c1ccc(-n2c(-c3ccc(-c4c5ccc6ccccc6c5nc5c4ccc4ccccc45)cc3)nc3ccccc32)cc1]
Structure 29
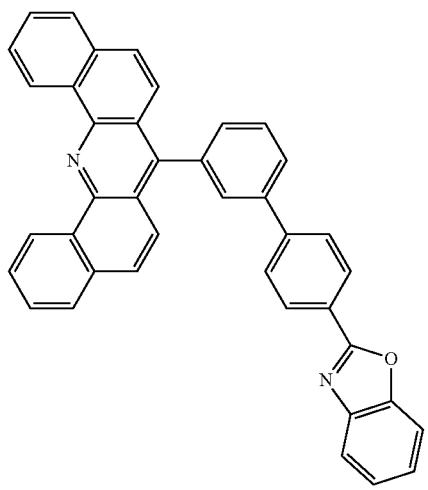 [SMILES: c1cc(-c2ccc(-c3nc4ccccc4o3)cc2)cc(-c2c3ccc4ccccc4c3nc3c2ccc2ccccc23)c1]
Structure 30
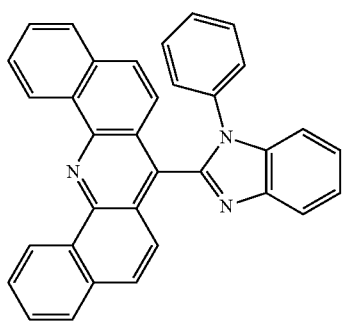 [SMILES: c1ccc(-n2c(-c3c4ccc5ccccc5c4nc4c3ccc3ccccc34)nc3ccccc32)cc1]
Structure 31

-continued
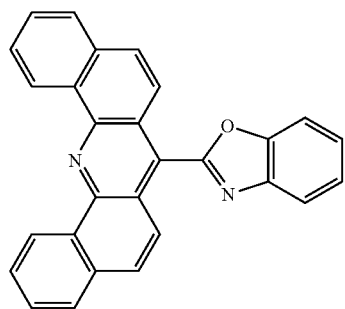 [SMILES: c1ccc2c(c1)ccc1c(-c3nc4ccccc4o3)c3ccc4ccccc4c3nc12]
Structure 32
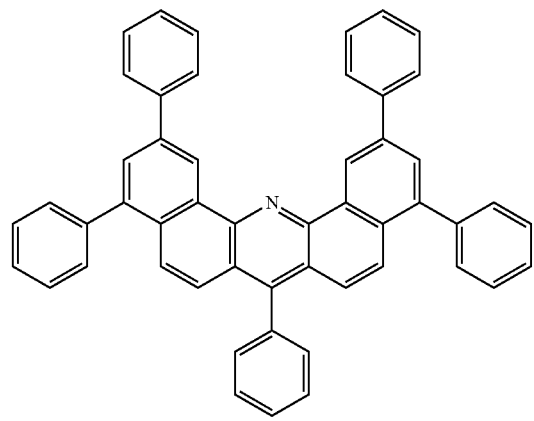 [SMILES: c1ccc(-c2cc(-c3ccccc3)c3ccc4c(-c5ccccc5)c5ccc6c(-c7ccccc7)cc(-c7ccccc7)cc6c5nc4c3c2)cc1]
Structure 33
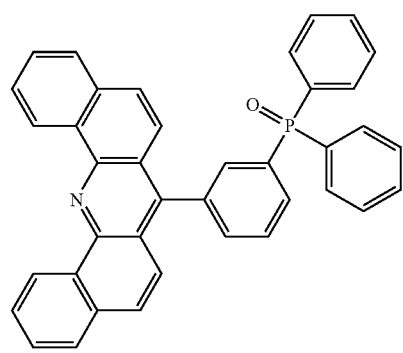 [SMILES: O=P(c1ccccc1)(c1ccccc1)c1cccc(-c2c3ccc4ccccc4c3nc3c2ccc2ccccc23)c1]
Structure 34
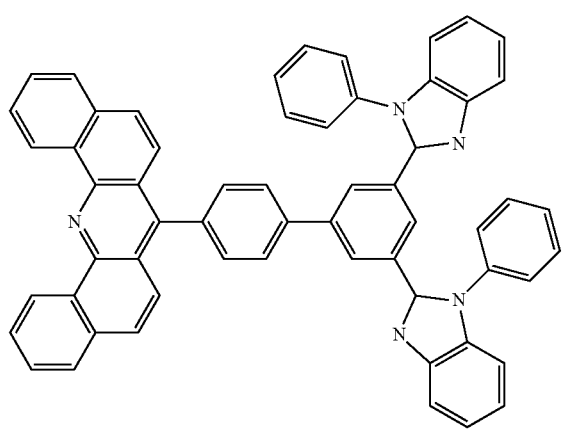 [SMILES: c1ccc(N2c3ccccc3NC2c2cc(-c3ccc(-c4c5ccc6ccccc6c5nc5c4ccc4ccccc45)cc3)cc(C3Nc4ccccc4N3c3ccccc3)c2)cc1]
Structure 35

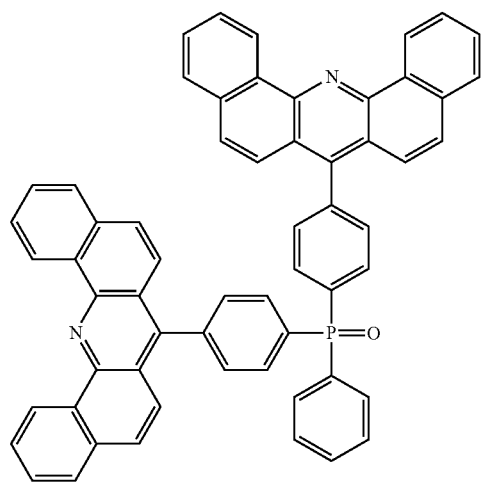 [SMILES: O=P(c1ccccc1)(c1ccc(-c2c3ccc4ccccc4c3nc3c2ccc2ccccc23)cc1)c1ccc(-c2c3ccc4ccccc4c3nc3c2ccc2ccccc23)cc1]
Structure 36
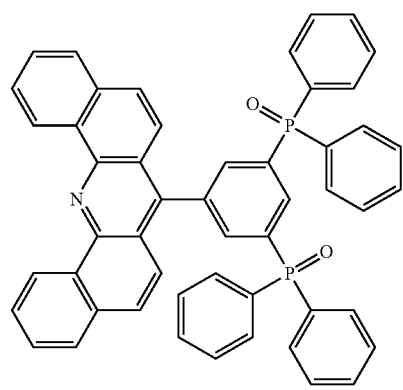 [SMILES: O=P(c1ccccc1)(c1ccccc1)c1cc(-c2c3ccc4ccccc4c3nc3c2ccc2ccccc23)cc(P(=O)(c2ccccc2)c2ccccc2)c1]
Structure 37
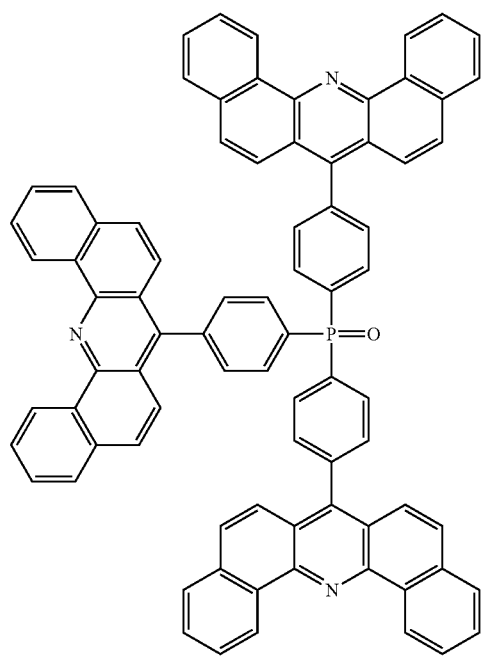 [SMILES: O=P(c1ccc(-c2c3ccc4ccccc4c3nc3c2ccc2ccccc23)cc1)(c1ccc(-c2c3ccc4ccccc4c3nc3c2ccc2ccccc23)cc1)c1ccc(-c2c3ccc4ccccc4c3nc3c2ccc2ccccc23)cc1]
Structure 38

Structure 39
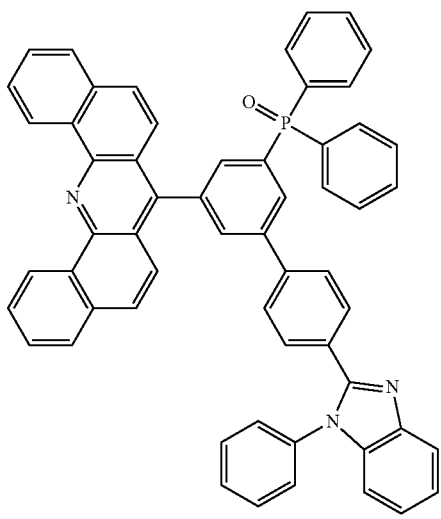 [SMILES: O=P(c1ccccc1)(c1ccccc1)c1cc(-c2ccc(-c3nc4ccccc4n3-c3ccccc3)cc2)cc(-c2c3ccc4ccccc4c3nc3c2ccc2ccccc23)c1]
Structure 40
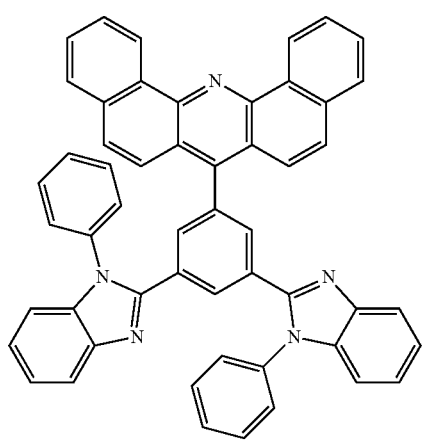 [SMILES: c1ccc(-n2c(-c3cc(-c4c5ccc6ccccc6c5nc5c4ccc4ccccc45)cc(-c4nc5ccccc5n4-c4ccccc4)c3)nc3ccccc32)cc1]
Structure 41
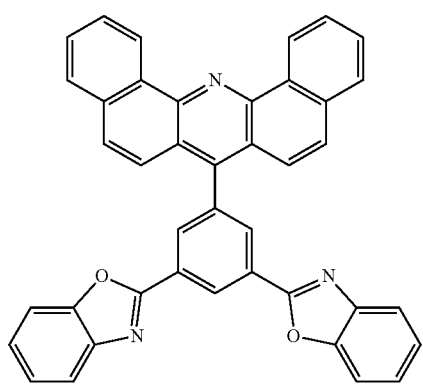 [SMILES: c1ccc2c(c1)ccc1c(-c3cc(-c4nc5ccccc5o4)cc(-c4nc5ccccc5o4)c3)c3ccc4ccccc4c3nc12]

-continued
Structure 42
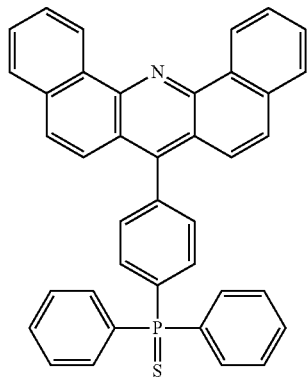 [SMILES: S=P(c1ccccc1)(c1ccccc1)c1ccc(-c2c3ccc4ccccc4c3nc3c2ccc2ccccc23)cc1]
Structure 43
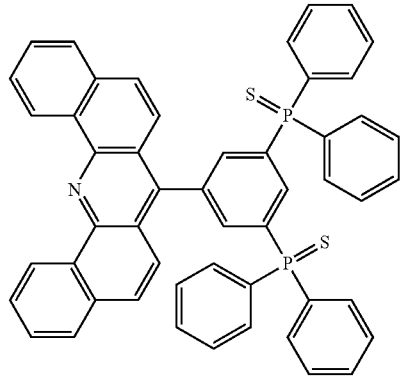 [SMILES: S=P(c1ccccc1)(c1ccccc1)c1cc(-c2c3ccc4ccccc4c3nc3c2ccc2ccccc23)cc(P(=S)(c2ccccc2)c2ccccc2)c1]
Structure 44
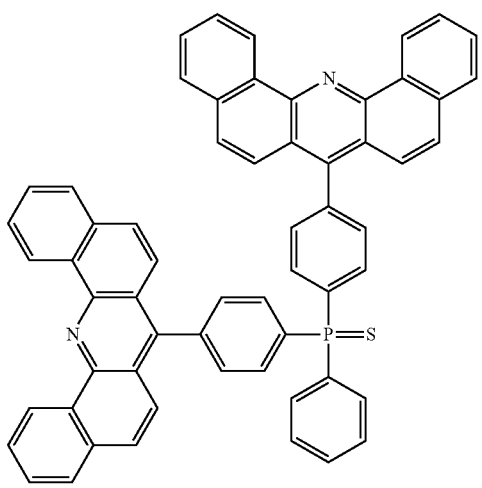 [SMILES: S=P(c1ccccc1)(c1ccc(-c2c3ccc4ccccc4c3nc3c2ccc2ccccc23)cc1)c1ccc(-c2c3ccc4ccccc4c3nc3c2ccc2ccccc23)cc1]
Structure 45
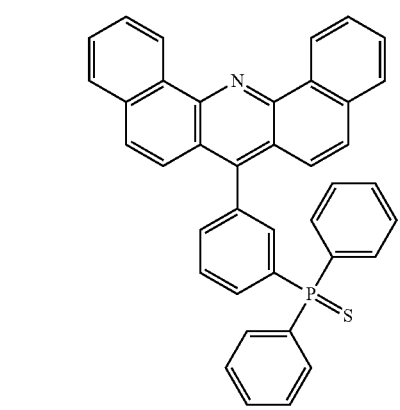 [SMILES: S=P(c1ccccc1)(c1ccccc1)c1cccc(-c2c3ccc4ccccc4c3nc3c2ccc2ccccc23)c1]

As can be taken from above table, Ar and R5 can be selected from a number of differently substituted or unsubstituted C6-C20-aryl or C5-C20-heteroaryl. Suitable substituents may be for example halogen, such as Br, aryl, pyrene, or CF3.
Also preferred are structures as illustrated in Table 2:
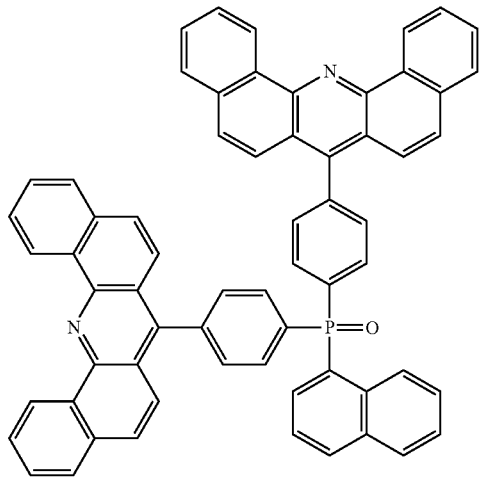 [SMILES: O=P(c1ccc(-c2c3ccc4ccccc4c3nc3c2ccc2ccccc23)cc1)(c1ccc(-c2c3ccc4ccccc4c3nc3c2ccc2ccccc23)cc1)c1cccc2ccccc12]
Structure 46
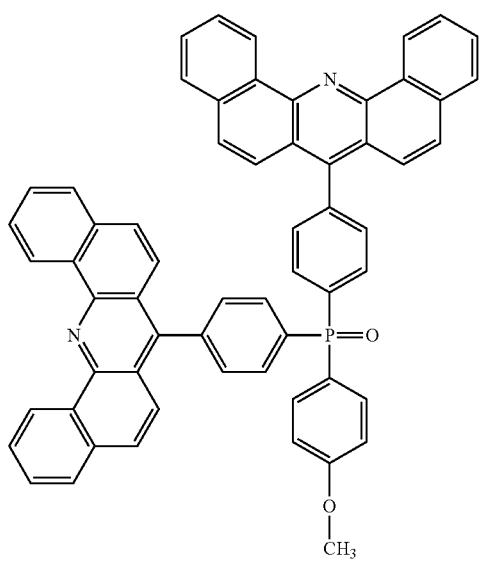 [SMILES: COc1ccc(P(=O)(c2ccc(-c3c4ccc5ccccc5c4nc4c3ccc3ccccc34)cc2)c2ccc(-c3c4ccc5ccccc5c4nc4c3ccc3ccccc34)cc2)cc1]
Structure 47
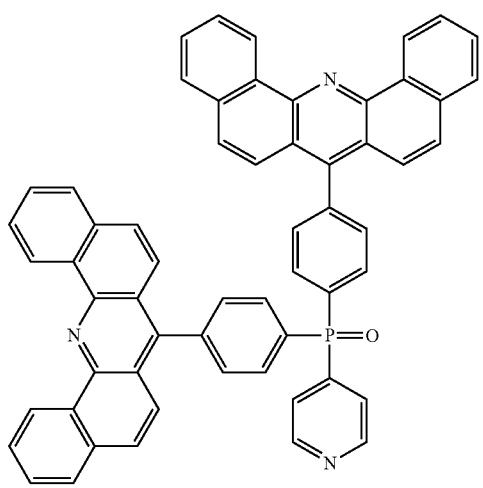 [SMILES: O=P(c1ccncc1)(c1ccc(-c2c3ccc4ccccc4c3nc3c2ccc2ccccc23)cc1)c1ccc(-c2c3ccc4ccccc4c3nc3c2ccc2ccccc23)cc1]
Structure 48

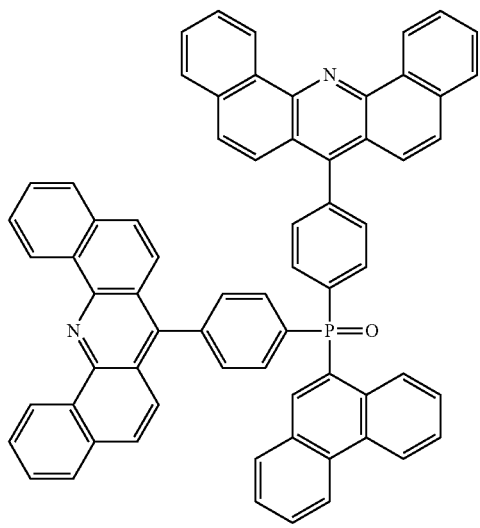 [SMILES: O=P(c1ccc(-c2c3ccc4ccccc4c3nc3c2ccc2ccccc23)cc1)(c1ccc(-c2c3ccc4ccccc4c3nc3c2ccc2ccccc23)cc1)c1cc2ccccc2c2ccccc12]
Structure 49
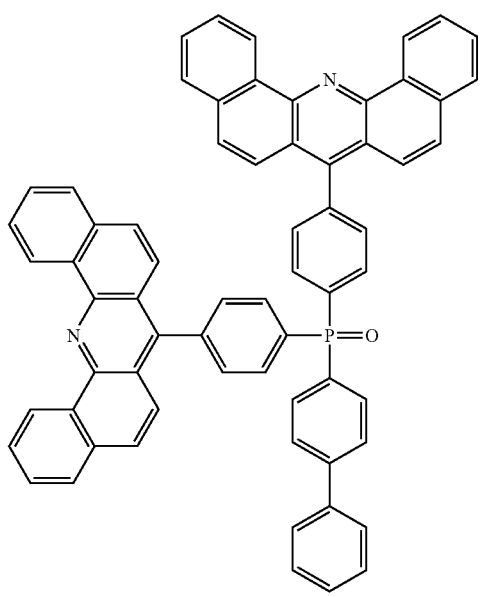 [SMILES: O=P(c1ccc(-c2ccccc2)cc1)(c1ccc(-c2c3ccc4ccccc4c3nc3c2ccc2ccccc23)cc1)c1ccc(-c2c3ccc4ccccc4c3nc3c2ccc2ccccc23)cc1]
Structure 50

-continued
Structure 51
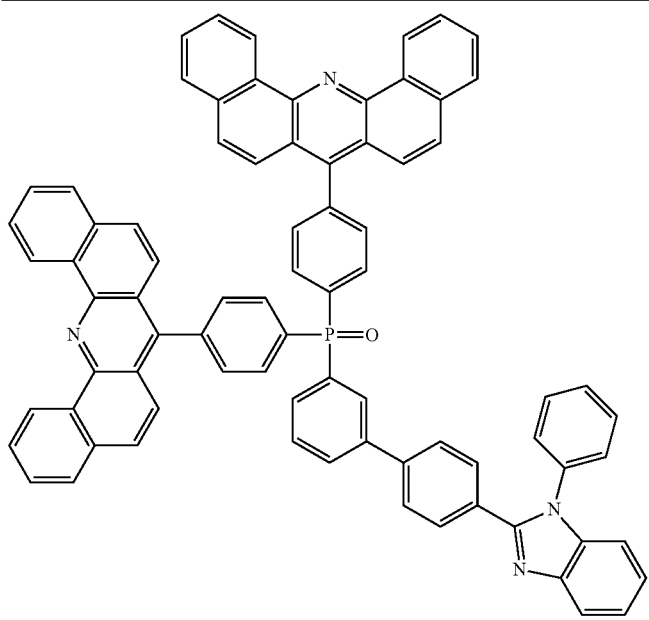
Structure 52
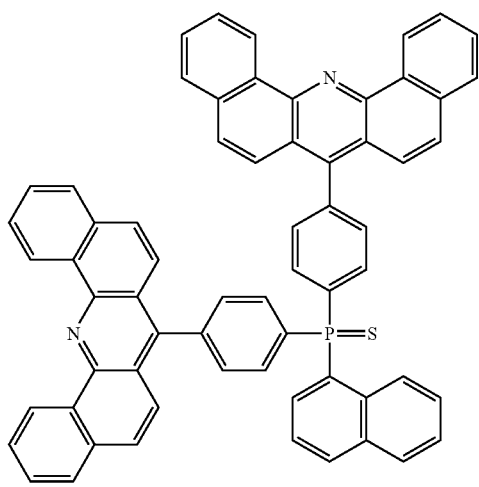 [SMILES: S=P(c1ccc(-c2c3ccc4ccccc4c3nc3c2ccc2ccccc23)cc1)(c1ccc(-c2c3ccc4ccccc4c3nc3c2ccc2ccccc23)cc1)c1cccc2ccccc12]
Structure 53
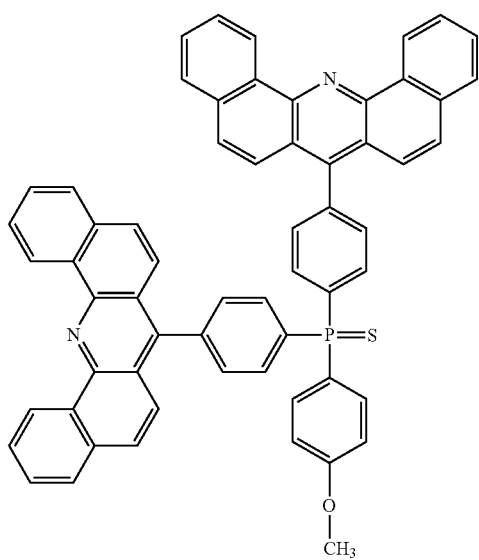 [SMILES: COc1ccc(P(=S)(c2ccc(-c3c4ccc5ccccc5c4nc4c3ccc3ccccc34)cc2)c2ccc(-c3c4ccc5ccccc5c4nc4c3ccc3ccccc34)cc2)cc1]

-continued
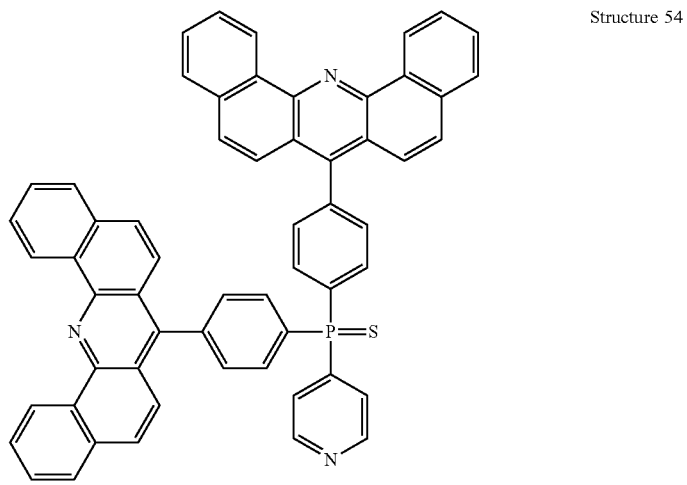
Structure 54
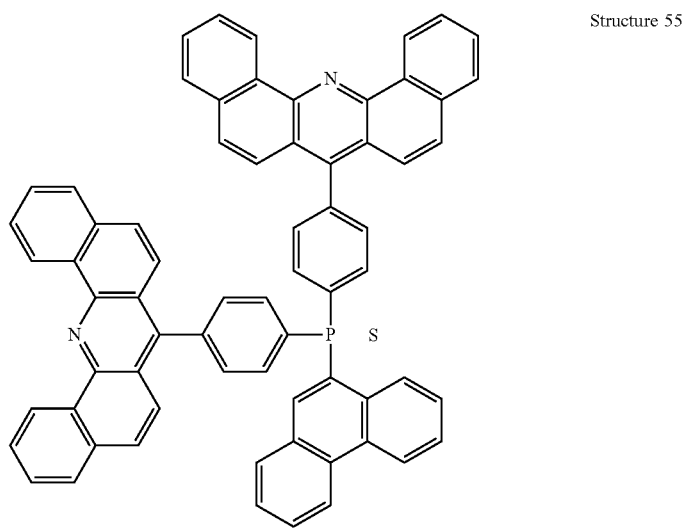
Structure 55
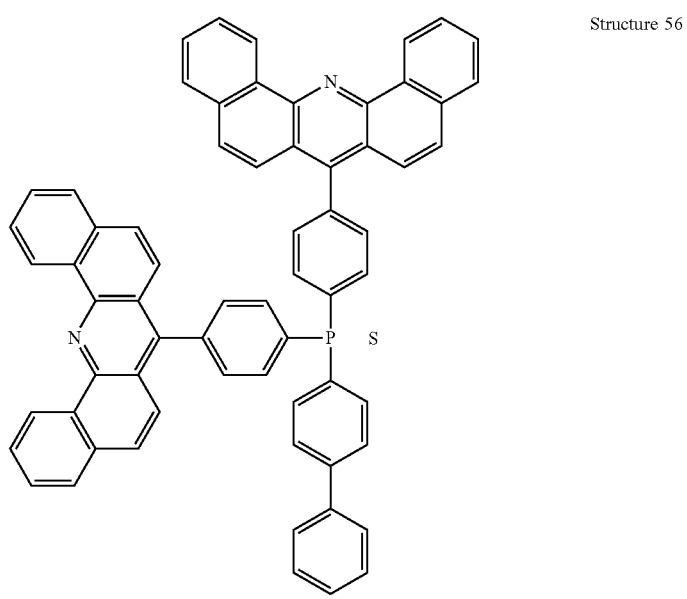
Structure 56

-continued
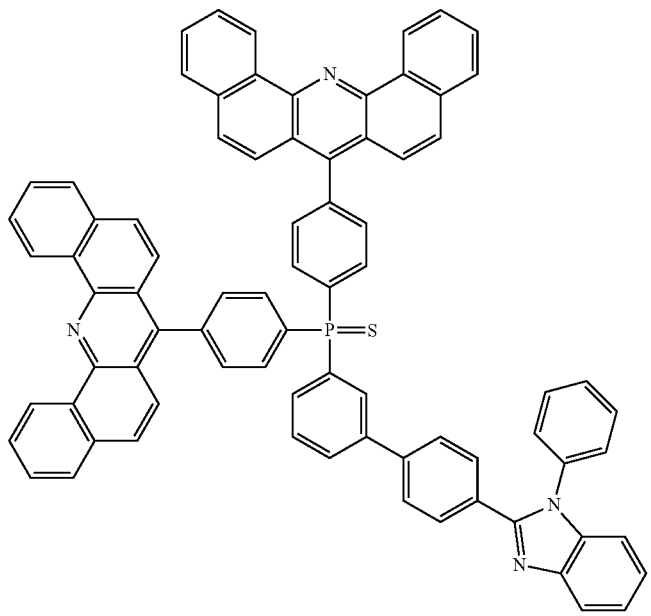
Structure 57
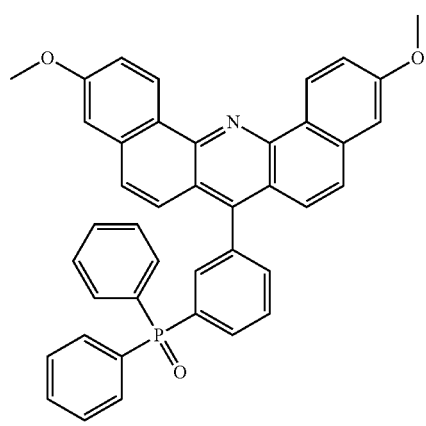
Structure 58
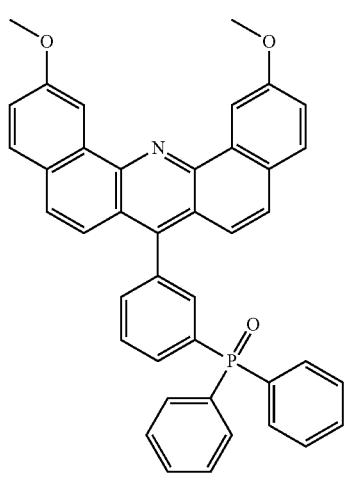 [SMILES: COc1ccc2ccc3c(-c4cccc(P(=O)(c5ccccc5)c5ccccc5)c4)c4ccc5ccc(OC)cc5c4nc3c2c1]
Structure 59

General Synthesis Method

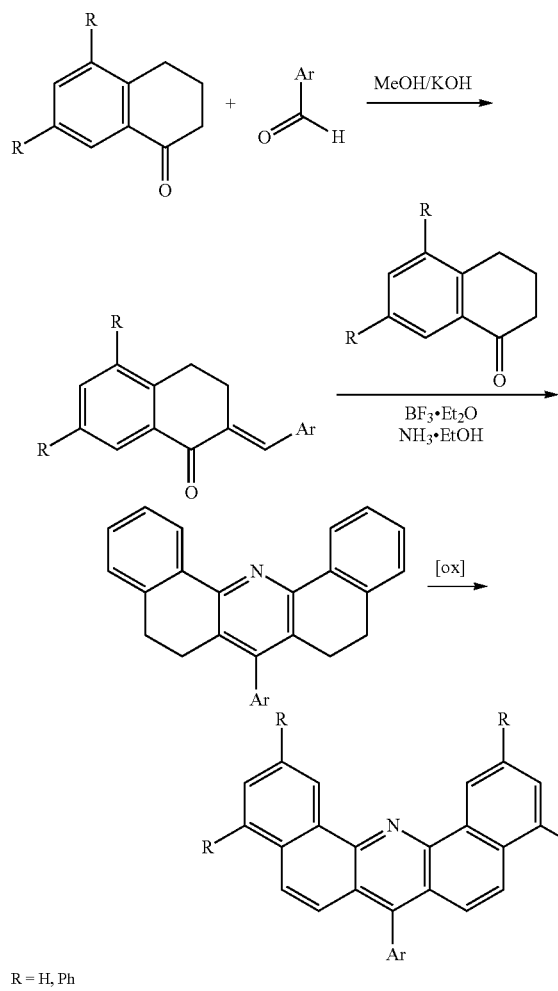

R = H, Ph

Of course, the R's in the above general synthesis scheme shall stand for R1-4 according to formula (I). Additionally, Ar shall in this general synthesis scheme be understood to stand for the moiety "A3" according to formula (I).

R1-4 are independently introduced in steps 1 and/or 2 of the general synthesis scheme by choosing the proper tetralone derivative (such as 6-fluoro-3,4-dihydro-7-methoxy-1 (2H)-naphthalenone or 3,4-dihydro-5,8-dimethyl-1(2H)-naphthalenone, or 6,7-dichloro-3,4-dihydro 1(2H)-naphthalenone, or, 3,4-dihydro-6-nitro-1(2H)-naphthalenone, or 3,4-dihydro-7-phenyl-1(2H)-naphthalenone which are all commercial materials.

Preferred Additional Materials
Donors as Electrical (Redox) Dopants

In one mode of the invention, the IETL is doped with n-dopants which are strong donors or donor precursors. Typical n-dopants are: alkaline metals like Li or Cs or alkaline earth metals like Ba, tetrathianaphtacene, [Ru (terpy)2]0; rhodamine B; pyronin B chloride; acridine orange base; leuco crystal violet; 2,2'-diisopropyl-1,1',3,3'-tetramethyl-2,2',3,3',4,4',5,5',6,6',7,7'-dodecahydro-1H, 1'H-2,2-bibenzo[d]imidazole; 4,4',5,5'-tetracyclohexyl-1,1',2,2',3,3'-hexamethyl-2,2',3,3'-tetrahydro-1H,1'H-2,2'-bisimidazole (NDOPI); 2,2'-diisopropyl-4,4',5,5'-tetrakis(4-methoxyphenyl)-1,1',3,3'-tetramethyl-2,2',3,3'-tetrahydro-1H,1'H-2,2'-bisimidazole; 2-isopropyl-1,3-dimethyl-2,3,6,7-tetrahydro-1H-5,8-dioxa-1,3-diaza-cyclopenta[b]-naphthene; bis-[1,3-dimethyl-2-isopropyl-1,2-dihydro benzimidazolyl-(2)]; tetrakis(1,3,4,6,7,8-hexahydro-2H-pyrimido[1,2-a]pyrimidinato) ditungsten(II) (W2(hpp)4); 2,2'-diisopropyl-4,5-bis(2-methoxyphenyl)-4',5'-bis(4-methoxyphenyl)-1,1',3,3'-tetramethyl-2,2',3,3'-tetrahydro-1H,1'H-2,2'-bisimidazole; 2,2'-diisopropyl-4,5-bis(2-methoxyphenyl)-4',5'-bis(3-methoxyphenyl)-1,1',3,3'-tetramethyl-2,2',3,3'-tetrahydro-1H, 1'H-2,2'-bisimidazole (see for example, patent publications US 2005/0040390, US 2009/0212280, and US 2007/0252140).

The molar ratio of the used redox dopant or its precursor to the doped matrix is usually less than 1:1, so that there is no excess n-dopant in the layer (the ":" can be read as a division sign, so that "less" means a smaller value. Preferably the doping ratio is less than 1:4, more preferably less than 1:10 and more than 1:10 000.

Alternatively, the IETL comprises a metal salt like cesium carbonate or cesium phosphate or a metal complex according to Formula III.

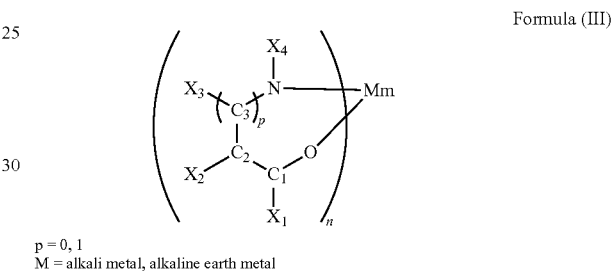

Formula (III)

p = 0, 1
M = alkali metal, alkaline earth metal wherein C1, C2 and C3 are carbon atoms and X1-X4 in formula (III) are independently selected from H, heteroatom, C1-C20-alkyl or branched C4-C20-alkyl, C3-C20-cycloalkyl, alkenyl with C1-C20, alkinyl with C1-C20, aryl or heteroaryl, wherein m and n are integers independently selected to provide a neutral charge on the complex, wherein X1-C1-C2-X2, and X3-C3-N—X4 are at the same time or independently from each other part of a fused or nonfused saturated, nonsaturated, aromatic or heteroaromatic cyclic or polycyclic system, preferably is p=0 and X1-C1-C2-X2 and X2-C2-N—X4 are part of a substituted or unsubstituted quinoline structure. Most preferably, the metal complex is lithium 8-hydroxyquinolinolate known also as lithium quinolate or LiQ.

Further preferred, the additional electron injecting material can be selected from:

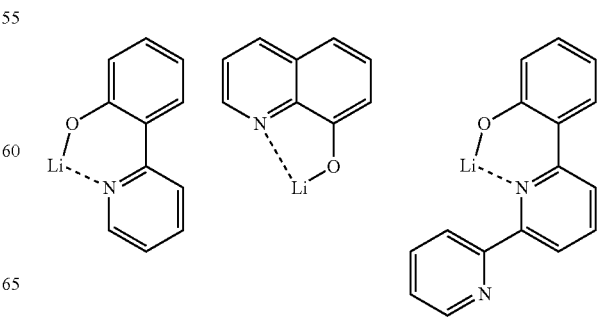

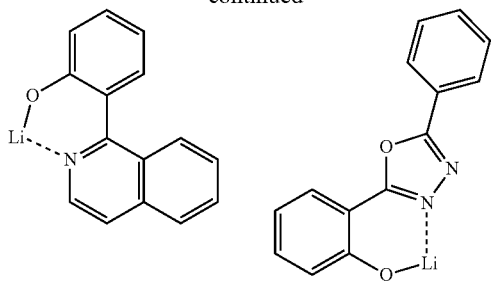

Also preferred are 2,3-diphenyl-5-hydroxyquinoxalinolato lithium, cesium quinolate, potassium quinolate, rubidium quinolate. Additional information of such materials can be found in Jpn. J. Appl. Phys. 45 (2006) pp. L1253-L1255; Liang, Journal of Materials Chemistry v. 13, pp. 2922-2926 (2003); Pu et al, 10, pp-228-232, Organic Electronics (2009).

It is preferred that the weight ratio of metal salt or metal complex:IETM in the layer is 1:1 or less.

EXAMPLES

Example 1

Synthesis of

Structure 1

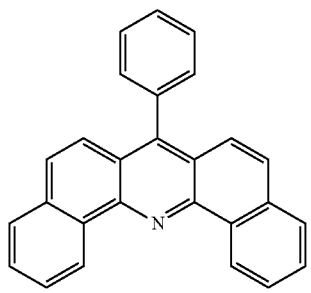

First step: Synthesis of 2-benzylidene-3,4-dihydronaphthalen-1(2H)-one (a). All manipulations were carried out in air, without any further purification of commercial solvents/chemicals.

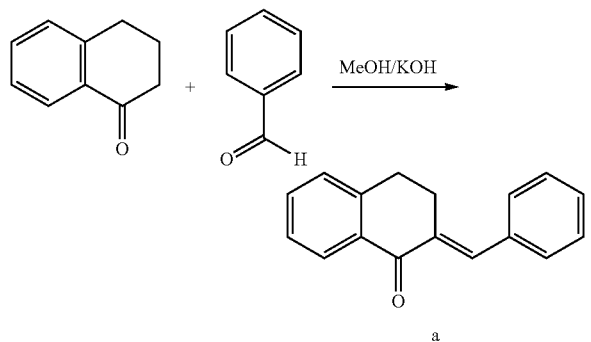

A 250 mL flask was charged with tetralone (4 g, 27.4 mmol) and benzaldehyde (3.88 g, 36.6 mmol). This was dissolved in warm tetrahydrofuran (THF, 15 mL), and to this yellow solution was slowly added a 4 wt % solution KOH in methanol (125 mL). The reaction was stirred for 4 days at room temperature. The solvent was then removed under reduced pressure, the residue was poured into 150 mL water and extracted with methylene chloride (DCM). The organic extract was dried over magnesium sulfate and filtered, and the solvent was removed at reduced pressure to afford 4.1 g white powder (64% of the theoretical yield, based on tetralone).

NMR: 1H NMR (500 MHz, CD2Cl2) δ 8.01 (dd, J=64.7, 65.4, 2H), 7.71-6.92 (m, 8H), 3.39-2.64 (m, 4H).

Second step: Synthesis of 7-phenyl-5,6,8,9-tetrahydrodibenzo[c,h]acridine (b). Both reaction steps were carried out under argon.

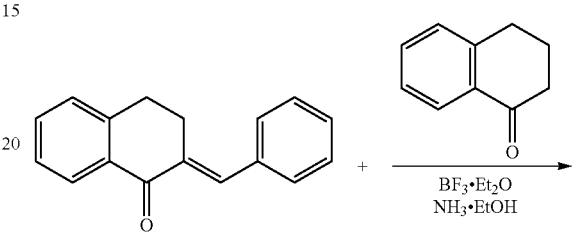

a (2.9 g, 12.4 mmol) and tetralone (1.7 g, 11.6 mmol) were introduced in a flask together with BF$_3$.Et$_2$O (1.8 mL, 14.2 mmol). The mixture was stirred at 100° C. for 4 hours and cooled down to room temperature. Et$_2$O was added (15 mL) and the mixture was stirred for an additional hour. The precipitate was filtered and washed with Et$_2$O (15 mL). The dried powder (1.9 g) was then introduced at 0° C. in a flask together with a ammonia-ethanol solution. The mixture was allowed to stir at room temperature for 6 h, the solid was filtered and washed several times with ethanol. 1.4 g white powder was obtained (34% yield).

Third step: Synthesis of 7-phenyldibenzo[c,h]acridine (1). The oxidative dehydrogenation was carried out under argon with dry solvents.

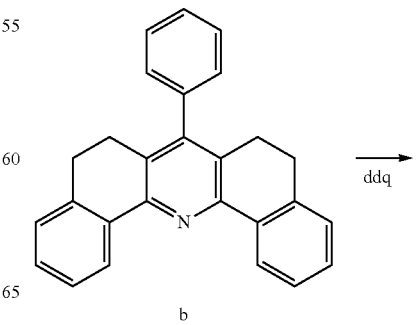

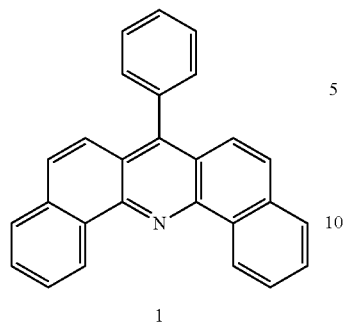

1 b (1.55 g, 4.31 mmol) was dissolved in 100 mL dioxane and 2,3-dichloro-5,6-dicyanobenzoquinone was added (6.88 g, 30.3 mmol). The mixture was refluxed under argon for 2 days. The reaction mixture was then cooled to room temperature, poured in 300 mL saturated aqueous sodium carbonate solution and stirred at 65° C. for 30 min. The mixture was then cooled to room temperature; the precipitation was filtered and washed with water and methylene chloride. Yield: 1.1 g (72%).

$^1$H NMR (500 MHz, CD2Cl2) δ 8.02-7.94 (m, 4H), 7.86 (dd, J=1.2, 7.8, 2H), 7.71 (ddd, J=5.9, 11.0, 25.9, 3H), 7.45 (dd, J=7.3, 8.4, 4H), 7.20 (d, J=8.7, 2H), 7.05 (ddd, J=1.5, 7.0, 8.6, 2H).

Example 2

Synthesis of

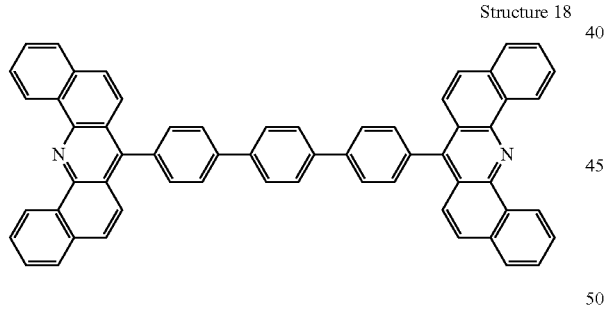

Structure 18

First step: Synthesis of (E)-2-(4-bromobenzylidene)-3,4-dihydronaphthalen-1(2H)-one (c). All manipulations were carried out in air, without any further purification of commercial solvents/chemicals.

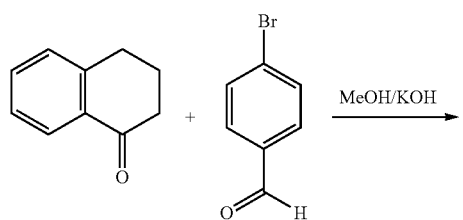

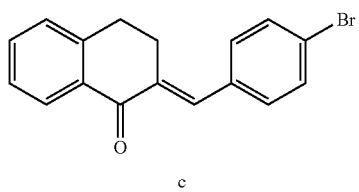

c

A 250 mL flask was charged with tetralone (3.22 g, 22 mmol) and 4-bromobenzaldehyde (5.3 g, 28.6 mmol). This was dissolved in warm tetrahydrofuran (12 mL), and to this yellow solution was slowly added a 4 wt % solution of KOH in methanol (100 mL). The reaction was stirred for 4 days at room temperature. The mixture was concentrated and reduced to approx 10% vol. The residue was filtered and washed with methyl-tert-butylether (MTBE, 3*50 mL), dried, to afford a light yellow powder (6.61 g, 96%).

Second step: Synthesis of 7-(4-bromophenyl)-5,6,8,9-tetrahydrodibenzo[c,h]acridine (d). Both reaction steps were carried out under argon.

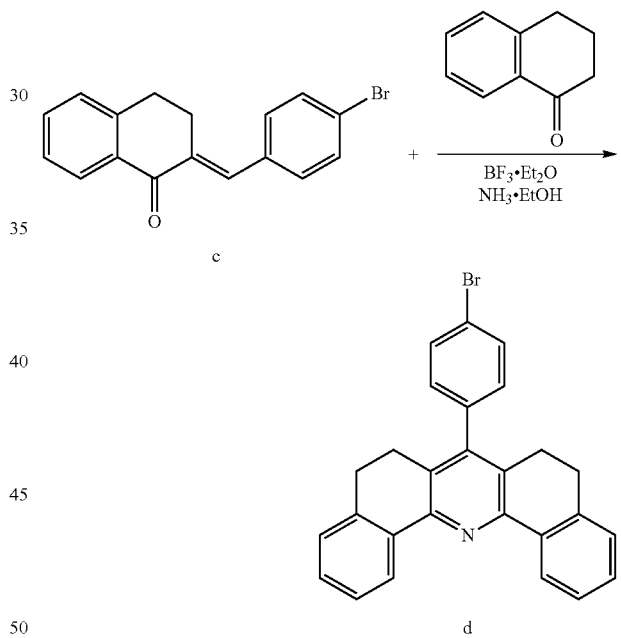

c (6.54 g, 20.9 mmol) and tetralone (2.93 g, 20.0 mmol) were introduced in a flask together with BF$_3$.Et$_2$O (3 mL, 23.7 mmol). The mixture is stirred at 100° C. for 4 hours and cooled to room temperature. Et$_2$O was added (25 mL) and the mixture is stirred for an additional hour. The precipitate is filtered and washed with Et$_2$O (20 mL). The dried powder (3.8 g) was then introduced at 0° C. in a flask together with an ammonia-ethanol solution. The mixture was allowed to stir at room temperature for 5 h, the precipitate was filtered and washed several times with ethanol.

2.98 g (34% yield) white powder was obtained.

Third step: Synthesis of 7-(4-bromophenyl)dibenzo[c,h]acridine (7). The oxidative dehydrogenation was carried out under argon.

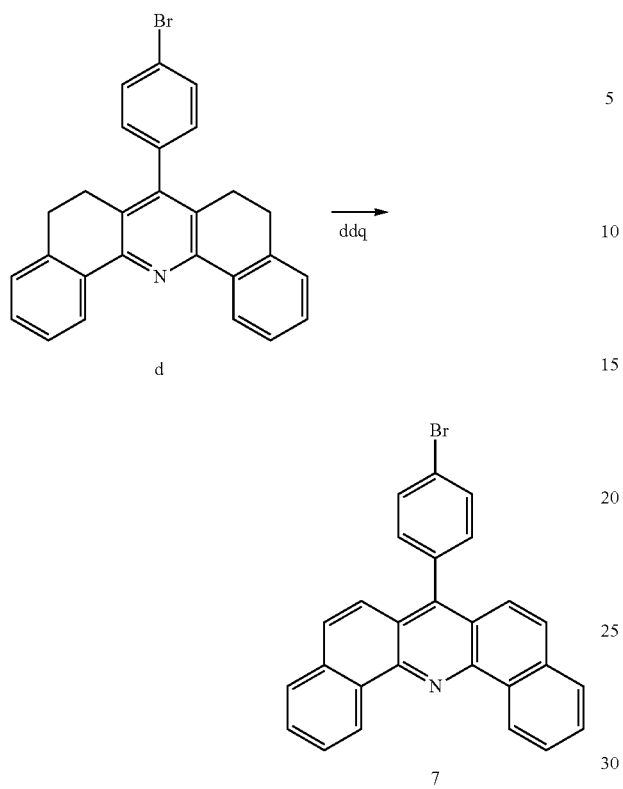

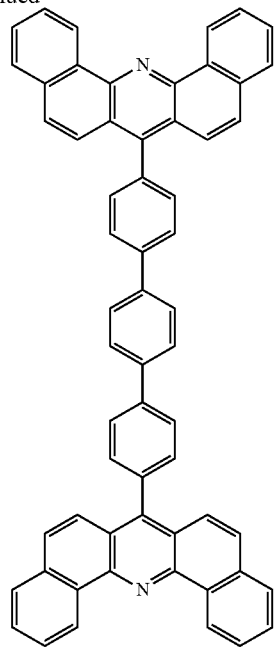

Structure 18

(7) (700 mg, 1.61 mmol), 1,4-phenylenediboronic acid (146 mg, 0.88 mmol), palladium tetrakis triphenylphoshine (186 mg, 0.16 mmol) and potassium carbonate (1.34 g, 9.66 mmol) were introduced in a flask together with 17 mL toluene, 8.8 mL ethanol and 2.6 mL distilled water. This mixture was stirred at 80° C. during 24 hours before being filtered. The solid was then washed with hexane, water and several mL chloroform before being dried.

Yield: 200 mg (20%).

Example 3

Synthesis of

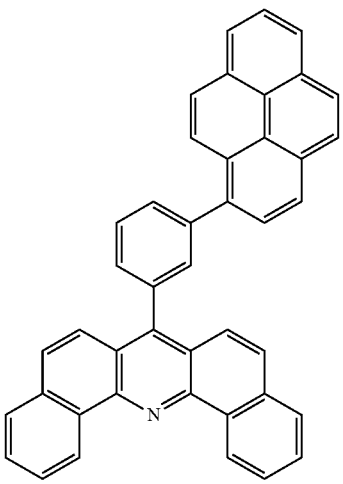

Structure 16 d (2.98 g, 6.80 mmol) was dissolved in 190 mL dioxane and 2,3-dichloro-5,6-dicyanobenzoquinone was added (10.9 g, 48 mmol). The mixture was refluxed under argon for 2 days. The reaction mixture was then cooled to room temperature, poured in 600 mL saturated aqueous sodium carbonate solution and stirred at 65° C. for 30 min. The mixture was then cooled to room temperature, the precipitation was filtered and washed with water and dichloromethane.

Yield: 2 g (68%). $^1$H NMR (500 MHz, CD$_2$Cl$_2$) δ (ppm): 9.80 (d, J=8.0, 2H), 8.00-7.68 (m, 10H), 7.53 (d, J=9.2, 2H), 7.45-7.34 (m, 2H).

Fourth step: Synthesis of 4,4''-bis(dibenzo[c,h]acridin-7-yl)-1,1':4',1''-terphenyl (18). The Pd catalyzed reaction was carried out under argon, without any further purification of commercial solvents/chemicals.

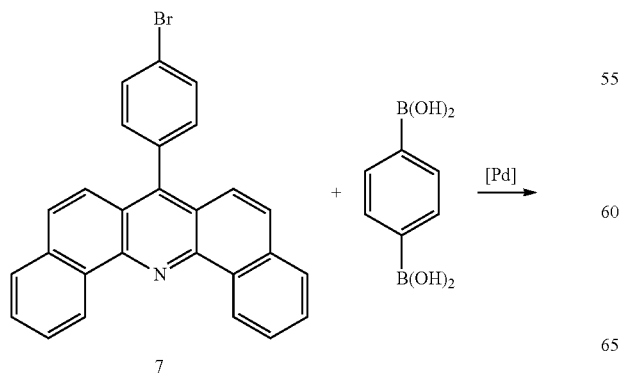

First step: Synthesis of (E)-2-(3-bromobenzylidene)-3,4-dihydronaphthalen-1(2H)-one (e). All manipulations were carried out in air, without any further purification of commercial solvents/chemicals.

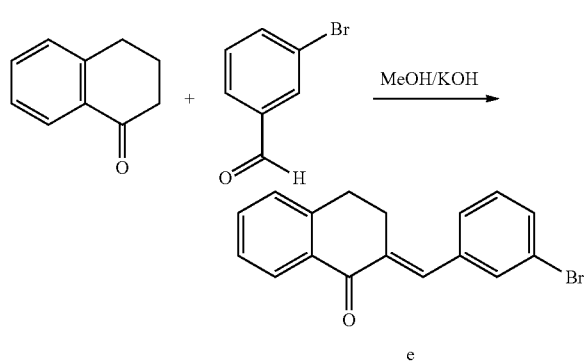

A 250 mL flask was charged with tetralone (5.2 g, 35.6 mmol) and 3-bromobenzaldehyde (8.51 g, 56 mmol). This was dissolved in warm tetrahydrofuran (20 mL), and to this yellow solution 4 wt % solution of KOH in methanol (160 mL) was slowly added. The reaction was stirred for 4 days at room temperature. The mixture was concentrated and reduced to approx 10% vol. The residue was filtered and washed with MTBE (3*50 mL), dried, to afford a light yellow powder (10.3 g, 92%).

NMR: $^1$H NMR (500 MHz, $CD_2Cl_2$) δ 8.01 (dd, J=64.7, 65.4, 2H), 7.71-6.92 (m, 8H), 3.39-2.64 (m, 4H).

Second step: Synthesis of 7-(3-bromophenyl)-5,6,8,9-tetrahydrodibenzo[c,h]acridine (f). Both reaction steps were carried out under argon.

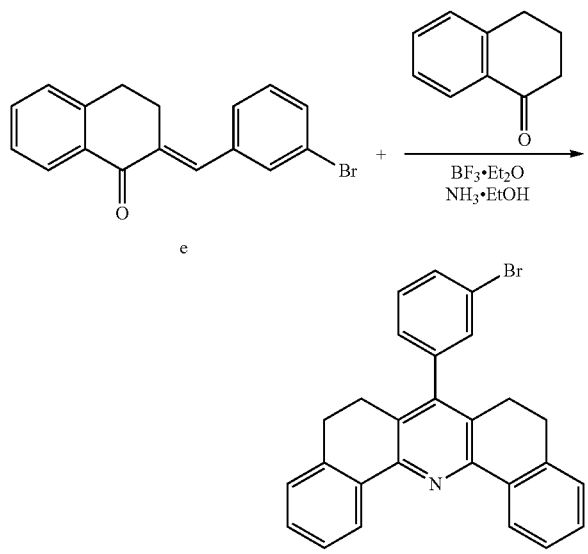

e (10.2 g, 32.6 mmol) and tetralone (4.52 g, 30.9 mmol) were introduced in a flask together with $BF_3 \cdot Et_2O$ (4.7 mL, 37.1 mmol). The mixture was stirred at 100° C. for 4 hours and cooled to room temperature. $Et_2O$ was added (70 mL) and the mixture was stirred for an additional hour. The precipitate was filtered and washed with $Et_2O$ (20 mL). The dried powder (5.6 g) was then introduced at 0° C. in a flask together with an ammonia-ethanol solution. The mixture was allowed to stir at room temperature for 5 h, the solid was filtered and washed several times with ethanol.

4.5 g (33% yield) white powder was obtained.

Third step: Synthesis of 7-(3-bromophenyl)dibenzo[c,h] acridine (8). The oxidative dehydrogenation was carried out under argon.

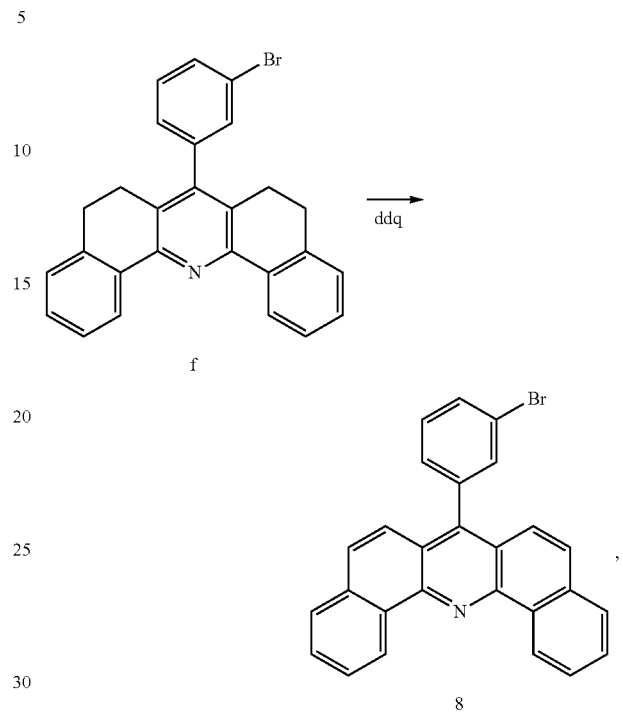

f (4.49 g, 10.2 mmol) was dissolved in 220 mL dioxane and 2,3-dichloro-5,6-dicyanobenzoquinone was added (14.3 g, 63 mmol). The mixture was refluxed under argon for 2 days. The reaction mixture was then cooled to room temperature, poured in 700 mL saturated aqueous sodium carbonate solution and stirred at 65° C. for 30 min. The mixture was then cooled to room temperature; the solid precipitate was filtered and washed with water and dichloromethane.

Yield: 3.3 g (74%).

$^1$H NMR (500 MHz, $CD_2Cl_2$) δ (ppm): 9.80 (d, J=8.1, 2H), 8.01-7.63 (m, 11H), 7.61-7.40 (m, 4H).

Fourth step: Synthesis of 7-(3-(pyren-1-yl)phenyl) dibenzo[c,h]acridine (16). The Pd catalyzed reaction was carried out under argon.

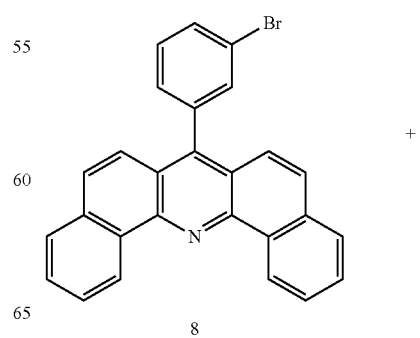

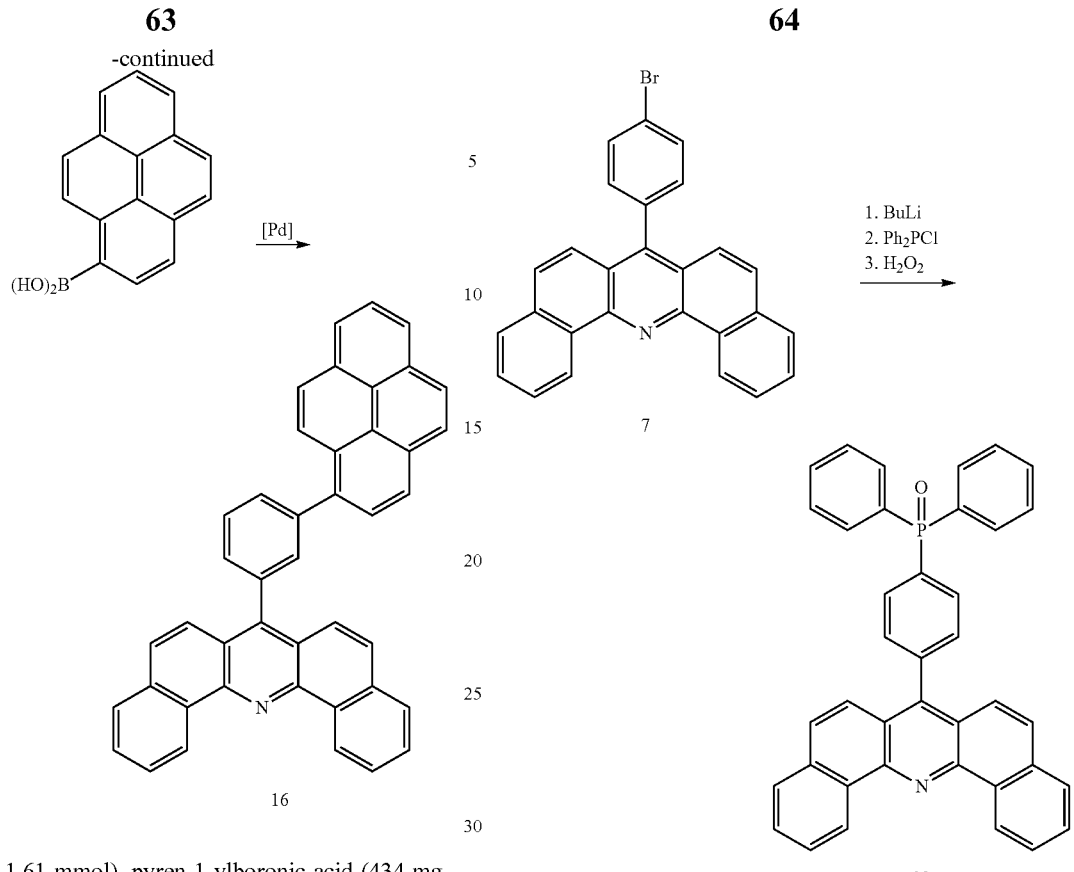

(8) (700 mg, 1.61 mmol), pyren-1-ylboronic acid (434 mg, 1.76 mmol), palladium tetrakis triphenylphoshine (186 mg, 0.16 mmol) and potassium carbonate (1.34 g, 9.66 mmol) were introduced in a flask together with 17 mL toluene, 8.8 mL ethanol and 2.6 mL distilled water. This mixture was stirred at 80° C. during 24 hours before being filtered. The solid was then washed with hexane, water and several mL of chloroform before being dried.

Yield: 392 mg (44%).

Example 4

Synthesis of

Structure 23

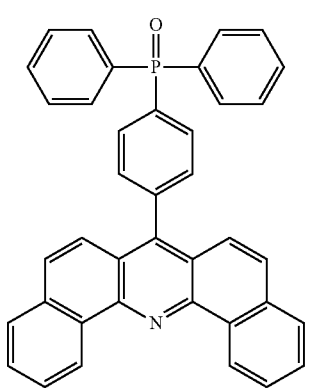

Fourth step: Synthesis of (4-(dibenzo[c,h]acridin-7-yl)phenyl)diphenylphosphine oxide (23). Reactions with butyllithium and with diphenylphosphine chloride were carried out in dry solvents under argon.

(7) (2.84 g, 5.11 mmol) was solved in 40 mL THF. The solution was cooled down to −78° C. and n-BuLi was added dropwise within 20 min (2.5 mol/L, 3.5 mL, 8.68 mmol), and then stirred at that temperature for 1 hour. The temperature is then let rise up to −50° C., and diphenylphosphine chloride (1.13 g, 5.11 mmol) was added and the mixture was stirred overnight at room temperature. The reaction was then quenched with methanol (25 mL), and the solvents were evaporated. The residue was solved in 40 mL dichloromethane and 8 mL aqueous $H_2O_2$ was then added (30% aq. solution w/w) and stirred overnight. The reaction mixture was then washed several times with 50 mL brine, the organic phase was then dried and evaporated. The crude product was purified via column chromatography ($SiO_2$, dichloromethane, then DCM/MeOH 97:3). The foamy product obtained by vacuum evaporation was then washed with 200 mL MTBE.

Yield: 1.6 g (43%)

HPLC: >97%

NMR: $^{31}$P NMR ($CDCl_3$, 121.5 MHz): δ (ppm): 29 (m). $^1$H NMR (500 MHz, $CD_2Cl_2$) δ (ppm): 9.79 (d, 8.06 Hz, 2H), 7.86 (m, 10 Hz), 7.75 (m, 2 Hz), 7.69 (d, 9.20 Hz, 2H), 7.58 (m, 8 Hz), 7.44 (d, 9.18 Hz, 2H).

Synthesis of Structure 42

Fourth step: Synthesis of ((4-(dibenzo[c,h]acridin-7-yl)phenyl)diphenylphosphine sulfide (42). The reactions were carried out under argon.

Fourth step: Synthesis of 7-(4'-(1-phenyl-1H-benzo[d]imidazol-2-yl)-[1,1'-biphenyl]-4-yl)dibenzo[c,h]acridine (26). The Pd-catalyzed condensation was carried out under argon.

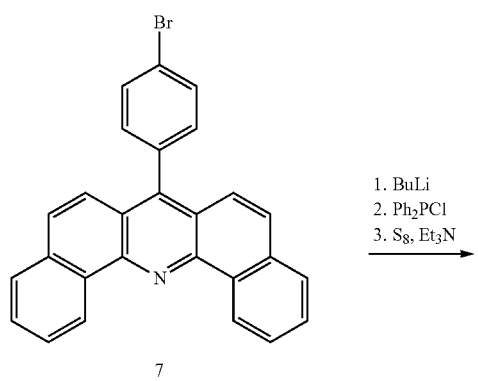

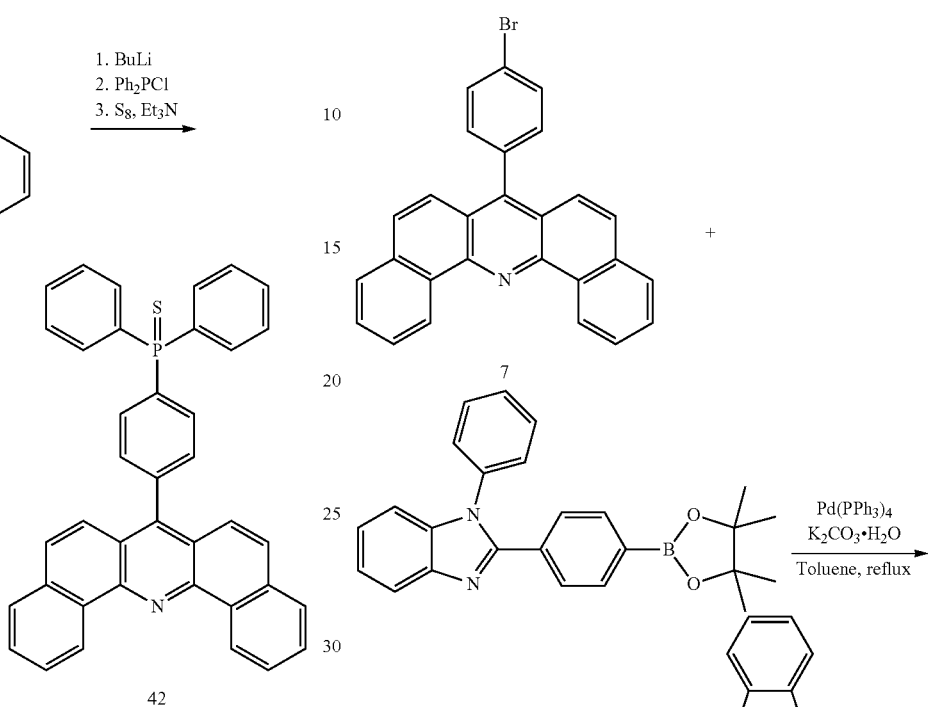

(7) (3 g, 6.9 mmol) was dissolved in 40 mL THF. The solution was cooled down to −78° C., n-BuLi was added dropwise within 20 min (2.5 mol/L, 4.15 mL, 10.35 mmol), and the reaction mixture was stirred at that temperature for 1 hour. The temperature was then let rise up to −50° C., diphenylphosphine chloride (1.13 g, 5.11 mmol) was added and the mixture was stirred overnight at room temperature. Elemental sulfur was then added to the reaction mixture together with 3 drops of triethylamine. The suspension was stirred over the weekend (48 hours) at room temperature. The crude product was then chromatographed.

Yield: 1.6 g

NMR: $^{31}$P NMR (CDCl$_3$, 121.5 MHz): δ (ppm): 29 (m), m.p. 339° C. from DSC peak.

Example 5

Structure 26

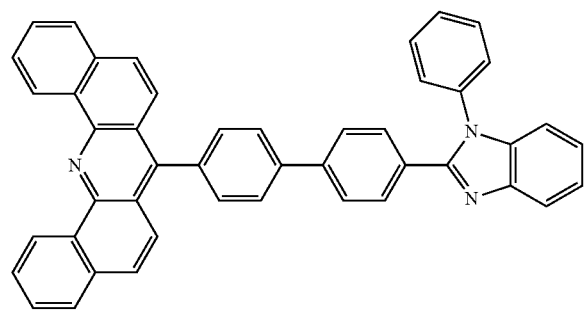

(7) (2.1 g, 4.8 mmol), 1-phenyl-2-(4-(4,4,5,5-tetramethyl-1,3,2-dioxaborolan-2-yl)phenyl)-1H-benzo[d]imidazole (3.8 g, 9.6 mmol), palladium tetrakis triphenylphoshine (830 mg) and 17 mL 1M potassium carbonate aqueous solution were introduced in a flask together with 35 mL degassed toluene. This mixture was stirred at 80° C. during 36 hours, cooled down to room temperature and filtered. The obtained solid was then dissolved in 600 mL DCM and filtered over a Celite pad. The volatiles were removed by rotary evaporation and the solid residue was then dried overnight in a vacuum oven.

Yield: 1.2 g (40%)

HPLC purity >98%. $^1$H NMR (500 MHz, CD$_2$Cl$_2$) δ (ppm): 9.82 (d, 8.16 Hz, 2H), 7.85 (d, 7.60 Hz, 2H), 7.88 (m, 5H), 7.79 (m, 2H), 7.76 (s, 4H), 7.74 (s, 1H), 7.63 (d, 9.2 Hz, 2H), 7.59 (m, 3H), 7.56 (m, 1H), 7.43 (dd, 3.13 Hz, 5.32 Hz, 2H), 7.36 (m, 1H), 7.29 (dt, 3.01 Hz, 3.01 Hz, 7.35 Hz, 2H).

Example 6

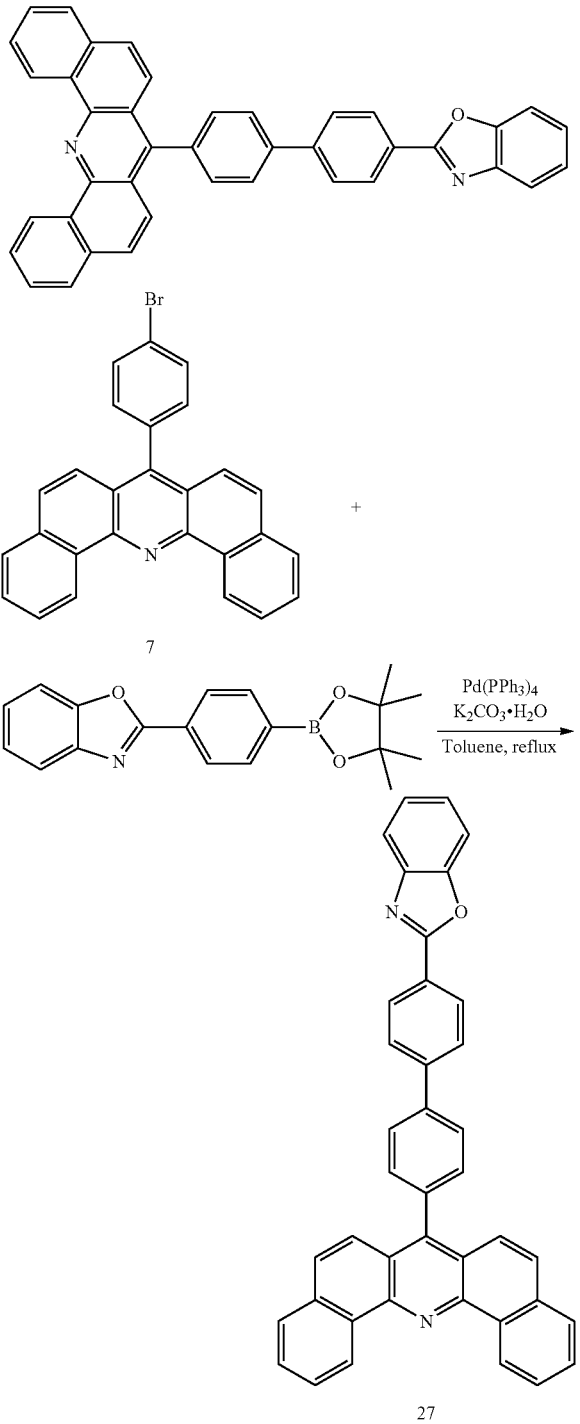

(7) (3 g, 6.9 mmol), 1-phenyl-2-(4-(4,4,5,5-tetramethyl-1,3,2-dioxaborolan-2-yl)phenyl)-1H-benzo[d]imidazole (3.3 g, 10.36 mmol), palladium tetrakis triphenylphoshine (1.2 g) and 30 mL 1M aqueous potassium carbonate solution were introduced in a flask together with 100 mL toluene. This mixture was stirred at 95° C. during 48 hours, cooled down to room temperature, filtered with a paper filter and the obtained grey solid was washed with toluene. The solid was then dispersed in 500 ml hot xylene (in a 150° C. bath), the suspension filtered hot through a celite pad and the volatiles were then removed by rotary evaporation. The obtained solid was then dried in a vacuum oven. Yield: 2.4 g (65%).

HPLC purity: >98%

$^1$H NMR (500 MHz, CD$_2$Cl$_2$) δ (ppm): 9.83 (d, 8.29 Hz, 2H), 8.42 (d, 8.27 Hz, 2H), 7.94 (d, 8.16 Hz, 2H), 7.91 (d. 7.64 Hz, 1 Hz), 7.85 (t, 7.38 Hz, 7.38 Hz, 1H), 7.81 (d, 9 Hz, 1H), 7.76 (t, 7.02 Hz, 2H). 7.71 (d, 9.28 Hz, 1H), 7.61 (dd, 4.02 Hz, 8.63 Hz, 2H), 7.38 (dd, 3.21 Hz, 5.93 Hz, 2H).

Example 7

Synthesis of

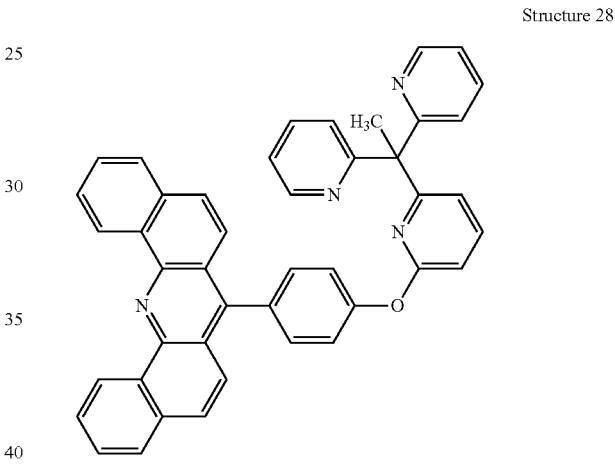

First step: Synthesis of (E)-2-(4-methoxybenzylidene)-3,4-dihydronaphthalen-1(2H)-one (g). All manipulations were carried out in air, without any further purification of commercial solvents/chemicals.

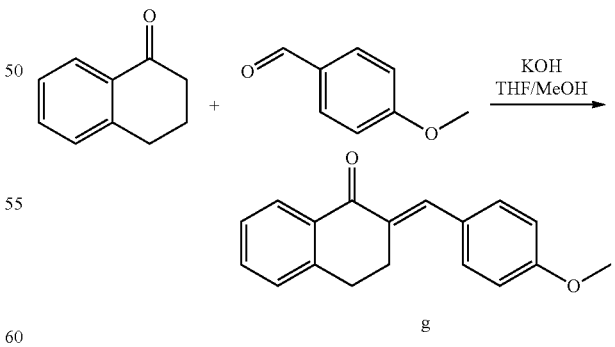

A mixture of p-methoxybenzaldehyde (10.00 g, 73.4 mmol, 1.3 eq) and 1-tetralone (8.24 g, 56.4 mmol, 1 eq) was dissolved in THF (30 mL) and a methanolic solution of potassium hydroxide (4% solution w/w, 250 mL, 7.9 g KOH, 141 mmol, 2.5 eq) was added dropwise over a 15 minutes period to the stirred mixture. The stirring then continued at ambient temperature for three days, the formed precipitate was separated by filtration and purified by washing with MTBE. After drying in vacuo a pale yellow solid (8.57 g, 60% yield, GC-MS purity 99%) was obtained. The filtrate was reduced to a quarter of its volume and a second fraction (3.7 g, 26% yield, GC-MS purity 100%) could be isolated after filtration and washing with a small amount methanol and a higher amount MTBE. The overall yield was 86% and the product was directly used in the next step without any further purification.

Second step: Synthesis of 7-(4-methoxyphenyl)-5,6,8,9-tetrahydrodibenzo[c,h]xanthen-14-ium tetra-fluoroborate (h). The reaction was carried out under argon.

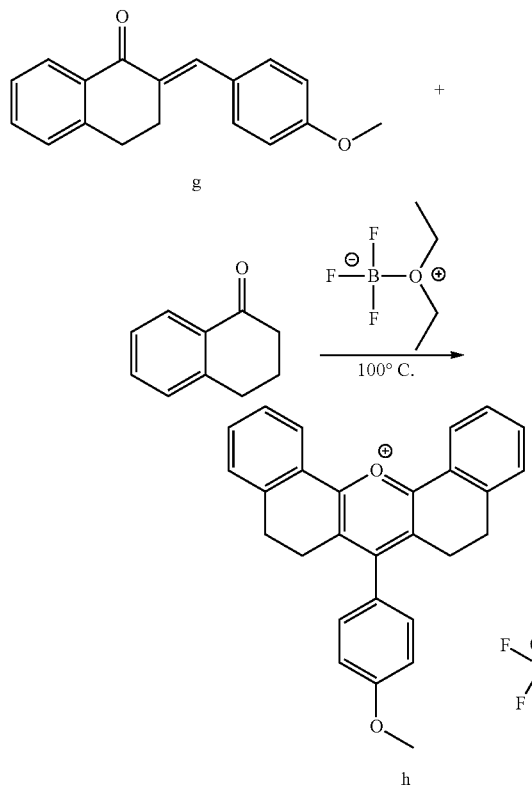

g h

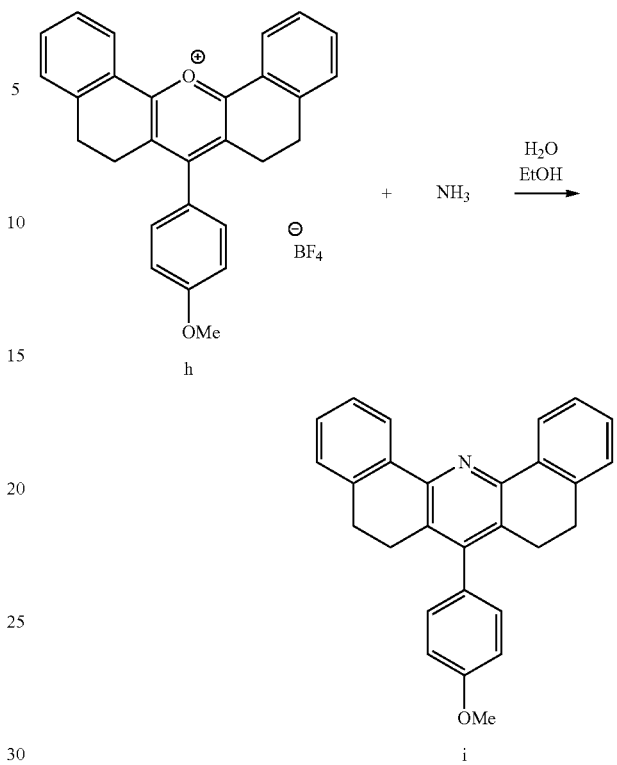

h

In an inert argon atmosphere (diethyloxonio)trifluoroborate (7.83 g, 7.0 mL, 55.2 mmol, 1.2 eq) was added dropwise to a stirred mixture of (E)-2-(4-methoxybenzylidene)-3,4-dihydronaphthalen-1(2H)-one (g) (12.20 g, 46.2 mmol, 1 eq) and 1-tetralone (6.73 g, 46.0 mmol, 1 eq). After complete addition the mixture was heated at 100° C. for 5'A hours and then cooled to room temperature. Diethylether (50 mL) was added and—after stirring over a 30 minutes period—the solid product was isolated by filtration and purified by washing with diethyl ether. After drying in vacuo, an ochre solid was obtained. The product was used in the next step without any further purification.

Yield: 6.66 g (30%)

Third step: Synthesis of 7-(4-methoxyphenyl)-5,6,8,9-tetrahydrodibenzo[c,h]acridine (i). All manipulations were carried out in air, without any further purification of commercial solvents/chemicals.

h (6.63 g, 13.9 mmol, 1 eq) was suspended in ethanol (175 mL, denaturated with 1% methylethyl ketone). Under vigorously stirring an ammonia solution (32% aqueous solution, 18.3 g $NH_3$, 1.075 mol, 77 eq) was added dropwise and the mixture was stirred at ambient temperature for 17'2 hours to obtain a lavender suspension. The product was isolated by filtration and purified by successive washing with ethanol (250 mL). A lavender solid (91% yield) could be obtained. The compound was directly used in the next step without any further purification.

Yield: 4.93 g (91%)

HPLC: 91% (and 5% of a constitution isomer)

Fourth step: Synthesis of 7-(4-methoxyphenyl)dibenzo[c,h]acridine (j). The oxidative dehydrogenation was carried out under argon.

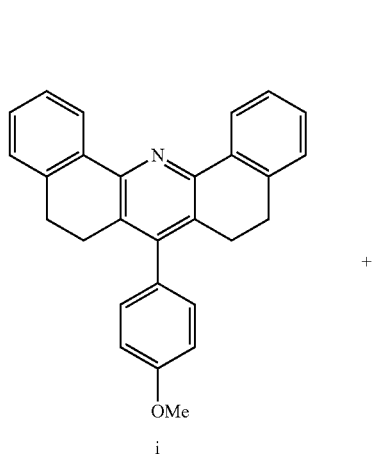

i

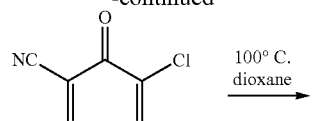

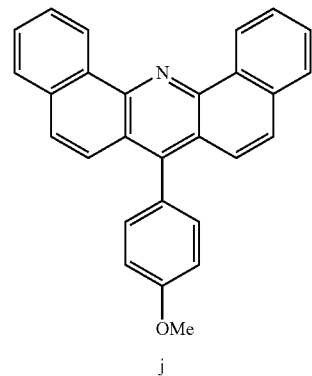

j

In an inert argon atmosphere i (4.93 g, 12.7 mmol, 1 eq) was dissolved in abs. 1,4-dioxane (300 mL, dried over sodium) under vigorously stirring at 80° C. 2,3-dichloro-5,6-dicyano-p-benzoquinone (DDQ, 17.25 g, 76 mmol, 6 eq) was added in portions over a 5 minutes period and the DDQ-vessel was flushed with abs. dioxane (20 mL). The almost black mixture was stirred at 80° C. for two days maintaining the inert atmosphere. After cooling to room temperature, the reaction mixture was carefully added to 500 mL of an aqueous saturated sodium carbonate solution and the reaction vessel was flushed with saturated Na2CO3 solution (250 mL) and water (200 mL). After stirring the mixture at 65° C. for 75 minutes the precipitate was allowed to settle down, the solid product was isolated by filtration and purified by multiple slurrying in water (overall ca. 1000 mL). After drying the crude product in vacuo at 40° C. overnight, the solid was suspended in methylene chloride (20 mL), stirred for 45 minutes, isolated by filtration, washed with DCM (2×20 mL) and dried overnight. 3.53 g ochre solid (72% yield) were obtained with 99.5% HPLC purity.

Further purification of the material was possible by gradient vacuum sublimation (initial amount: 1.00 g, sublimation yield: 67%).

Fifth step: Synthesis of 4-(dibenzo[c,h]acridin-7-yl)phenol (k). The demethylation reaction was carried out under argon.

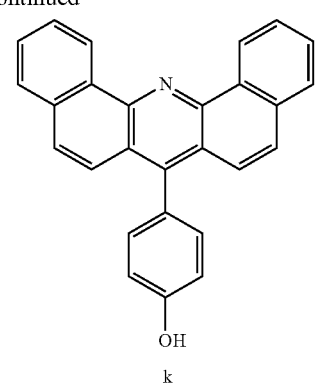

k

In a pressure vessel a mixture of j (1.00 g, 2.6 mmol, 1 eq) and pyridinium hydrochloride (1.75 g, 15.1 mmol, 5.8 eq) was heated to 210° C. under an inert atmosphere and vigorously stirred at this temperature over a three days period. The mixture was allowed to cool down to room temperature. The solidified melt was dissolved in chloroform (50 mL) and water (50 mL) and treated in an ultrasonic bath for 5 minutes. The layers were separated and the aqueous layer was extracted with chloroform (3×50 mL). Afterwards, the combined organic layers were washed with a saturated aqueous sodium hydrogencarbonate solution (5×50 mL) followed by water (3×50 mL) and dried over magnesium sulphate. Evaporation of the solvent at 40° C. led to an old rose coloured solid. The product was directly used in the next step without any further purification.

Yield: 810 mg (84%)

HPLC: 98%

Sixth step: Synthesis of 7-(4-((6-(1,1-di(pyridin-2-yl)ethyl)pyridin-2-yl)oxy)phenyl)dibenzo[c,h]acridine (28). The condensation reaction was carried out under argon.

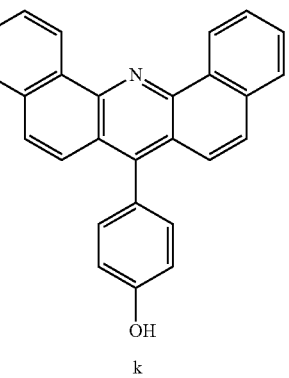

+

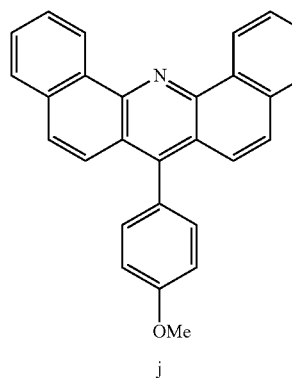

j

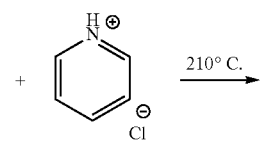

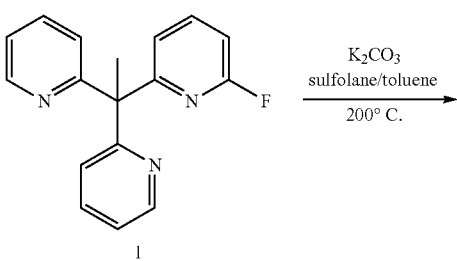

l

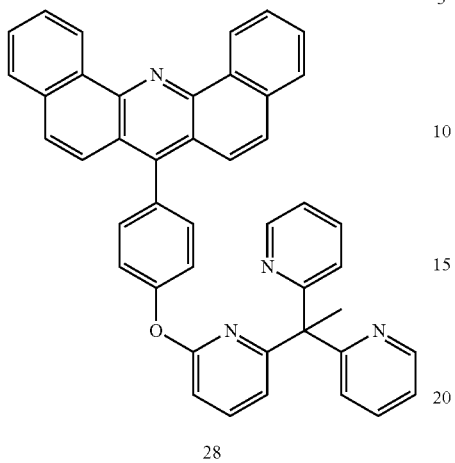

28

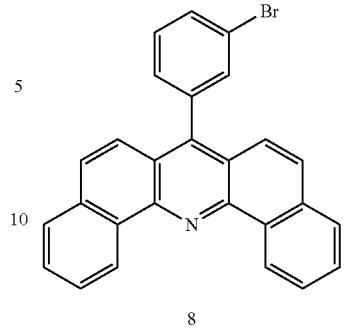

8

1. BuLi
2. Ph₂PCl
3. H₂O₂

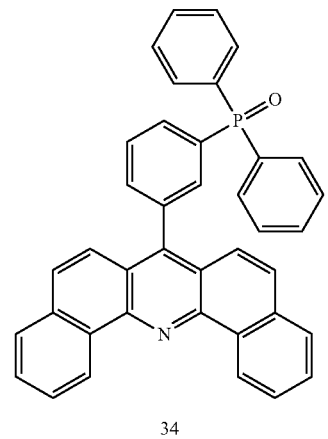

34

In an inert argon atmosphere a mixture of k (700 mg, 1.9 mmol, 1 eq), potassium carbonate (1.31 g, 9.5 mmol, 5 eq) and 1 (531 mg, 1.9 mmol, 1 eq) was placed into a pressure vessel. The vessel was sealed and the mixture was heated to 200° C. under vigorously stirring. After five days reaction at this temperature, the mixture was allowed to cool down and then poured into ice/water (300 mL). The pressure vessel was flushed with water (2×50 mL) and the solution was extracted with dichloromethane (3×100 mL) until the organic layer remained almost colourless. Afterwards, the combined organic layers were washed with water (3×500 mL) followed by 2 N aqueous hydrochloric acid (2×100 mL) and water (300 mL) again. After drying over magnesium sulphate, the solvent was removed in vacuo at 40° C. The product was precipitated from the remaining solution by addition of water (1.000 mL), stirring over 10 minutes and isolated by filtration, washing with water (500 mL) and drying overnight at 40° C. in a vacuum dry box. An ochre solid (0.94 g, 78% yield, HPLC purity 99.2%) was obtained.

Further purification of the material was performed by gradient sublimation (initial amount: 0.93 g, sublimation yield: 43%).

Synthesis of Structure 34

Fourth step: Synthesis of ((3-(dibenzo[c,h]acridin-7-yl) phenyl)diphenylphosphine oxide (34). The reactions with butyllithium and diphenyl phosphine chloride were carried out under argon.

(8) (4.06 g, 9.35 mmol) was dissolved in 60 mL THF. The solution was cooled down to −78° C., n-BuLi was added dropwise within 25 min (2.5 mol/L, 5.6 mL, 14.0 mmol), and the reaction mixture stirred at that temperature for half an hour. The temperature was then let rise up to −50° C., and diphenylphosphine chloride (2.17 g, 9.82 mmol) was added. The mixture was stirred overnight at room temperature. The reaction was then quenched with methanol (30 mL), and the solvents were evaporated. The solid residue was dissolved in 50 mL DCM, 8 mL aqueous $H_2O_2$ (30% by weight) was then added and the mixture was stirred for 24 hours. The reaction mixture was then washed with 50 mL brine and 2×50 mL water, the organic phase was dried and evaporated. The crude product was purified via column chromatography ($SiO_2$, DCM, then DCM/MeOH 99:1). The obtained foamy product was then washed two times with 40 mL acetonitrile.

Yield: 3.1 g (60%). Pale yellow solid.

NMR: $^{31}P$ NMR ($CDCl_3$, 121.5 MHz): δ (ppm): 27 (m) $^1H$ NMR (500 MHz, $CD_2Cl_2$) δ (ppm): 9.78 (d, 8.03 Hz, 2H), 7.95 (m, 3H), 7.85 (m, 2H), 7.76 (m, 11H), 7.57 (ddd, 1.39 Hz, 9.84 Hz, 7.24 Hz, 2H), 7.50 (m, 6H).

m.p. 250° C. (from DSC peak).

Synthesis of Structure 35
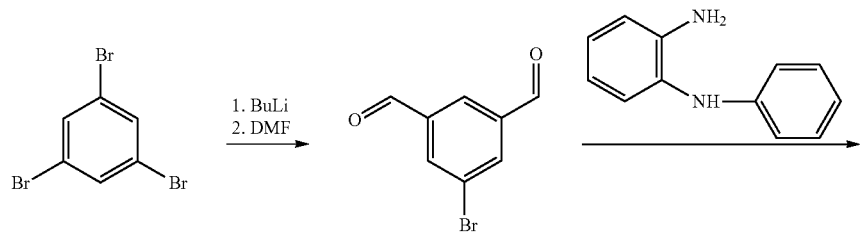
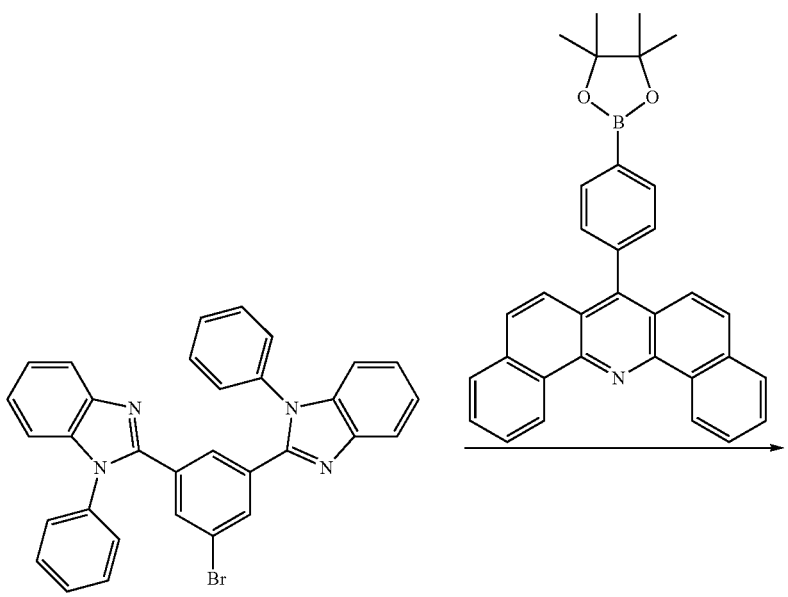
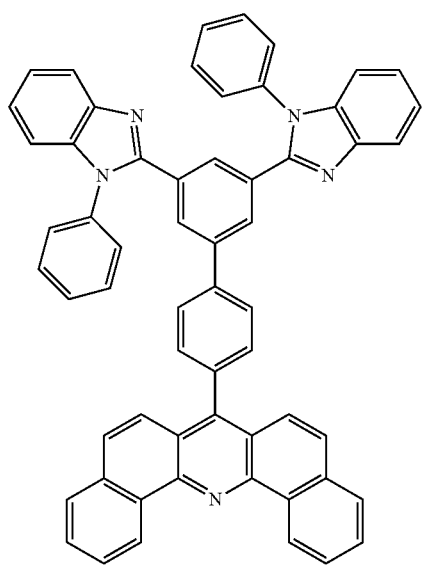
35

77

First Step: Synthesis of 5-Bromoisophthalaldehyde (m)

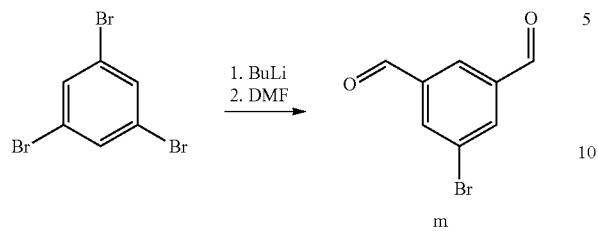

Tribromobenzene (11.25 g, 35.7 mmol) was solved under argon into 380 mL diethylether, then 100 mL tBuLi (100 mL, 1.6 mol/L) were slowly added at −78° C. The solution was stirred 2 hours at −78° C. and 8.5 mL dimethylformamide (DMF) was added dropwise. The solution was then let warm up to the room temperature and stirred for 2 additional hours. The reaction was quenched with water, product extracted with diethylether and the solvents were evaporated. 8 g crude product was obtained and chromatographed.

Yield: 4.6 g (60%)

GC/MS purity: 100%

Second Step: Synthesis of 2,2'-(5-bromo-1,3-phenylene)bis(1-phenyl-1H-benzo[d]imidazole) (n)

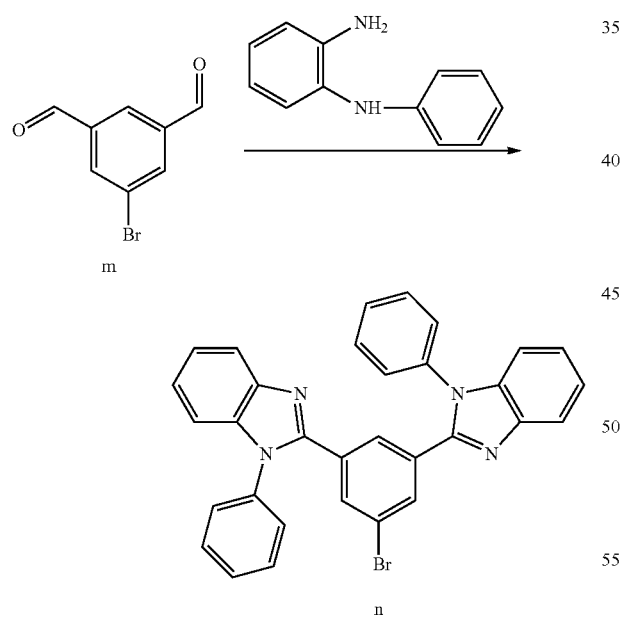

3 g 5-bromoisophthalaldehyde (m) and 5.2 g phenylenediamine were dissolved under argon in 25 mL toluene and 270 mL acetic acid. The solution was stirred 72 hours at 110° C. The reaction mixture was evaporated, treated with 8 mL MTBE and filtered.

Yield: 2 g (27%), HPLC purity 97.5%

78

Third Step: Synthesis of 7-(3',5'-bis(1-phenyl-1H-benzo[d]imidazol-2-yl)-[1,1'-biphenyl]-4-yl)dibenzo[c,h]acridine (35)

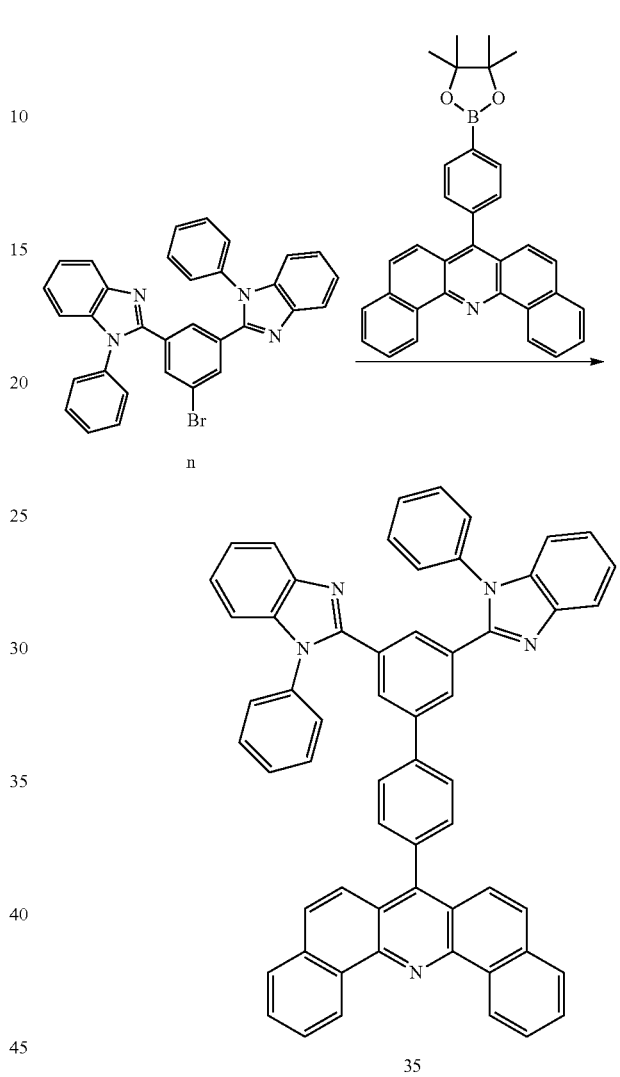

35

2.5 g of n, 3.3 g of 7-(4-(4,4,5,5-tetramethyl-1,3,2-dioxaborolan-2-yl)phenyl)dibenzo[c,h]-acridine, 800 mg palladium tetrakis triphenylphosphine were suspended in 50 mL toluene under argon and 20 mL 1M aqueous potassium carbonate solution were added. The reaction mixture was stirred 48 hours at 95° C.

The reaction mixture was then filtered, the obtained solid was stirred in 500 mL chloroform, filtered through a celite pad and the filtrate evaporated.

Yield: 1.45 g (45%), HPLC purity 98%.

Mp. 341° C. from DSC peak,

Synthesis of Structure 36

Fourth step: Synthesis of bis(4-(dibenzo[c,h]acridin-7-yl)phenyl)(phenyl)phosphine oxide (36)

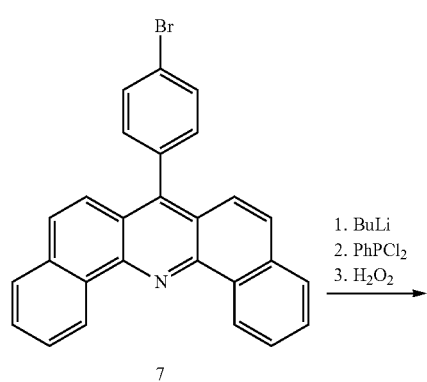

7

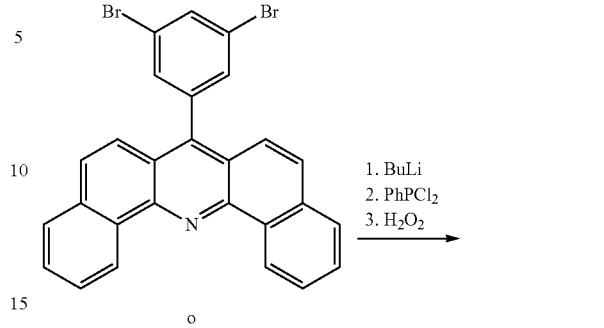

Fourth Step: Synthesis of (5-(dibenzo[c,h]acridin-7-yl)-1,3-phenylene)bis(diphenylphosphine oxide) (37)

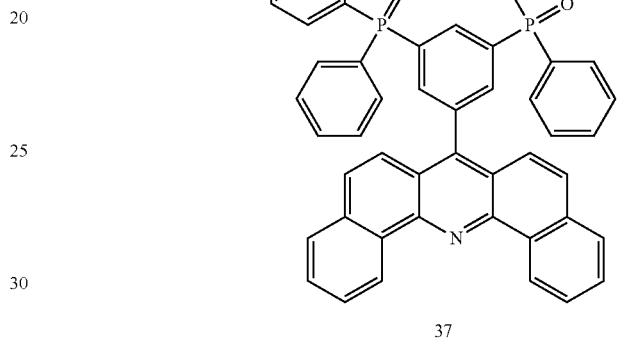

(7) (5.0 g, 11.5 mmol) was dissolved in 65 mL THF. The solution was cooled down to −78° C., n-BuLi was added dropwise within 20 min (2.5 mol/L, 6.8 mL, 17.2 mmol), and the reaction mixture was stirred at that temperature for half an hour. The temperature was then let rise up to −50° C., dichloro(phenyl)phosphine (0.78 mL, 1.02 g, 5.75 mmol) was added and the mixture was stirred overnight at room temperature. The reaction was then quenched with 50 mL methanol and the solvents were evaporated. The residue was dissolved in 85 mL DCM, 20 mL H$_2$O$_2$ aq. (30% by weight) was added and the mixture stirred for 3 days at room temperature. The reaction mixture was then washed with 50 mL brine and 2×25 mL water, the organic phase was dried and evaporated. The crude product was purified via column chromatography (SiO$_2$, DCM, then DCM/MeOH 99.6:0.4). The obtained foamy solid was then washed two times with 20 mL acetonitrile. 1.9 g light orange solid was obtained (40% yield, HPLC purity 96.0%).

Further purification of the material was performed by gradient sublimation (initial amount: 1.92 g, sublimation yield: 77%, m.p. 364° C. from DSC peak).

NMR: $^{31}$P NMR (CDCl$_3$, 121.5 MHz): δ (ppm): 29.2 (m) $^1$H NMR (500 MHz, CD$_2$Cl$_2$) δ (ppm): 9.82 (d, 8.13 Hz, 2H), 8.09 (dd, 8.12 Hz, 11.81 Hz, 2H), 8.00 (m, 1H), 7.90 (d, 7.68 Hz, 2H), 7.85 (m, 2H), 7.72 (m, 7H), 7.51 (d, 9.18 Hz, 2H), Synthesis of Structure 37

1 g of o was dissolved in 20 mL THF, 3.65 mL butyllithium (1.6 M solution) was added at −78° C. and then stirred for 30 min at −78° C. The solution was warmed up to −50° C. and 1.2 mL diphenylphosphine chloride was added dropwise. The reaction mixture was allowed to warm spontaneously to room temperature and stirred overnight. The reaction was then quenched with a few drops of methanol, evaporated and the residue dissolved in 50 mL DCM. 5.2 mL aqueous hydrogen peroxide solution (30% by weight)) was added to the mixture at 0° C., the stirring continued at room temperature overnight. The reaction mixture was then extracted with dichloromethane, the organic phase washed with water, dried and evaporated.

The residue was then chromatographed over SiO$_2$ (hexanes:ethyl acetate 1:2 v/v)

Yield: 930 mg (63%), m.p. 315° C. (from DSC peak).

Synthesis of Structure 43: Synthesis of (5-(dibenzo[c,h]acridin-7-yl)-1,3-phenylene)bis(diphenylphosphine sulfide) (43)

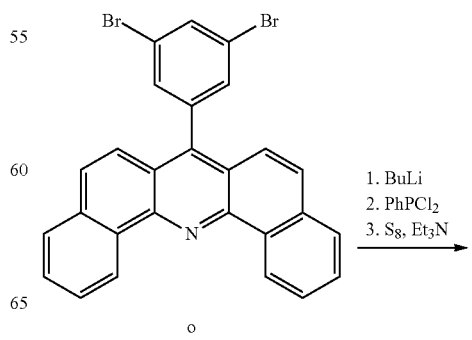

81

-continued

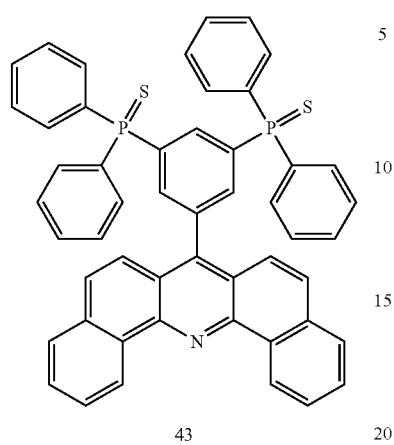

43

The synthetic procedure for 43 was analogous as for 42, with o as starting material.

Synthesis of Structure 39

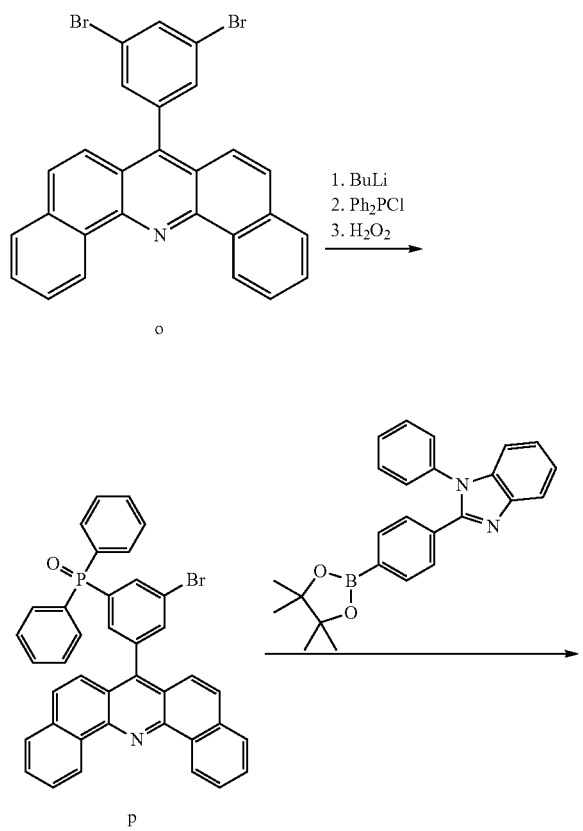

82

-continued

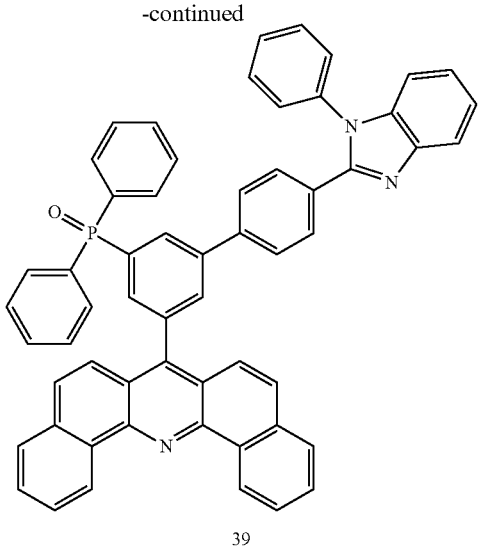

39

Fourth Step: Synthesis of (3-bromo-5-(dibenzo[c,h]acridin-7-yl)phenyl)diphenylphosphine oxide

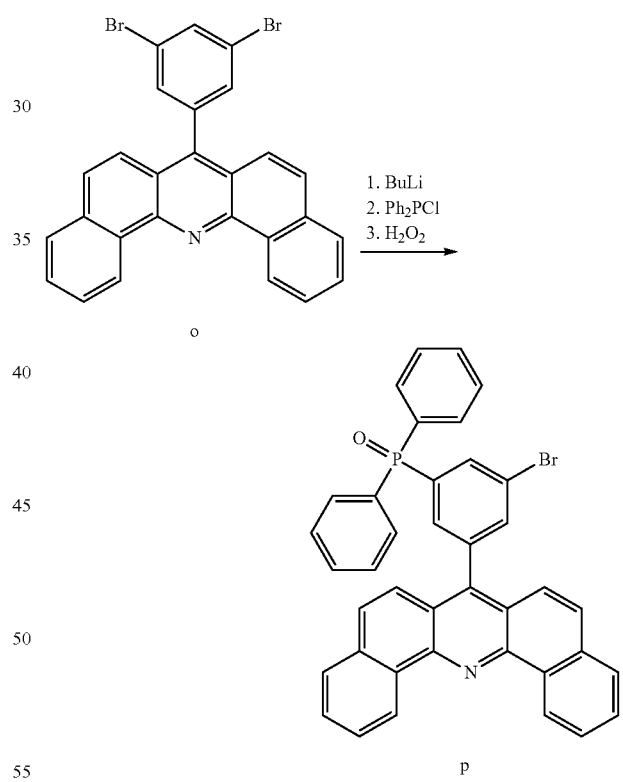

o (1.62 g, 3.15 mmol) was dissolved in 30 mL THF. The solution was cooled down to −78° C., n-BuLi was added dropwise within 15 min (2.5 mol/L, 1.5 mL, 3.78 mmol), and the reaction mixture stirred at that temperature for one hour. The temperature was then let rise up to −50° C., diphenylphosphine chloride (0.73 g, 3.31 mmol) was added and the mixture was stirred overnight at room temperature. The reaction was then quenched with 20 mL methanol, and the solvents were evaporated. The residue was dissolved in 30 mL dichloromethane, 4 mL H₂O₂ (aq., 30% solution by weight) were added and the mixture stirred for 24 h at room temperature. The reaction mixture was then washed with 40 mL brine and 2×40 mL water, the organic phase was dried and evaporated. The crude product was purified via column chromatography (SiO$_2$, dichloromethane, then DCM/MeOH 99.5:0.5 v/v). 1.37 g pale yellow solid were obtained (69% yield, HPLC purity 97.6%).

Fifth Step: Synthesis of (5-(dibenzo[c,h]acridin-7-yl)-4'-(1-phenyl-1H-benzo[d]imidazol-2-yl)-[1,1'-biphenyl]-3-yl)diphenylphosphine oxide (39)

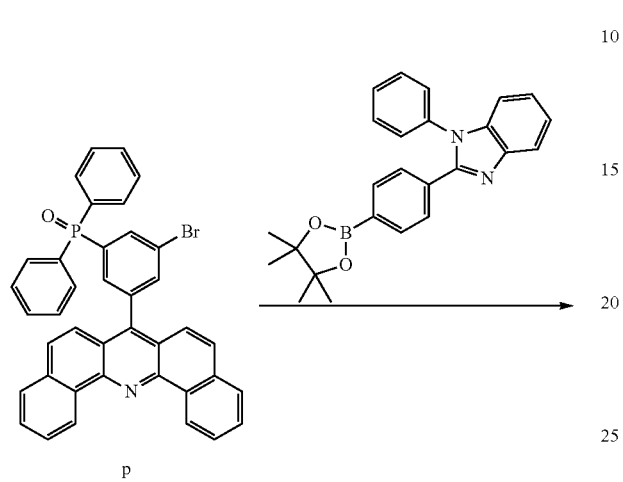

p

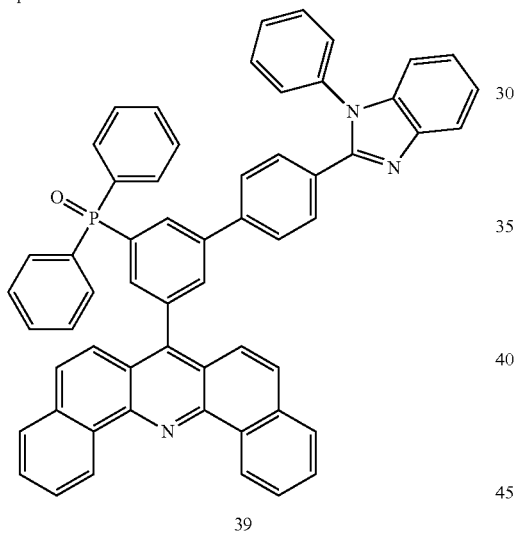

39

1.25 g p, 1.17 g 1-phenyl-2-(4-(4,4,5,5-tetramethyl-1,3,2-dioxaborolan-2-yl)phenyl)-1H-benzo[d]imidazole and 340 mg palladium tetrakis triphenylphosphine were suspended in 20 mL toluene under argon. 9 mL 1M aqueous potassium carbonate solution were added and the reaction mixture was stirred 48 hours at 95° C.

The reaction mixture was then filtered, the product remains in filtrate.

The filtrate was filtered over celite, evaporated and the residue was chromatographed on silica gel (hexanes/ethyl acetate 1:1 v/v).

Yield: 1 g (60%), HPLC purity 99%.

No melting point detected on the DSC curve, decomposition temperature Td: 610° C.

Synthesis of Structures 46-57

Structures 46-51 were prepared the same way as structure 36, using the appropriate dichloroarylphosphine, and hydrogen peroxide as oxidation agent.

Structures 52-57 were prepared the same way as structure 42, using the appropriate dichloroarylphosphine, and elemental sulfur as oxidation agent.

Synthesis of Structure 58

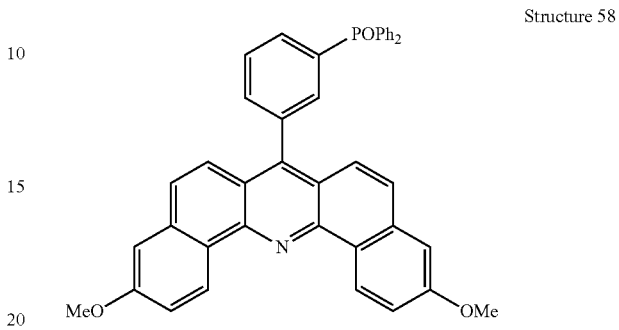

First step: Synthesis of 2-(3-bromobenzylidene)-6-methoxy-3,4-dihydronaphthalen-1(2H)-one (q). All manipulations were carried out in air, without any further purification of commercial solvents/chemicals.

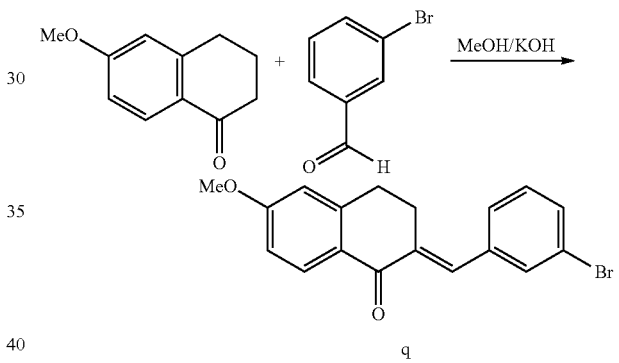

q

A 500 mL flask was charged with 3-benzaldehyde (27.5 g, 0.148 mol), 20 mL THF was added before 6-methoxytetralone (20 g, 0.113 mol). This results in a pale yellow suspension. 4 wt % solution KOH in methanol (34.2 mL) was added dropwise, which caused the suspension to go from yellow to grey-red. The suspension was stirred for 4 hours. It was then filtered and the solid was washed 4 times with 30 mL MeOH and once with 30 mL MTBE. The filtrate remains intensive red.

Yield: 32 g 81.6%, HPLC purity: 99.85%

Second step: Synthesis of 7-(3-bromophenyl)-3,11-dimethoxy-5,6,8,9-tetrahydrodibenzo[c,h]-acridine (r). Both reaction steps were carried out under argon.

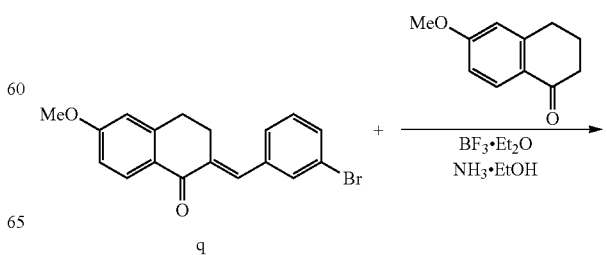

q

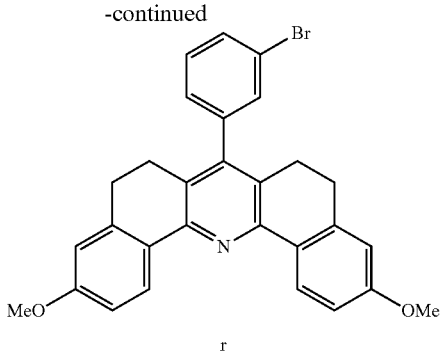

r q (15 g, 43.45 mmol) and 6-mehoxytetralone (7.43 g, 42.2 mmol) were introduced in a 500 mL 2-way flask together with BF$_3$.THF (5.56 mL, 50.4 mmol). The mixture was stirred at 110° C. for 18 hours and cooled down to room temperature. 200 mL THF was added, and stirred under ultrasonic bath (10 min). The suspension was then filtered to obtain 9.76 g red solid. ESI-MS confirmed the wished mass. The obtained solid was put in ethanol (200 mL) which resulted in an orange suspension. An aqueous solution of ammonium hydroxide was then added which caused the suspension to turn green. The mixture was stirred overnight at room temperature. The resulting suspension was filtered, washed 3 times with 50 mL ethanol and dried.

Yield: 3.9 g (18.5%). Purity HPLC 98.4%.

Third step: Synthesis of 7-(3-bromophenyl)-3,11-dimethoxydibenzo[c,h]acridine (60). The oxidative dehydrogenation was carried out under argon with dry solvents.

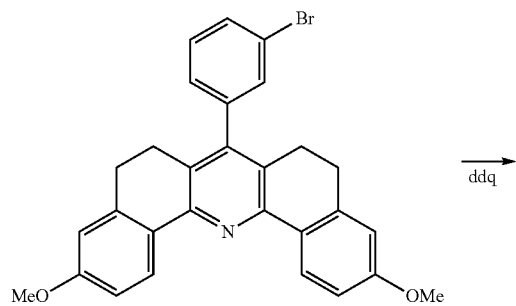

r

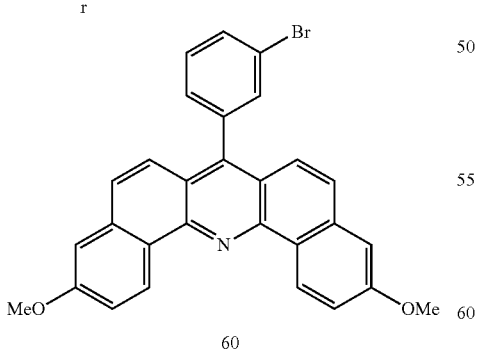

60 r (2 g, 4.0 mmol) was dissolved in 125 mL dioxane and 2,3-dichloro-5,6-dicyanobenzoqui-none was added (12 g, 53 mmol). The mixture was refluxed under argon for 5 days. The reaction mixture was then cooled to room temperature, poured in 500 mL saturated aqueous sodium carbonate solution and stirred at 70° C. for 30 min. The mixture was then cooled to room temperature; the precipitated material was filtered and washed with 200 mL water.

Yield: 1.8 g light brown powder (90.9%). HPLC purity 97%

$^1$H NMR (500 MHz, CD$_2$Cl$_2$) δ (ppm): 9.65 (d, 8.98 Hz, 2H), 7.76 (ddd, 1.04 Hz, 1.92 Hz, 8.09 Hz, 1H), 7.65 (dd, 5.50 Hz, 8.22 Hz, 3H), 7.53 (t, 7.81 Hz, 1H), 7.48 (d, 9.2 Hz, 2H), 7.44 (dd, 2.58 Hz, 8.96 Hz, 3H), 7.32 (d, 2.55 Hz, 2H), 4.01 (s, 6H).

Fourth step: Synthesis of (3-(3,11-dimethoxydibenzo[c,h]acridin-7-yl)phenyl)diphenylphos-phine oxide (58). The reactions with butyllithium and diphenylphosphine chloride were carried out under argon in dry solvents.

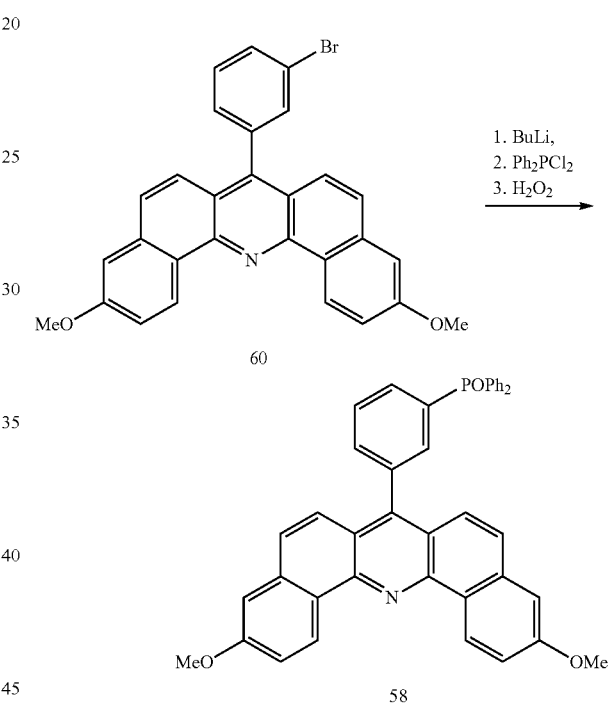

60 (1.8 g, 3.6 mmol) was dissolved in 17.5 mL THF. The solution was cooled down to −78° C., n-BuLi was added dropwise within 25 min (2.5 mol/L, 2.2 mL, 5.46 mmol), and the reaction mixture was stirred at that temperature for an hour. The temperature was then let rise up to −50° C., and diphenylphosphine chloride (0.8 g, 3.65 mmol) was added. The mixture was stirred overnight at room temperature. The reaction was then quenched with methanol (15 mL), and the solvents were evaporated. The solid residue was dissolved in 50 mL DCM, 10 mL aqueous H$_2$O$_2$ (30% by weight) was then added and the mixture was stirred for 48 hours. The reaction mixture was then filtered, the collected solid was washed with 50 mL brine and 2×50 mL water and dried.

Yield: 670 mg light brown powder, HPLC purity 29.8%.

After one high vacuum sublimation, the purity reached 99.3% (light yellow powder) and m.p. from DSC (onset at 1 K/min) was 266° C.

Synthesis of Structure 59

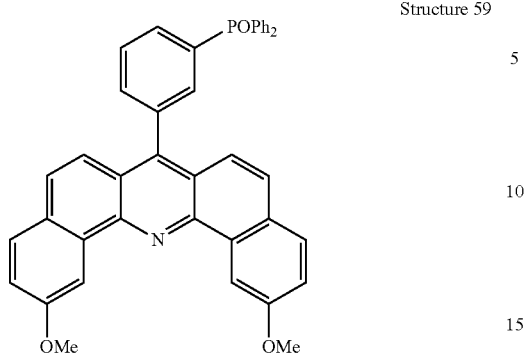

Structure 59

First step: Synthesis of 2-(3-bromobenzylidene)-7-methoxy-3,4-dihydronaphthalen-1(2H)-one (s). All manipulations were carried out in air, without any further purification of commercial solvents/chemicals.

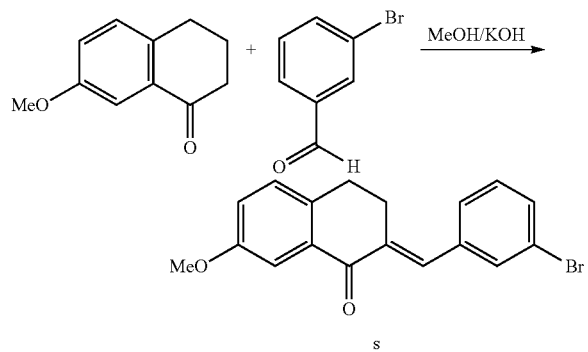

A 100 mL flask was charged with 3-benzaldehyde (13.75 g, 74.34 mmol); then 10 mL THF was added before 7-methoxytetralone (10 g, 56.75 mmol). This resulted in a pale yellow suspension. 4 wt % solution KOH in methanol (34.2 mL) was added dropwise, which caused the suspension to go from yellow, to green and then to grey. After 10 min of stirring, the suspension turned pinkish. The suspension was stirred for an additional 3 hours. It was then filtered and the solid was washed 4 times with 30 mL MeOH and once with 30 mL MTBE. The filtrate remains intensive red.

Yield: 18.5 g, 95%. HPLC purity: 98.6%.

Second step: Synthesis of 7-(3-bromophenyl)-2,12-dimethoxy-5,6,8,9-tetrahydrodibenzo[c,h]-acridine (t). Both reaction steps were carried out under argon.

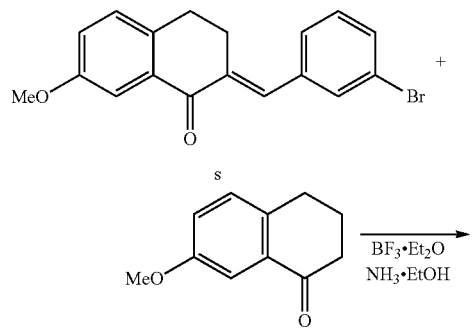

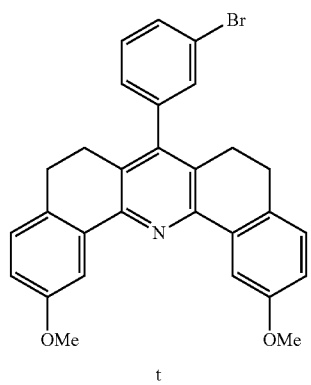

t s (19.9 g, 57.64 mmol) and 7-mehoxytetralone (9.86 g, 55.96 mmol) were introduced in a 500 mL 2-way flask together with $BF_3 \cdot THF$ (7.2 mL, 64.91 mmol). The mixture was stirred at 110° C. for 18 hours and cooled down to room temperature. 200 mL MTBE was added, and the mixture was stirred on ultrasonic bath for 10 min. 100 mL MTBE were added again. The suspension was then filtered and the collected solid was washed with MTBE to obtain 14.9 g red solid. ESI-MS confirmed the expected molar mass. The crude intermediate was put in ethanol (250 mL), affording an orange suspension. An aqueous solution of ammonium hydroxide was then added which caused the suspension to turn green. The mixture was stirred overnight at room temperature. The resulting suspension was filtered, the collected solid was washed 3 times with 50 mL ethanol and dried.

The green solid was re-crystallized from EtOH.

Yield: 10.3 g (32%). Purity HPLC 98%.

$^1$H NMR (500 MHz, $CD_2Cl_2$) δ (ppm): 8.10 (d, 2.75 Hz, 2H), 7.59 (m, 1H), 7.40 (m, 2H), 7.18 (d, 7.63 Hz, 1H), 7.14 (d, 8.23 Hz, 2H), 6.86, (dd, 2.78 Hz, 8.21 Hz, 2H), 2.78 (t, 7.27 Hz, 4H), 2.62 (m, 4H)

Third step: Synthesis of 7-(3-bromophenyl)-2,12-dimethoxydibenzo[c,h]acridine (61). The oxidative dehydrogenation was carried out under argon with dry solvents.

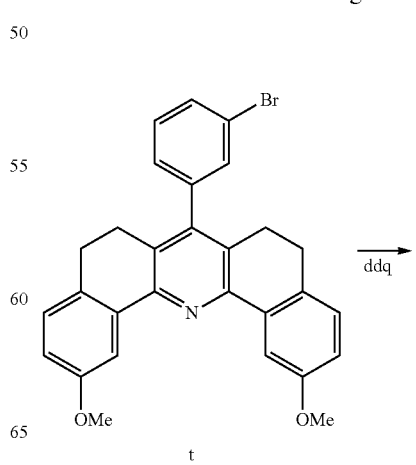

t

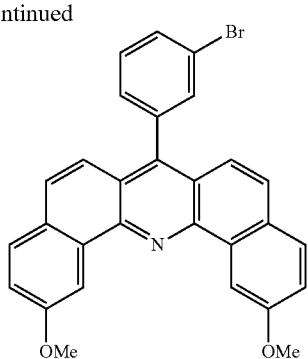

61 t (5 g, 10.03 mmol) was dissolved in 250 mL dioxane and 2,3-dichloro-5,6-dicyanobenzoquinone was added (13.66 g, 60.19 mmol). The mixture was then refluxed under argon for 2 days. The reaction mixture was then cooled to room temperature, poured in 500 mL saturated aqueous sodium carbonate solution and stirred at 70° C. for 30 min. The mixture was then cooled to room temperature; the precipitated material was filtered and washed with 200 mL water and 50 mL EtOH.

Yield: 4.4 g (89%). $^1$H NMR was in accordance with the expected structure:

$^1$H NMR (500 MHz, CD$_2$Cl$_2$) δ (ppm): 9.21 (d, 2.41 Hz, 2H), 7.85 (d, 8.61 Hz, 2H), 7.76 (d, 8.06 Hz, 1H). 7.67 (m, 3H), 7.53 (t, 7.8 Hz, 1H), 7.44 (d, 7.52 Hz, 1H) 7.39 (m, 4H)), 4.16 (s, 6H).

Fourth step: Synthesis of (3-(2,12-dimethoxydibenzo[c,h]acridin-7-yl)phenyl)diphenyl-phosphine oxide (59). The reactions with butyllithium and diphenylphosphine chloride were carried out under argon in dry solvents.

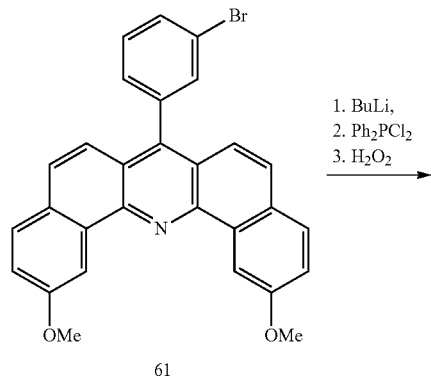

61

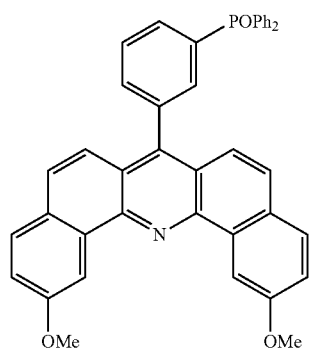

59

61) (4.4 g, 8.9 mmol) was dissolved in 50 mL THF. The solution was cooled down to −78° C., n-BuLi was added dropwise within 25 min (2.5 mol/L, 3.92 mL, 9.72 mmol), and the reaction mixture was stirred at that temperature for an hour. The temperature was then let rise up to −50° C., and diphenylphosphine chloride (1.96 g, 8.9 mmol) was added. The mixture was stirred overnight at room temperature. The reaction was then quenched with methanol (15 mL), and the solvents were evaporated. The solid residue was dissolved in 50 mL DCM, 10 mL aqueous H$_2$O$_2$ (30% by weight) was then added and the mixture was stirred for 24 hours. The reaction mixture was then washed with 50 mL brine and 2×50 mL water, the organic phase was dried and evaporated. The crude product was purified via column chromatography (SiO$_2$, DCM, then DCM/MeOH 99:1). The foamy product obtained after rotary evaporation of the solvent was recrystallized from MeOH.

Yield: 3.5 g light yellow powder, HPLC purity 97.8%. After high vacuum sublimation, the purity reached 99.0% and m.p. was 293° C. (from DSC peak).

NMR: $^{31}$P NMR (CDCl$_3$, 121.5 MHz): δ (ppm): 27.1 (m) $^1$H NMR (500 MHz, CD$_2$Cl$_2$) δ (ppm): 9.19 (d, 2.60 Hz, 2H), 7.99 (ddt, 1.32 Hz, 7.71 Hz, 11.7 Hz, 1H), 7.87 (d, 8.62 Hz, 2H), 7.81 (m, 6H), 7.72 (dd, 1.38 Hz, 7.55 Hz, 1H), 7.67 (d, 9.18 Hz, 2H), 7.59 (m, 6H), 7.40 (dd, 2.68 Hz, 8.61 Hz, 2H), 7.34 (d, 9.14 Hz, 2H), 4.31 (s, 6H).

Device Examples

Comparative Example

A top emitting blue sub-pixel was fabricated on a substrate with a 100 nm thick Ag anode, with the following layer sequence:
1. p-doped a-NPD as hole injection and transporting layer with thickness of 120 nm;
2. undoped a-NPD with thickness of 10 nm;
3. emitter layer with Spiro-Pye:BCzVB (98.5:1.5) with thickness of 20 nm. Spiro-Pye is 2,7-di-pyrenyl-9,9-spirobifluorene. BCzVB is 1,4-bis[2-(3-N-ethylcarbazoryl)vinyl]-benzene;
4. a BPhen:LiQ (60:40) electron transport layer with thickness of 20 nm;
5. a 1 nm thick LiQ layer as electron injection layer;
6. a cathode with 1.5 nm of Ag, followed by 11 nm of Mg;
7. an outcoupling layer of 60 nm of a-NPD;

Inventive Example

A device was made as explained above except for the electron transport layer which was replaced by compound 27:LiQ (60:40), with the same layer thickness.

The comparative as well as the inventive examples have a very deep blue emission with colour coordinates of X=0.15 and Y=0.03-0.04 on the CIE 1931 chart.

Figure 6:
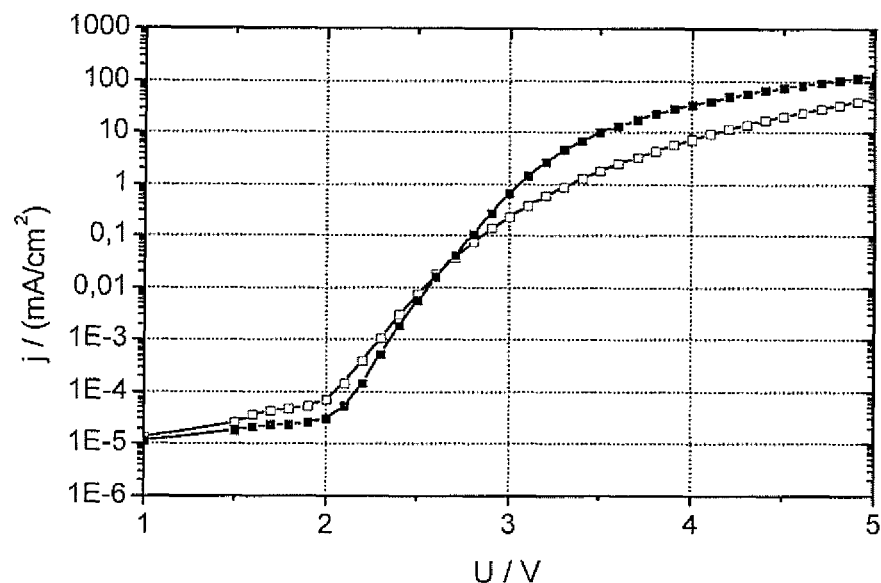
FIG. 6 shows a comparison of the current-voltage curves of comparative and inventive devices.

FIG. 6 shows a comparison of the IxV curves of the device with BPhen (open squares) and the device with compound of structure 27 (black filled squares). It can be seen that the inventive device has a much higher current than the comparative example. We also compared the voltage of 8 comparative to 8 inventive devices and found that the inventive devices always have a lower operating voltage at 10 mA/cm2 of at least 0.5 V lower.

Figure 7:
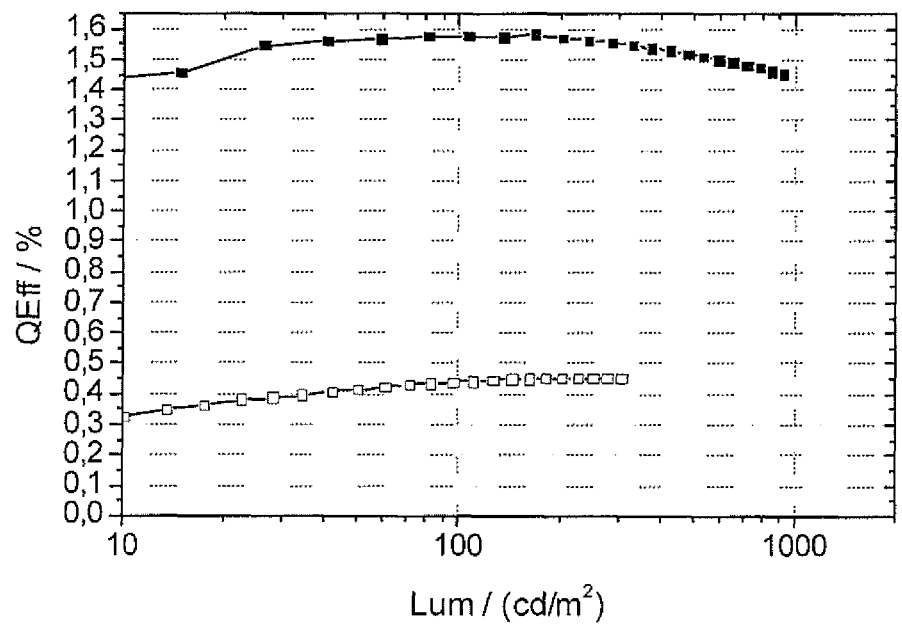
FIG. 7 shows a comparison of the quantum efficiency of the devices as used in FIG. 6.
Figure 8:
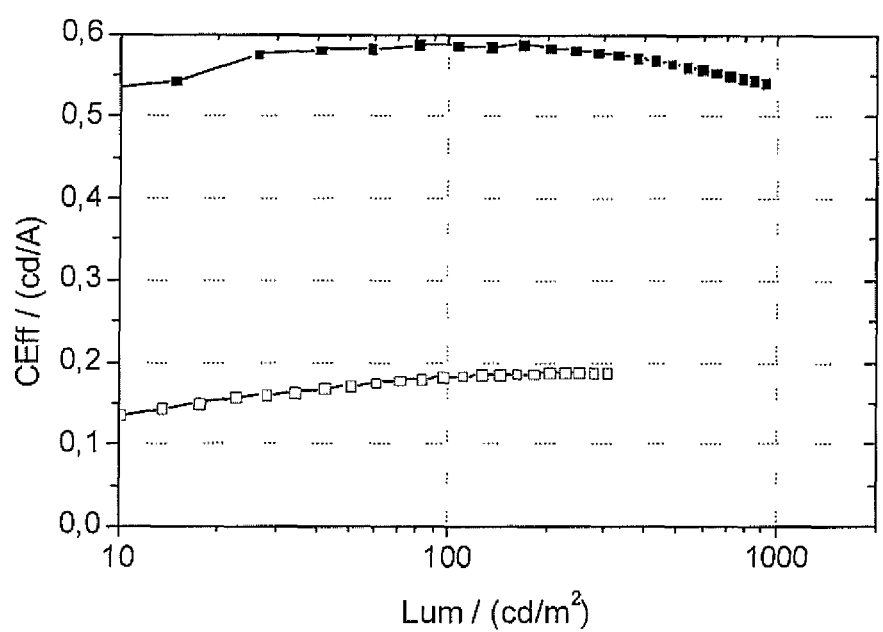
FIG. 8 shows a comparison of the current efficiency vs. the luminance of the devices used.

FIG. 7 shows the comparison of the quantum efficiency (QEff) of both devices versus its Luminance; the comparative data is represented by the open squares and the data from the inventive device are the black filled squares. The fact that the overall efficiency is not very high is attributed to the emitter materials, which were used as received, without further purification. It can be seen that the inventive device has a five fold increases QEff as compared to the device with BPhen. The same advantages of the inventive device can be seen in FIG. 8, which compare the current efficiency vs. the luminance of both devices; Bphen being the open squares and inventive being represented by the black filled squares.

OLED stacks requiring other material properties, for instance with other emitter materials, can use the materials according to formula (I). The best rule for selection of a suitable material is the LUMO level of the materials according to formula (I), which are given in the table below:

| Material of Structure | LUMO vs. Fc/Fc+ (V) in THF |
|---|---|
| (1) | −2.28 |
| (2) | −2.28 |
| (3) | −2.25 |
| (4) | −2.26 |
| (19) | −2.21 |
| (23) | −2.20 |
| (26) | −2.24 |
| (27) | −2.24 |
| (28) | −2.29 |
| (29) | −2.22 |
| (34) | −2.20 |
| (36) | −2.19 |
| (37) | −2.19 |
| (39) | −2.19 |
| (42) | −2.24 |

Another key figure for selection of the material is the required conductivity. The conductivity can be, for example, measured by the so-called 2-point or 4-point-method. Here, contacts of a conductive material, such as gold or indium-tin-oxide, are disposed on a substrate. Then, the thin film to be examined is applied onto the substrate, so that the contacts are covered by the thin film. After applying a voltage to the contacts the current is measured. From the geometry of the contacts and the thickness of the sample the resistance and therefore the conductivity of the thin film material can be determined. The four point or two point method give essentially the same conductivity values for doped layers since the doped layers grant a good ohmic contact.

Examples of measured conductivities for materials according to formula (I) doped with 10% of NDOPI are given in the table below:

| Material of Structure | Conductivity S/cm |
|---|---|
| (1) | 6E−5 |
| (2) | 2E−5 |
| (3) | 3E−5 |
| (4) | 2E−6 |
| (19) | 7E−6 |
| (23) | 5E−6 |
| (26) | 1E−5 |
| (27) | 7E−5 |
| (36) | 2E−5 |

The results are given for comparison, bigger conductivities can be obtained if stronger dopants are used, for instance compound (4) doped with 10 weight % W2(hpp4) has a conductivity of 5E−4 S/cm.

The skilled in the art can recognize the features disclosed in the foregoing description, in the claims and the drawings which may, both separately and in any combination thereof, be material for realizing the invention in diverse forms thereof.

SYMBOLS, ABBREVIATIONS, TERMS

OLED—Organic light emitting diode
Display—Device used to present information, comprising a plurality of picture elements (pixels). Preferable device is the active matrix display. A pixel is comprised by sub-pixels of different colors.
IETM—Inventive electron transport material is an electron transporting material comprising a compound according to formula (I).
IETL—Electron transport layer comprising the IETM.
EIL—Electron injecting layer
ETL—Electron transporting layer
HTL—Hole transporting layer
HIL—Hole injecting layer
EIM—Electron injecting material
ETM—Electron transporting material
HTM—Hole transporting material
HIM—Hole injecting material
EML—Light emitting layer
p:HTL—p-doped HTL
n:ETL—n-doped ETL
QEff—quantum efficiency
DCM dichloromethane
THF tetrahydrofuran
MTBE methyl-tert-butylether
NMR nuclear magnetic resonance
HPLC high performance liquid chromatography; HPLC purities of compounds are given throughout the application in usual "area %" relative units—based on comparison of the area under the peak assigned to the analyzed compound with the whole area under all integrated peaks in the chromatogram
GC/MS gas chromatography/mass spectrometry, the GC/MS purities are also given in area %
ESI-MS electrospray-ionisation mass spectroscopy
w/w by weight
v/v by volume
mol. molar (e.g. percent)
eq equivalent
LiQ lithium 8-hydroxyquinolinolate
MeOH methanol
EtOH ethanol
m.p. melting point
DSC differential scanning calorimetry

The invention claimed is:

1. A display comprising at least one organic light emitting diode, wherein the at least one organic light emitting diode comprises an anode, a cathode, a light emitting layer arranged between the anode and the cathode, and at least one layer arranged between the cathode and the light emitting layer, the at least one layer comprising a compound according to formula (I):

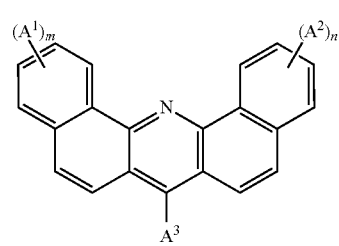

wherein $A^1$ and $A^2$ are independently selected from halogen, CN, substituted or unsubstituted $C_1$-$C_{20}$-alkyl or heteroalkyl, substituted or unsubstituted $C_6$-$C_{20}$-aryl or $C_5$-$C_{20}$-heteroaryl, or substituted or unsubstituted $C_1$-$C_{20}$-alkoxy or $C_6$-$C_{20}$-aryloxy,
$A^3$ is selected from substituted or unsubstituted $C_6$-$C_{40}$-aryl or $C_5$-$C_{40}$-heteroaryl,
m is 0, 1 or 2, and
n is 0, 1 or 2.

2. The display according to claim 1, wherein the compound of formula (I) has a structure according to generic formula (II):

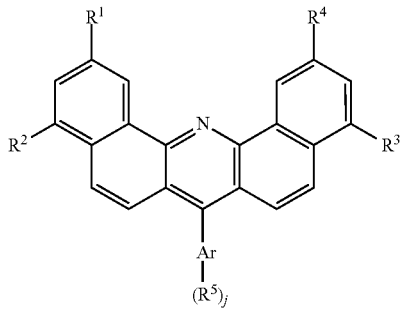

(II)

wherein each $R^1$-$R^4$ is independently selected from H, halogen, CN, substituted or unsubstituted $C_1$-$C_{20}$-alkyl or heteroalkyl, substituted or unsubstituted $C_6$-$C_{20}$-aryl or $C_5$-$C_{20}$-heteroaryl, or substituted or unsubstituted $C_1$-$C_{20}$-alkoxy or $C_6$-$C_{20}$-aryloxy, Ar is a substituted or unsubstituted $C_6$-$C_{24}$ arene or substituted or unsubstituted $C_5$-$C_{24}$-heteroarene, j is 1 or 2, and each $R^5$ is independently selected from substituted or unsubstituted $C_6$-$C_{20}$-aryl or $C_5$-$C_{20}$-heteroaryl, H, F, or

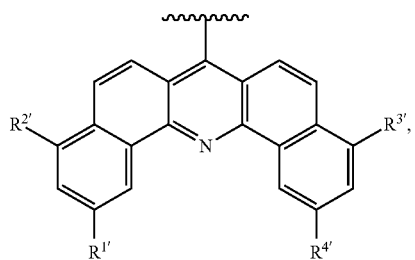

wherein each $R^{1'}$-$R^{4'}$ is independently selected from H, halogen, CN, substituted or unsubstituted $C_1$-$C_{20}$-alkyl or heteroalkyl, substituted or unsubstituted $C_6$-$C_{20}$-aryl or $C_5$-$C_{20}$-heteroaryl, or substituted or unsubstituted $C_1$-$C_{20}$-alkoxy or $C_5$-$C_{20}$-aryloxy.

3. The display according to claim 2, wherein each of $R^1$-$R^4$ is independently selected from H, substituted or unsubstituted $C_6$-$C_{20}$ aryl, or substituted or unsubstituted $C_5$-$C_{20}$-heteroaryl.

4. The display according to claim 1, wherein $A^3$ comprises at least one group selected from the group consisting of phosphine oxide and phosphine sulfide.

5. The display according to claim 1, wherein $A^3$ is

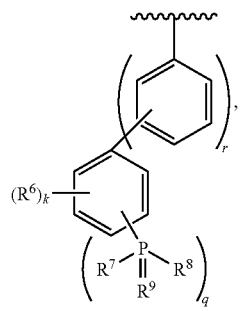

wherein $R^6$ is selected from H, F, CN, or substituted or unsubstituted $C_6$-$C_{20}$-aryl or $C_5$-$C_{20}$-heteroaryl, each of $R^7$ and $R^8$ is independently selected from $C_6$-$C_{20}$-aryl or $C_5$-$C_{20}$-heteroaryl which is unsubstituted or substituted, $R^9$ is O or S, r is 0, 1, 2, 3 or 4, k is 0 or 1, and q is 1, 2 or 3.

6. The display according to claim 1, wherein the layer comprising the compound according to formula (I) comprises an additional material selected from a redox n-dopant, an alkaline metal complex, or alkaline earth metal complex.

7. The display according to claim 1, wherein the layer comprising the compound according to formula (I) is an exciton blocking layer.

8. The display according to claim 1, wherein the at least one organic light emitting diode emits white light.

9. The display according to claim 1, wherein the device comprises a first and a second organic light emitting diode, wherein the first organic light emitting diode emits light in a first color, and the second organic light emitting diode emits light in a second color other than the first color.

10. The display according to claim 9, wherein the compound according to formula (I) of the first organic light emitting diode and the compound according to formula (I) of the second organic light emitting diode are the same compounds.

11. A compound according to formula (I):

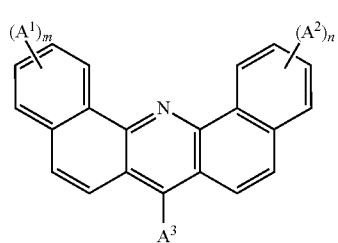

(I)

wherein $A^1$ and $A^2$ are independently selected from halogen, CN, substituted or unsubstituted $C_1$-$C_{20}$-alkyl or heteroalkyl, substituted or unsubstituted $C_6$-$C_{20}$-aryl or $C_5$-$C_{20}$-heteroaryl, or substituted or unsubstituted $C_1$-$C_{20}$-alkoxy or $C_6$-$C_{20}$-aryloxy, m and n are independently selected from 0, 1 or 2, $A^3$ is

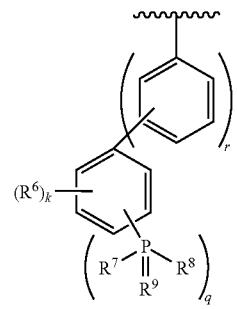

wherein $R^6$ is selected from H, halogen, CN, substituted or unsubstituted $C_1$-$C_{20}$-alkyl or $C_1$-$C_{20}$-heteroalkyl, substituted or unsubstituted $C_6$-$C_{20}$-aryl or $C_5$-$C_{20}$-heteroaryl, or substituted or unsubstituted $C_1$-$C_{20}$-alkoxy or $C_6$-$C_{20}$-aryloxy;

each of R⁷ and R⁸ is independently selected from substituted or unsubstituted $C_6$-$C_{20}$-aryl or $C_5$-$C_{20}$-heteroaryl;
q is selected from 1, 2, or 3;
k is 0 or 1,
r is selected from 0, 1, 2, 3 or 4,
R⁹ is O or S;
wherein the following compounds are excluded:

(i)

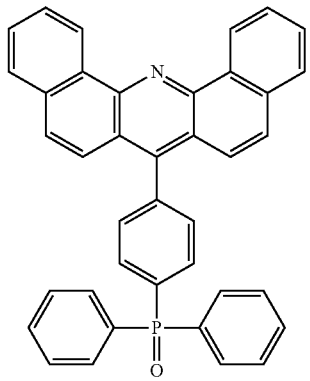

and (ii)

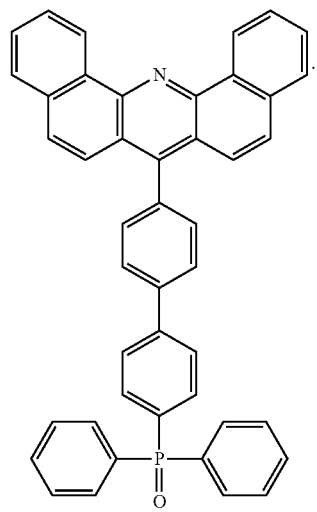

12. The compound according to claim 11 having the formula (IV)

(IV)

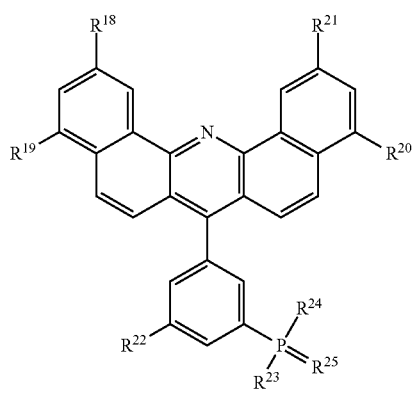

wherein each of $R^{18}$-$R^{22}$ is independently selected from H, halogen, CN, substituted or unsubstituted $C_1$-$C_{20}$-alkyl or $C_1$-$C_{20}$-heteroalkyl, substituted or unsubstituted $C_6$-$C_{20}$-aryl or $C_5$-$C_{20}$-heteroaryl, or substituted or unsubstituted $C_1$-$C_{20}$-alkoxy or $C_6$-$C_{20}$-aryloxy;

each of $R^{23}$ and $R^{24}$ is independently selected from substituted or unsubstituted $C_6$-$C_{20}$-aryl or $C_5$-$C_{20}$-heteroaryl, and $R^{25}$ is O or S.

13. The compound according to claim 12, wherein each of $R^{18}$-$R^{21}$ in formula (IV) is independently selected from H, substituted or unsubstituted $C_1$-$C_{20}$-alkyl, substituted or unsubstituted $C_1$-$C_{20}$-heteroalkyl, substituted or unsubstituted $C_1$-$C_{20}$-alkoxy, or substituted or unsubstituted $C_6$-$C_{20}$-aryloxy;

$R^{22}$ is selected from H, substituted or unsubstituted $C_6$-$C_{20}$-aryl, or substituted or unsubstituted $C_5$-$C_{20}$-heteroaryl; each of $R^{23}$ and $R^{24}$ is independently selected from substituted or unsubstituted $C_6$-$C_{20}$-aryl or substituted or unsubstituted $C_5$-$C_{20}$-heteroaryl, and $R^{25}$ is O.

14. The compound according to claim 11 having a structure according to one of the following formulas:

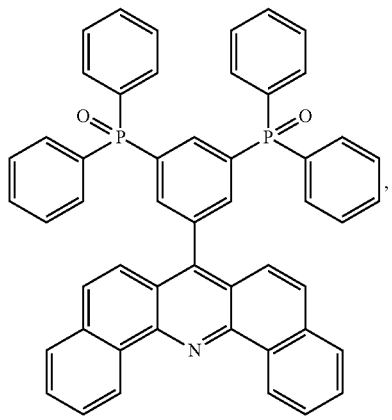

,

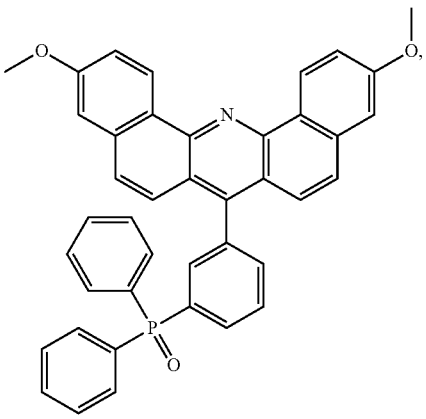

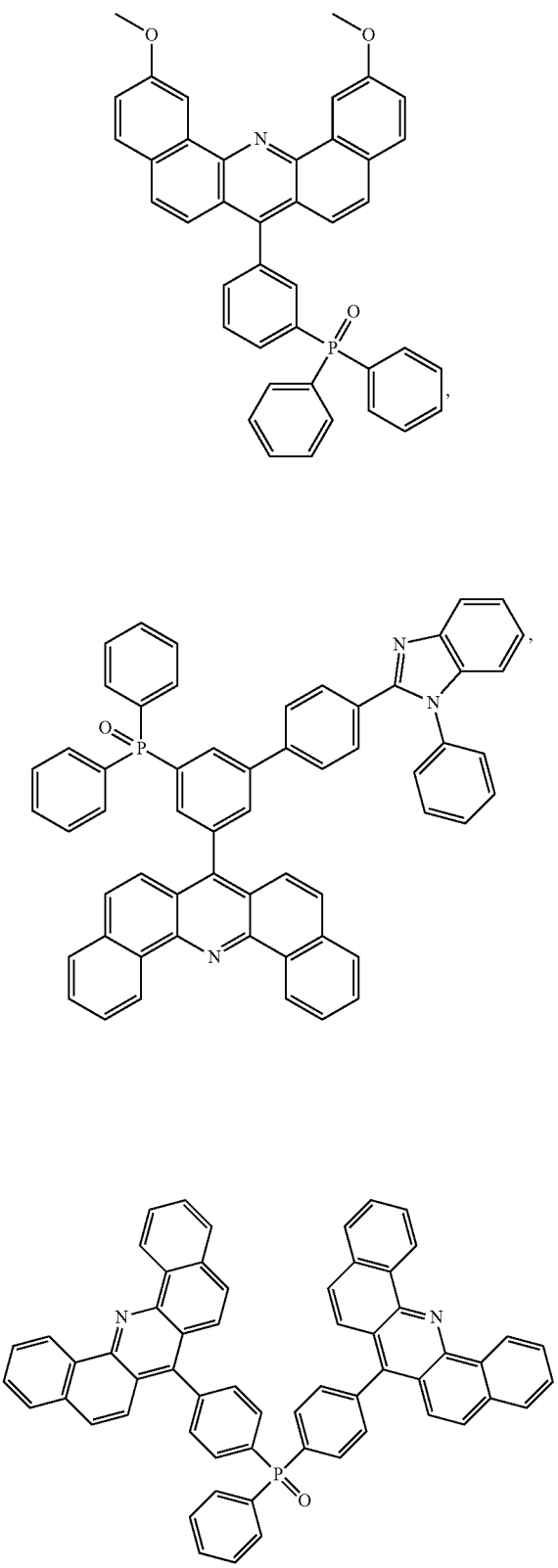
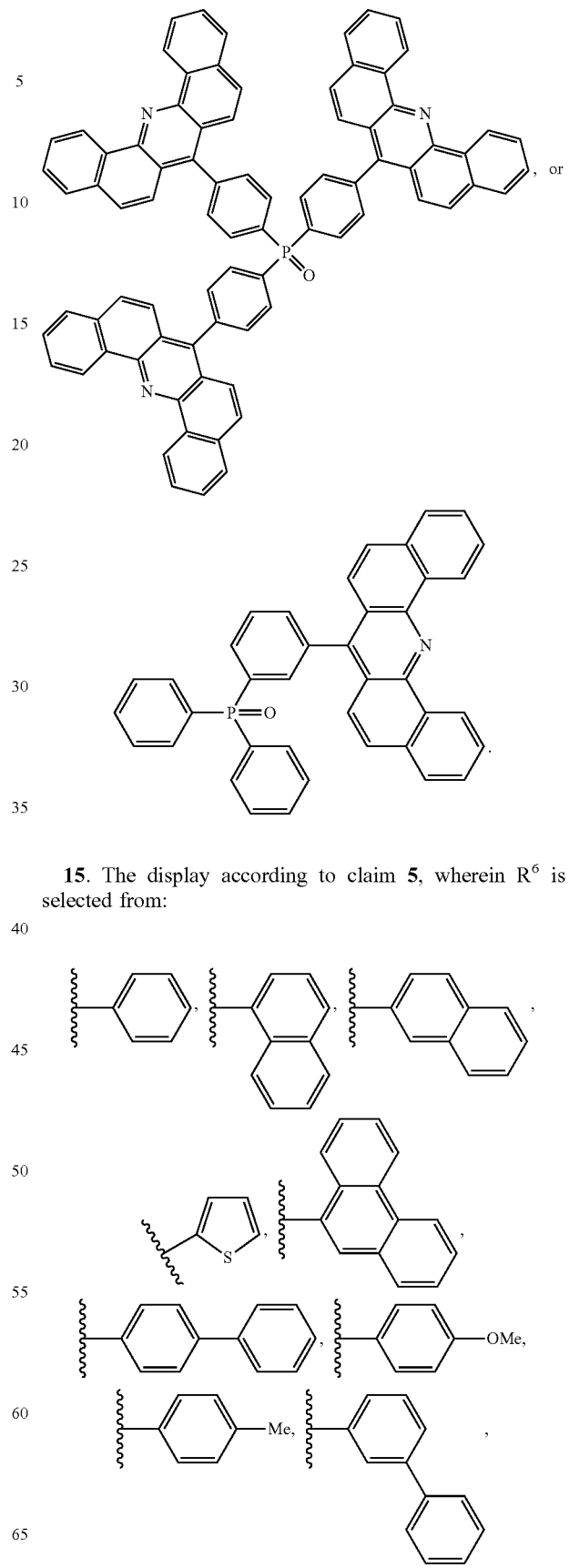
15. The display according to claim 5, wherein $R^6$ is selected from:

-continued
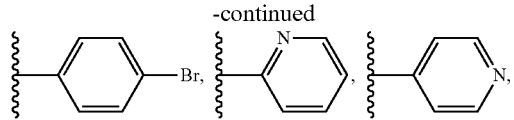
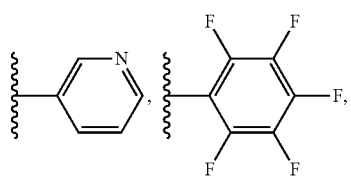
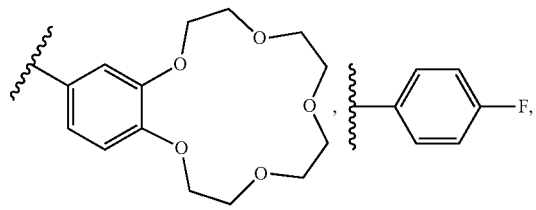
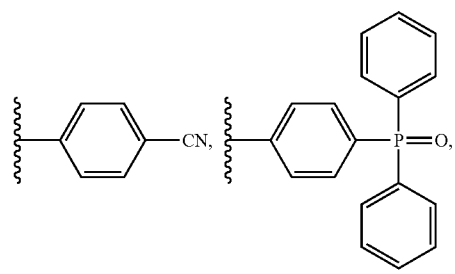
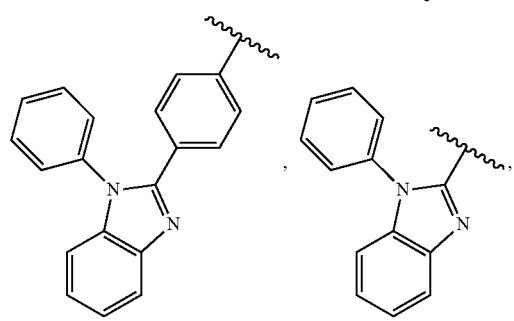
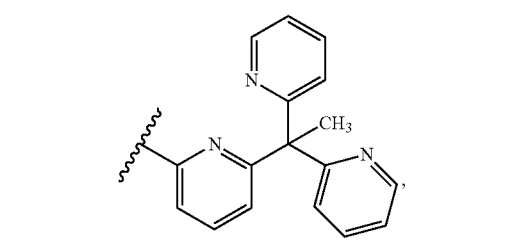
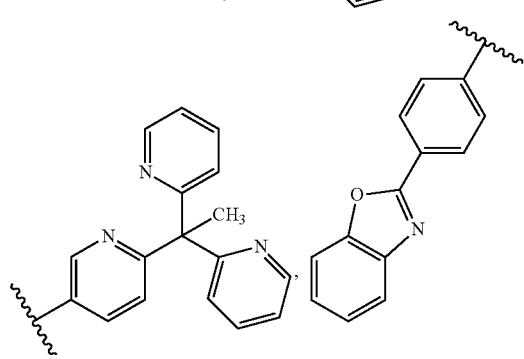
-continued
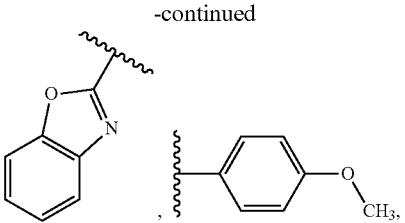
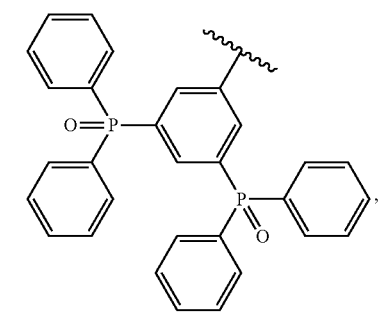
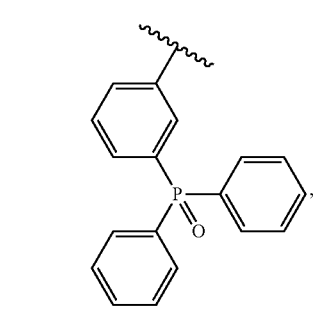
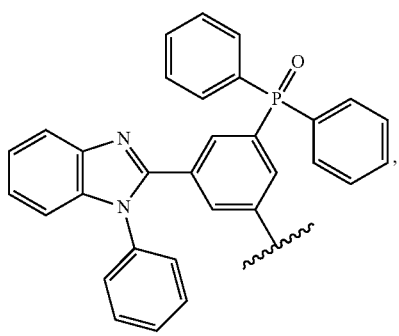
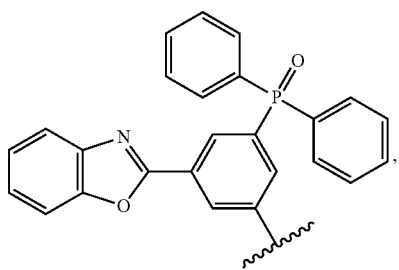

101
-continued
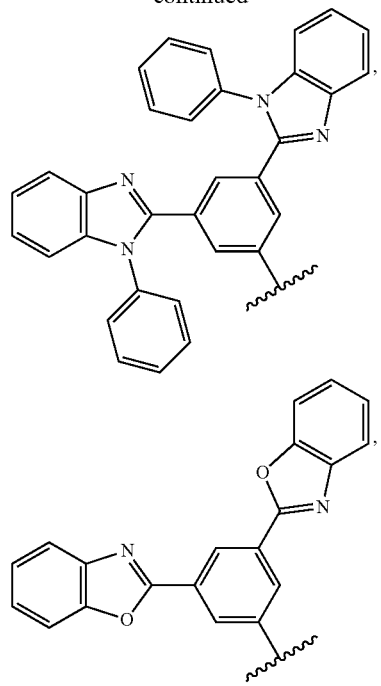
102
-continued
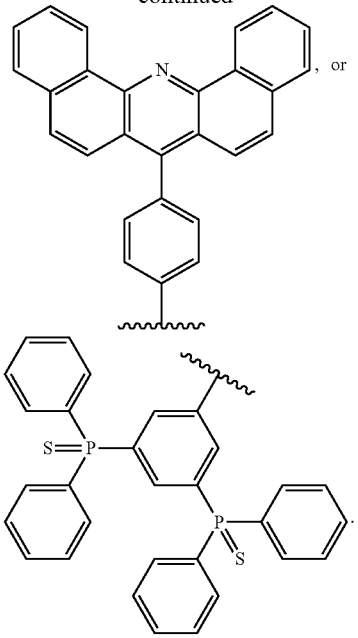
* * * * *